US012760102B2

(12) United States Patent
Navon et al.

(10) Patent No.: US 12,760,102 B2
(45) Date of Patent: Oct. 13, 2026

(54) ANTIBODIES SPECIFIC TO CTLA-4 AND USES THEREOF

(71) Applicants: Tikcro Technologies Ltd, Ness-Ziona (IL); Yeda Research and Development Co. Ltd., Rehovot (IL)

(72) Inventors: Ami Navon, Rehovot (IL); Aviv Boim, Herzliya (IL); Ariel Stanhill, Binyamina (IL); Leehee Weinberger, Rehovot (IL); Yuval Avnir, Kirat Ono (IL)

(73) Assignees: Tikcro Technologies Ltd, Ness-Ziona (IL); Yeda Research and Development Co. Ltd., Rehovot (IL)

( * ) Notice: Subject to any disclaimer, the term of this patent is extended or adjusted under 35 U.S.C. 154(b) by 1217 days.

(21) Appl. No.: 17/278,261

(22) PCT Filed: Sep. 20, 2019

(86) PCT No.: PCT/IB2019/001038
§ 371 (c)(1),
(2) Date: Mar. 19, 2021

(87) PCT Pub. No.: WO2020/058762
PCT Pub. Date: Mar. 26, 2020

(65) Prior Publication Data

US 2021/0355220 A1 Nov. 18, 2021
US 2023/0132385 A9 Apr. 27, 2023

Related U.S. Application Data

(60) Provisional application No. 62/825,629, filed on Mar. 28, 2019, provisional application No. 62/734,078, filed on Sep. 20, 2018.

(51) Int. Cl.
*C07K 16/28* (2006.01)
*A61K 39/00* (2006.01)

(52) U.S. Cl.
CPC .... *C07K 16/2818* (2013.01); *A61K 2039/505* (2013.01); *C07K 2317/34* (2013.01); *C07K 2317/565* (2013.01); *C07K 2317/622* (2013.01)

(58) Field of Classification Search
None
See application file for complete search history.

(56) References Cited

U.S. PATENT DOCUMENTS 6,984,720 B1 * 1/2006 Korman .................. A61P 31/18 530/387.9
2017/0281764 A1 10/2017 Tso et al.
2017/0283504 A1 * 10/2017 Wiltzius ............. C07K 16/2878

FOREIGN PATENT DOCUMENTS

WO WO 2016/196237 A1 12/2016
WO WO 2018/025178 A1 2/2018
(Continued)

OTHER PUBLICATIONS

Definition: variation. Merriam Webster dictionary. Accessed online. Aug. 26, 2024. https://www.merriam-webster.com/dictionary/variation (Year: 2024).*
(Continued)

*Primary Examiner* — Amy E Juedes
*Assistant Examiner* — Hilary Ann Petrash
(74) *Attorney, Agent, or Firm* — Wolf, Greenfield & Sacks, P.C.

(57) ABSTRACT

Disclosed herein are anti-CTLA-4 antibodies possessing superior binding and biological activities relative to ipibmumab and tremelimumab, pharmaceutical compositions comprising such. Also provided herein are therapeutic and diagnostic applications of such anti-CTLA-4 antibodies.

22 Claims, 22 Drawing Sheets

Specification includes a Sequence Listing.

(56) References Cited

FOREIGN PATENT DOCUMENTS

| | | | |
|---|---|---|---|
| WO | WO 2018/035710 | A1 | 3/2018 |
| WO | WO 2018/039097 | A1 | 3/2018 |
| WO | WO 2018/068182 | A1 | 4/2018 |

OTHER PUBLICATIONS

Definition: derive. Merriam Webster accessed online Aug. 26, 2024. https://www.merriam-webster.com/dictionary/derive (Year: 2024).*

Culang et al. The structural basis of antibody-antigen recognition. Front. Immunol., Oct. 8, 2013. Sec. B Cell Biology. vol. 4—2013 (Year: 2013).*

Kapingidza et al. (2020). Antigen-Antibody Complexes. In: Hoeger, U., Harris, J. (eds) Vertebrate and Invertebrate Respiratory Proteins, Lipoproteins and other Body Fluid Proteins. Subcellular Biochemistry, vol. 94. Springer, Cham. (Year: 2020).*

Teft et al. A molecular perspective of CTLA-4 Function. Annu. Rev. Immunol. 2006. 24:65-97 (Year: 2006).*

Damschroder et al. Analysis of human and primate CD2 molecules by protein sequence and epitope mapping with anti-human CD2 antibodies. Mol Immunol. Aug. 2004;41(10):985-1000 (Year: 2004).*

Steeland et al. Nanobodies as therapeutics: big opportunities for small antibodies. Drug Discover Today. vol. 21, No. 7, 2016 p. 1076-1113 (Year: 2016).*

Clark et al. Influence of canonical structure determining residues on antibody affinity and stability Journal of Structural Biology 185 (2014) 223-227 (Year: 2014).*

Brown et al. Tolerance to Single, but Not Multiple, Amino Acid Replacements in Antibody VH, CDR2. J Immunol (1996) 156 (9):3285-3291 (Year: 1996).*

Rouet, Fully Human VH Single Domains That Rival the Stability and Cleft Recognition of Camelid Antibodies. The Journal of Biological Chemistry vol. 290, No. 19, pp. 11905-11917, May 8, 2015 (Year: 2015).*

Holt et al., Domain antibodies: proteins for therapy, Trends in Biotechnology vol. 21 No. 11 Nov. 2003 (Year: 2003).*

International Search Report and Written Opinion for Application No. PCT/IB2019/001038 mailed Jan. 13, 2020.

International Preliminary Report on Patentability for Application No. PCT/IB2019/001038 mailed Jan. 13, 2020.

International Preliminary Report on Patentability for Application No. PCT/IB2019/001038 mailed Apr. 1, 2021.

Gombos et al., Toxicological and pharmacological assessment of AGEN1884, a novel human IgG1 anti-CTLA-4 antibody. PLoS One. Apr. 4, 2018;13(4):e0191926. doi: 10.1371/journal.pone.0191926.

Hendriks et al., Characterization of a novel differentiated anti-CTLA-4 antibody (ADU-1604) in vitro and in vivo. Journal for Immunotherapy of Cancer. Presented at BMC 2017, Campus, 4 Crinan St, London Ni 9xw, England.https://www.aduro.com/file.cfm/13/docs/SITC_2017_ADU-1604_Poster.pdf Last accessed Nov. 17, 2017] 2 pages.

Weinberger et al., A CTLA4 antibody with enhanced properties. Cancer Res. Jul. 1, 2019; 79 (13_Supplement): 3243. Presented at AACR Annual Meeting Atlanta, GA, Mar. 29-Apr. 3, 2019. doi:10.1158/1538-7445.AM2019-3243. https://cancerres.aacrjournals.org/content/79/13_Supplement/3243 [last accessed Jul. 1, 2025] 2 pages.

* cited by examiner

| | Conc. (ug/ml) | | | | | | | |
|---|---|---|---|---|---|---|---|---|
| Ab55h | 30 | 30 | 10 | 10 | 3 | 3 | 0 | 0 |
| Nivolumab | 0 | 10 | 0 | 10 | 0 | 10 | 0 | 10 |
| hIgG1 isotype | 0 | 0 | 0 | 0 | 0 | 0 | 30 | 0 |

| | Conc. (ug/ml) | | | | | | | |
|---|---|---|---|---|---|---|---|---|
| Ab55h | 30 | 30 | 10 | 10 | 3 | 3 | 0 | 0 |
| Nivolumab | 0 | 10 | 0 | 10 | 0 | 10 | 0 | 10 |
| hIgG1 isotype | 0 | 0 | 0 | 0 | 0 | 0 | 30 | 0 |

| | | | | | | | | | | |
|---|---|---|---|---|---|---|---|---|---|---|
| Ab55h | 30 | 30 | 0 | 0 | 10 | 10 | 0 | 0 | 0 | 0 |
| Ipilimumab replica | 0 | 0 | 30 | 30 | 0 | 0 | 10 | 10 | 0 | 0 |
| Nivolumab | 0 | 10 | 0 | 10 | 0 | 10 | 0 | 10 | 10 | 0 |

| | | | | | | | | | | |
|---|---|---|---|---|---|---|---|---|---|---|
| Ab55h | 30 | 30 | 0 | 0 | 10 | 10 | 0 | 0 | 0 | 0 |
| Ipilimumab replica | 0 | 0 | 30 | 30 | 0 | 0 | 10 | 10 | 0 | 0 |
| Nivolumab | 0 | 10 | 0 | 10 | 0 | 10 | 0 | 10 | 10 | 0 |

Fig. 13A, continued
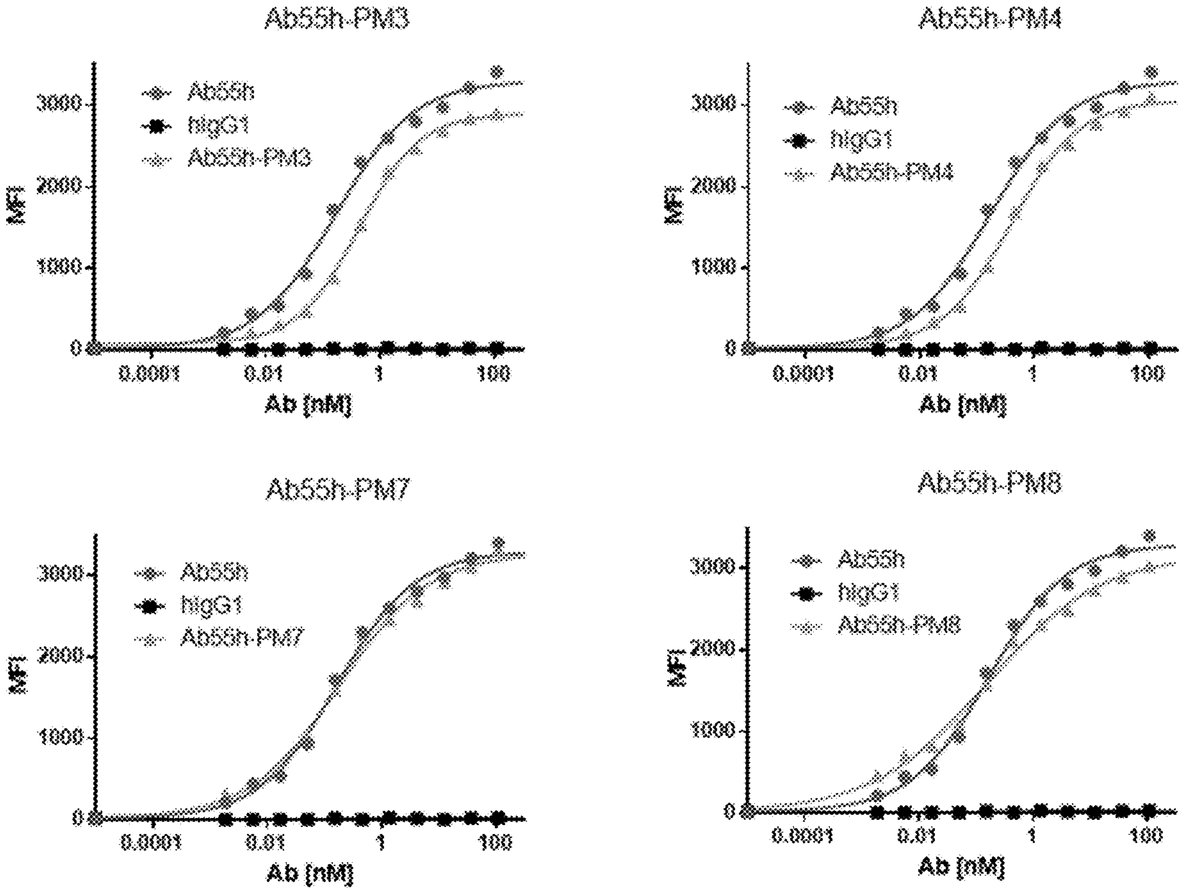

Fig. 13B, continued
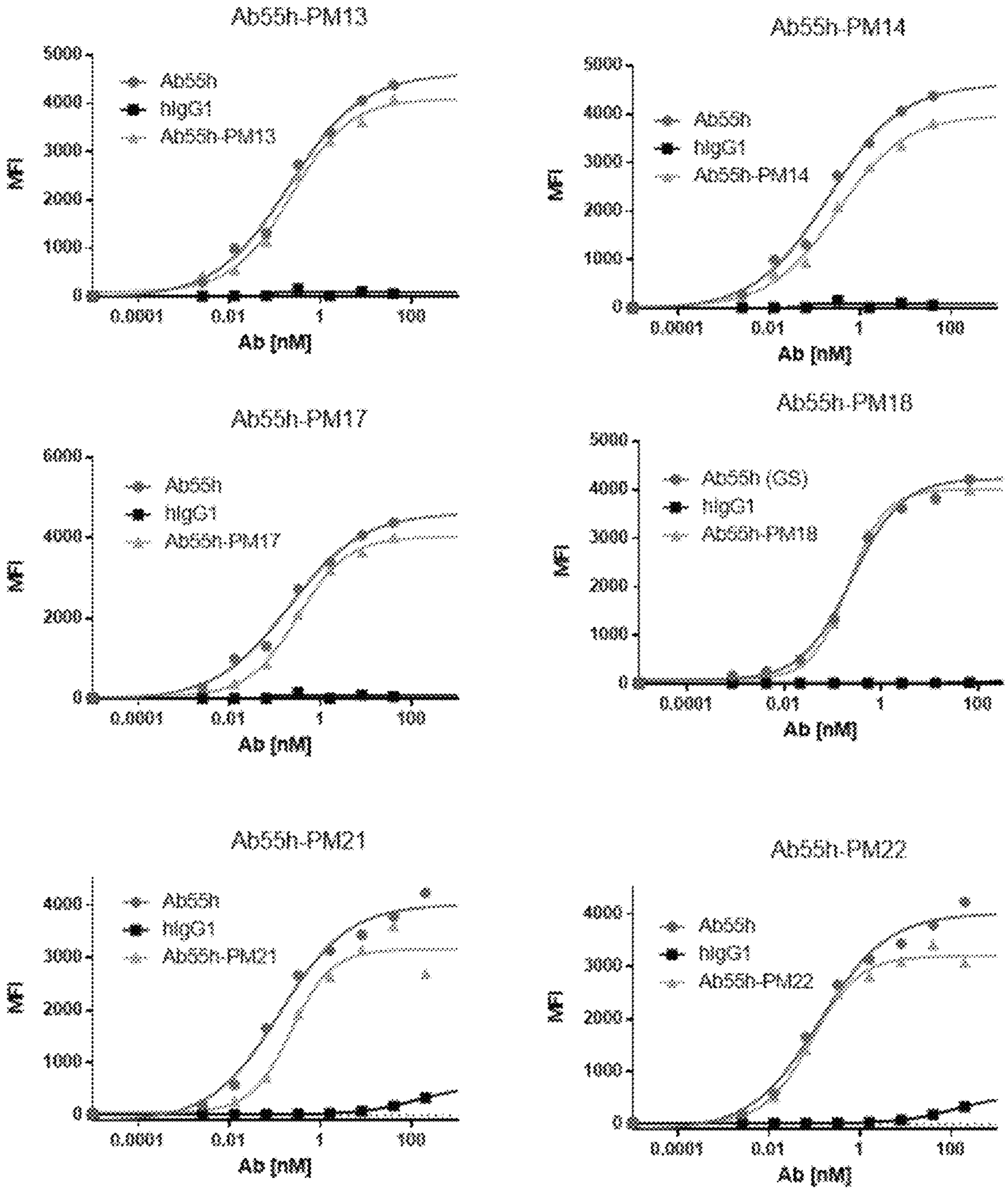

Fig. 13D, continued
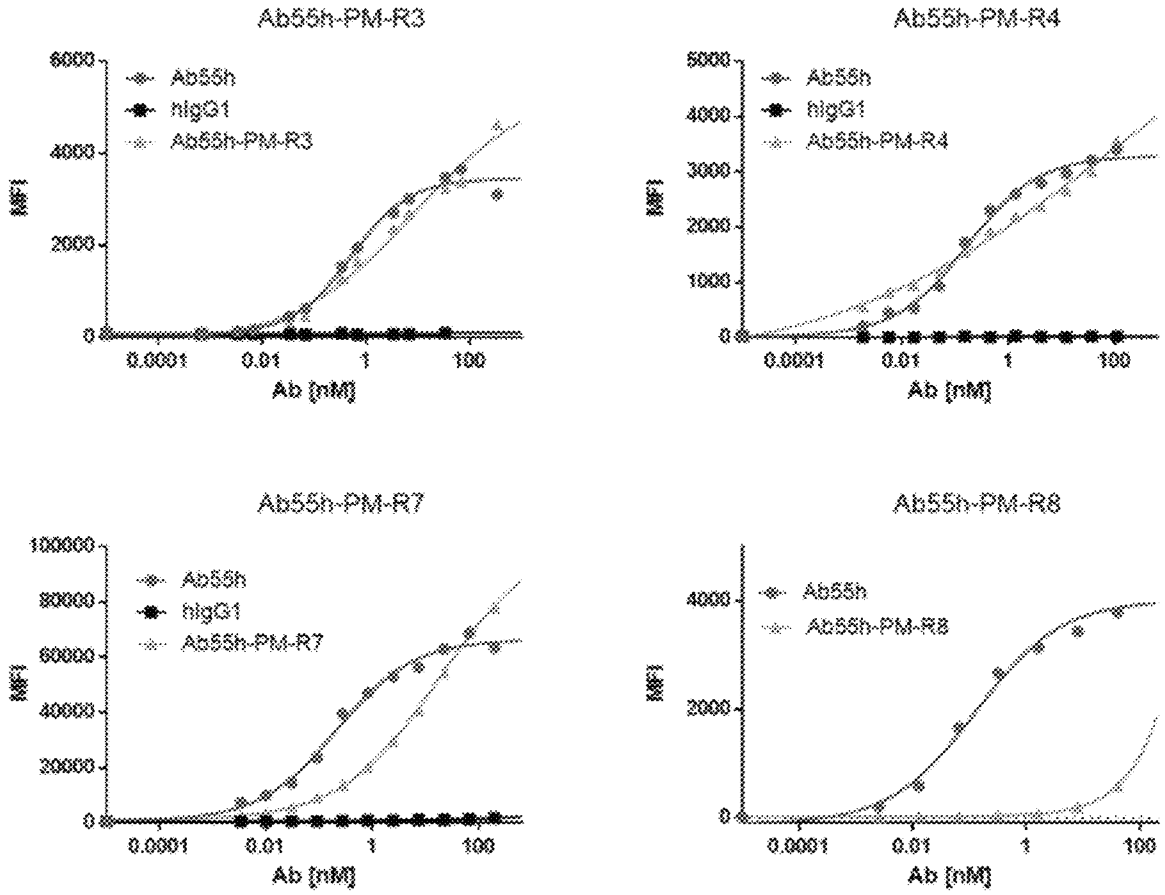

ANTIBODIES SPECIFIC TO CTLA-4 AND USES THEREOF

RELATED APPLICATIONS

This application is a national stage filing under 35 U.S.C. § 371 of International Patent Application Serial No. PCT/IB2019/001038, filed Sep. 20, 2019, which claims the benefit under 35 U.S.C. § 119(e) of U.S. Provisional Application Ser. No. U.S. 62/734,078, filed Sep. 20, 2018 and U.S. Provisional Application Ser. No. 62/825,629, filed Mar. 28, 2019, the entire disclosures of each of which are herein incorporated by reference in their entireties.

BACKGROUND OF INVENTION

Cytotoxic T-lymphocyte-associated protein 4 (CTLA-4), also called cluster of differentiation 152 (CD152), is a protein receptor expressed by activated T cells and constitutively expressed in regulatory T cells. CTLA-4 downregulates immune responses by transmitting inhibitory signals to T cell receptor signaling. It is homologous to CD28, a T cell co-stimulatory protein, and both receptors bind CD80 and CD86 on antigen presenting cells; however, CTLA-4 binds the two ligands with greater affinity than CD28. T cell activation through the T cell receptor and CD28 leads to increased expression of CTLA-4.

SUMMARY OF INVENTION

The present disclosure is based, at least in part, on the development of anti-CTLA-4 antibodies having superior binding and/or biological activities as compared with known therapeutic anti-CTLA-4 antibodies, such as ipilimumab and tremelimumab, for example, higher binding affinity and specificity, higher blocking capabilities and better anti-tumor activity as shown in animal models.

Accordingly, one aspect of the present disclosure features monoclonal antibodies that bind to cytotoxic T-lymphocyte-associated protein 4 (CTLA-4), such as human CTLA-4 (i.e., anti-CTLA-4 antibody).

In some embodiments, the monoclonal anti-CTLA-4 antibody disclosed herein may bind the same epitope as Ab55h or competes against Ab55h from binding to the CTLA-4 target. Such an antibody may specifically binds human CTLA-4. Alternatively, the antibody may cross-react with human CTLA-4 and a non-human CTLA-4 (e.g., a non-human primate CTLA-4, a pig CTLA-4, or a mouse CTLA-4). In some instances, the anti-CTLA-4 is capable of binding to the CTLA-4 antigen expressed on cell surface.

In some embodiments, an anti-CTLA-4 antibody as disclosed herein comprises a heavy chain variable domain ($V_H$), which comprises (i) a heavy chain complementary determining region 1 (HC CDR1) set forth as GDYYWX$_1$ (SEQ ID NO: 3), in which $X_1$ is G or N, (ii) a heavy chain complementary determining region 2 (HC CDR2) set forth as SIYHX$_2$X$_3$YTYYNPSX$_4$KS (SEQ ID NO: 4), in which $X_2$ is D or S, $X_3$ is G or A, and $X_4$ is L or V; and (iii) a heavy chain complementary determining region 3 (HC CDR3) set forth as DSGWYVIAFX$_5$X$_6$ (SEQ ID NO: 5), in which $X_5$ is D or A, and $X_6$ is Y or I. Alternatively or in addition, the antibody comprises a light chain variable domain ($V_L$), which comprises (i) a light chain complementary determining region 1 (LC CDR1) set forth as RASQSX$_7$SSNLA (SEQ ID NO: 6), in which $X_7$ is V or I; (ii) a light chain complementary determining region 2 (LC CDR2) set forth as X$_8$AX$_9$X$_{10}$RAT (SEQ ID NO: 7), in which $X_8$ is A or G and each of $X_9$, $X_{10}$ is independently S or T; and (iii) a light chain complementary determining region 3 (LC CDR3) set forth as QQYNNWPPLT (SEQ ID NO: 8).

In some embodiments, an anti-CTLA-4 antibody as disclosed herein may comprise a HC CDR1, a HC CDR2, and a HC CDR3, which collectively contains no more than 10 amino acid variations (e.g., no more than 8 amino acid variations, or no more than 5 amino acid variations) as compared with the HC CDR1, HC CDR2, and HC CDR3 of Ab55h; and/or a LC CDR1, a LC CDR2, and a LC CDR3, which collectively contains no more than 10 amino acid variations (e.g., no more than 8 amino acid variations, or no more than 5 amino acid variations) as compared with the LC CDR1, LC CDR2, LC CDR3 of Ab55h.

In some embodiments, an anti-CTLA-4 antibody as disclosed herein may comprise a HC CDR1, a HC CDR2, and a HC CDR3, at least one of which (e.g., HC CDR3) contains no more than 5 amino acid variations (e.g., no more than 4, 3, or 2 amino acid variations) as the counterpart HC CDR of Ab55h; and/or a LC CDR1, a LC CDR2, and a LC CDR3, at least one of which contains no more than 5 amino acid variations (e.g., no more than 4, 3, or 2 amino acid variations) as the counterpart LC CDR of Ab55h.

In some embodiments, an anti-CTLA-4 antibody as disclosed herein may comprise a heavy chain variable domain that is at least 85% identical to the heavy chain variable domain of Ab55h, and/or a light chain variable domain that is at least 85% identical to the light chain variable domain of Ab55h.

In some specific examples, the anti-CTLA-4 antibody disclosed herein may comprise the same heavy chain complementary determining regions (HC CDRs) and/or the same light chain complementary determining regions (LC CDRs) as Ab55h. For example, such an anti-CTLA-4 antibody may comprise the same heavy chain variable domain as Ab55h and/or the same light chain variable domain as Ab55h.

In some examples, any of the anti-CTLA-4 antibodies described herein may be a human antibody of a humanized antibody. In some examples, any of the anti-CTLA-4 antibody described herein may be a full-length antibody (e.g., an IgG molecule), which may contain an altered Fc fragment relative to a naturally-occurring counterpart, or an afucosylated Fc fragment. Afucosylated IgG molecules would be expected to exhibit enhanced ADCC effect relative to the fucosylated counterpart. Alternatively, the anti-CTLA-4 antibody may be an antigen-binding fragment, for example, Fab, Fab', F(ab')$_2$, or Fv. In other examples, the anti-CTLA-4 antibody may be a single-chain antibody (scFv), a bispecific antibody, or a nanobody.

Any of the anti-CTLA-4 antibodies disclosed herein may be conjugated with a detectable label.

In another aspect, provided herein is a nucleic acid or a nucleic acid set, which collectively encode the antibody binding to any of the CTLA-4 antibodies described herein. A nucleic acid set refers to two nucleic acid molecules one encoding the heavy chain and the other encoding the light chain of a multi-chain anti-CTLA-4 antibody disclosed herein. In some examples, the nucleic acid or nucleic acid set can be a vector or a vector set, for example, an expression vector or an expression vector set. Also provide herein are host cells comprising the vector or vector set disclosed herein. Such host cells can be bacterial cells, yeast cells, insect cells, plant cells, or mammalian cells.

In yet another aspect, the present disclosure features a chimeric receptor comprising an extracellular domain and at least one cytoplasmic signaling domain, wherein the extracellular domain is a single chain antibody derived from any of the anti-CTLA-4 antibodies disclosed herein. The single chain antibody comprises a heavy chain variable domain and/or a light chain variable domain set forth in any one of the anti-CTLA-4 antibodies disclosed herein.

In addition, the present disclosure features a pharmaceutical composition, comprising (a) a monoclonal antibody binding to CTLA-4 as disclosed herein, or the encoding nucleic acid(s), and (b) a pharmaceutically acceptable carrier. Such a pharmaceutical composition can be used for treating any of the target diseases also disclosed herein. Further, the present disclosure provides uses of the antibodies, the encoding nucleic acids, or other aspects relating to the antibody as disclosed herein for manufacturing a medicament for use in treatment of the target disease.

Further, the present disclosure features a method for modulating immune responses in a subject, the method comprising administering to a subject in need thereof an effective amount of the pharmaceutical composition disclosed herein. In some examples, the subject is a human patient having, suspected of having, or at risk for a disease, which is a cancer, an inflammatory disease or an infectious disease. In some examples, the human patient has a metastatic cancer. In some examples, the human patient has a cancer with a high mutation burden.

Exemplary cancers include, but are not limited to, lung cancer, melanoma, renal cancer, liver cancer, myeloma, prostate cancer, breast cancer, colorectal cancer, gastric cancer, esophageal and EGJ carcinoma, pancreatic cancer, thyroid cancer, hematological cancer, lymphoma, leukemia, skin cancer, ovarian cancer, bladder cancer, urothelial carcinoma and head and neck cancer. In some examples, the human patient has a cancer that would benefit from enhancing immune responses.

In some examples, the human patient has microsatellite instability-high (MSI-H) or mismatch repair deficient (dMMR), found in soft tissue cancer, glioblastoma, esophageal and EGJ carcinoma, breast carcinoma, non-small cell lung cancer, ovarian surface epithelial carcinomas, cancer of unknown primary, small cell lung cancer, non-epithelial ovarian cancer, pancreatic adenocarcinoma, other female genital tract malignancies, uveal melanoma, retroperitoneal or peritoneal sarcoma, thyroid carcinoma, uterine sarcoma, cholangiocarcinoma, prostate adenocarcinoma, hepatocellular carcinoma, neuroendocrine tumors, cervical cancer, colorectal adenocarcinoma, small intestinal malignancies, gastric adenocarcinoma and endometrial cancer.

In some examples, the subject has undergone or is undergoing an additional treatment of the disease. For example, if the subject is a cancer patient, the subject may have been subjected to a cancer therapy or is co-treated by a cancer therapy. Examples include surgery, a chemotherapy, an immune therapy, a radiotherapy, a transplantation, or a combination thereof. In one specific example, the treatment comprises administering to the subject an immune checkpoint antagonist (e.g., an anti-PD-1 or anti-PDL-1 antibody such as nivolumab, pembrolizumab, or avelumab, durvalumab and atezolizumab).

Further, the present disclosure provides a method for producing an antibody binding to CTLA-4, the method comprising: (i) culturing the host cell comprising nucleic acid(s) encoding any of the anti-CTLA-4 antibodies disclosed herein in a medium for production of the antibody; and (ii) collecting the host cell or the medium for isolation of the antibody. Optionally, the method may further comprise (iii) purifying the antibody from the host cell or the medium.

In addition, the present disclosure also provides a method for detecting presence of CTLA-4, the method comprising contacting an anti-CTLA-4 antibody as disclosed herein, which may be conjugated to a detectable label, with a biological sample suspected of containing CTLA-4, and measuring binding of the anti-CTLA-4 antibody to CTLA-4 in the sample. This method may be performed in vivo comprising administering the anti-CTLA-4 antibody to a subject in need thereof.

The details of one or more embodiments of the invention are set forth in the description below. Other features or advantages of the present invention will be apparent from the following drawing and detailed description of several embodiments, and also from the appended claims.

BRIEF DESCRIPTION OF DRAWINGS

The following drawing forms part of the present specification and are included to further demonstrate certain aspects of the present disclosure, which can be better understood by reference to one or more of these drawings in combination with the detailed description of specific embodiments presented herein.

FIG. 2A is a graph showing the binding of Ab55h and control hIgG1 antibody to dimer and monomer forms of hCTLA-4 using an ELISA. FIG. 2B is a graph Ab55h binding to hCTLA-4, which was analyzed using Western blot.

FIG. 3A shows the binding of the selected antibodies to macaque (*Macaca fascicularis*) CTLA-4. FIG. 3B shows the binding of the selected antibodies to pig (*Sus scrofa*) CTLA-4. FIG. 3C shows the binding of the selected antibodies to mouse (*Mus musculus*) CTLA-4.

FIG. 4A shows the fraction bound of CD80 to CTLA-4-expressing HEK293 cells in the presence of the indicated antibodies. FIG. 4B shows the fraction bound of CD86 to CTLA-4-expressing HEK293 cells in the presence of the indicated antibodies.

FIG. 5A shows the MFI of the indicated antibodies binding to HEK293-CTLA-4 cells in the presence of CD80. FIG. 5B shows the MFI of the indicated antibodies binding to HEK293-CTLA-4 cells in the presence of CD86.

FIG. 6A is a graph showing the percentage of hCTLA-4 cells from six different donors bound by the given antibodies over time. FIG. 6B shows the percentage of hCTLA-4 cells from one donor bound at different concentrations of the antibodies indicated.

FIG. 8A shows the IL-2 concentrations from different combinations of Ab55h and nivolumab compared to a hIgG1 isotype control antibody. FIG. 8B shows the IL-2 concentrations from different combinations of Ab55h with or without nivolumab, as compared to different combinations of the ipilimumab control antibody with or without nivolumab.

FIG. 9A is a schematic depicting the NFAT reporter assay. FIG. 9B is a graph showing the normalized luciferase signal for each antibody at different concentrations following the NFAT reporter assay.

FIG. 10A is a schematic depicting the SHP1 reporter activity assay. FIG. 10B is a graph showing the normalized luciferase signal for each antibody at different concentrations following the SHP1 reporter activity assay.

FIG. 11A shows the mean tumor size over time during the studies. FIG. 11B shows the median tumor size over time during the studies. FIG. 11C shows spider plots of tumor size in individual mice following tumor injection. The top row shows days 5-23, while the bottom row shows days 5-51. The shaded area makes the mice with tumor sizes >310 $mm^3$ on day 20. FIG. 11D is a survival plot of the mice during the trial. CR=complete response. *=p-value<0.05; ***=p-value<0.0005. The statistical analysis for survival was performed with Log-Rank test comparing Ab55h and PBS groups.

DETAILED DESCRIPTION OF INVENTION

Figure 1:
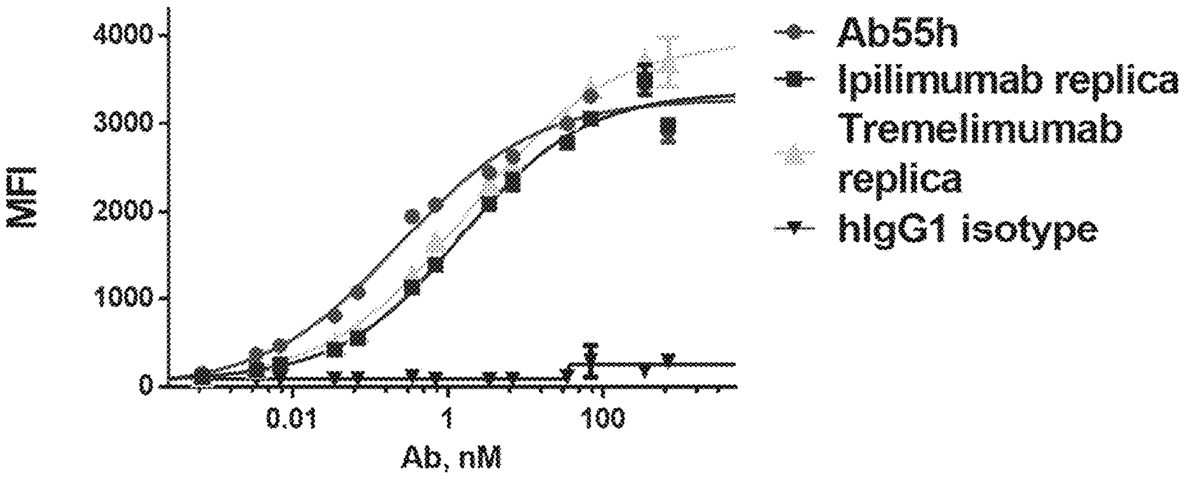
FIG. 1 is a graph showing the Mean Fluorescent Intensity (MFI) for the different antibodies tested, indicating the binding of each antibody to HEK293 cells overexpressing human CTLA-4.

The present disclosure is based, at least in part, on the development of anti-CTLA-4 antibodies, which possessed unexpected superior features compared with known therapeutic anti-CTLA-4 antibodies such as ipilimumab and tremelimumab. Such superior features include at least the following:

(i) at least 8-fold higher binding affinity (e.g., Kd ranging from $10^{-9}$ to $10^{-10}$) to human CTLA-4 than ipilimumab as determined by surface plasmon resonance (SPR);

(ii) at least 6-fold higher binding activity to cell surface displayed-human CTLA-4 relative to lpilimumab and tremelimumab;

(iii) antigen-binding specificity to CTLA-4 across species different from that of lpilimumab and tremelimumab;

(iv) higher blocking activity against binding of CD80/CD86 to CTLA-4 relative to lpilimumab or tremelimumab (e.g., at least 3-fold higher of CD80 than lpilimumab);

(v) higher blocking activity against downstream signaling relative to lpilimumab or tremelimumab;

(vi) capable of competing against lpilimumab or tremelimumab from binding to human CTLA-4 but ipilimumab or tremelimumab with the presence of the antibodies do not compete as effectively;

(vii) superior cell internalization effect relative to lpilimumab; which is expected to result in an enhanced immune system activation (see descriptions below); and (viii) superior anti-tumor activity relative to lpilimumab as observed in an animal model.

Further, the anti-CTLA-4 antibody disclosed herein may possess additional superior/unexpected features, for example, (a) binding to both monomer and dimer CTLA-4 but not denatured CTLA-4, (b) no or insignificant cross-reactivity to other related immune receptors, such as hBTLA, hICOS, hCD28, hPDL1, hPD1, hPDL2; (c) capable of activating peripheral blood mononuclear cells (PBMCs), (d) exhibited superior immune cell activation activity in combination with an immune checkpoint antagonist such as an anti-human-PD-1 antibody; and (e) achieved immunological memory anti-tumor effect as observed in an animal model.

Accordingly, provided herein are antibodies capable of binding CTLA-4, as well as nucleic acids encoding said antibodies, and uses thereof for both therapeutic and diagnostic purposes. Also provided herein are kits for therapeutic and/or diagnostic use of the antibodies, as well as methods for producing anti-CTLA-4 antibodies. In addition, the present disclosure provides chimeric antigen receptors comprising extracellular antigen binding domains derived from any of the anti-CTLA-4 antibodies described herein.

Antibodies Binding to CTLA-4

The present disclosure provides antibodies that bind cytotoxic T-lymphocyte-associated protein 4 (CTLA-4), for example, cell surface-displayed CTLA-4. In some embodiments, the anti-CTLA-4 antibody binds CTLA-4 in both monomer and dimer form. Alternatively or in addition, the anti-CTLA-4 antibody has low binding affinity (e.g., Kd>$10^{-5}$ M) to denatured CTLA-4 or does not bind to the denatured CTLA-4.

As a member of the immunoglobulin superfamily, CTLA-4, also known as CD152, is a member of the immunoglobulin superfamily. It is a protein receptor expressed by activated T cells and constitutively expressed in regulatory T cells, which may have important implications in cancer immunotherapy. CTLA-4 may function as an immune checkpoint, which downregulates immune responses. CTLA-4 was found to be upregulated in conventional T cells after activation, which is particularly notable in cancer. The human CTLA-4 protein is encoded by the CTLA4 gene.

CTLA-4 is a single pass transmembrane protein composed of: an IgG like (V-Set) domain, a transmembrane domain and a cytoplasmic tail. Alternate splice variants encoding different isoforms have been characterized. The membrane-bound isoform functions as a homodimer connected with a disulfide bond, and the soluble form exists as a monomer. The intracellular domain of CTLA-4 has no intrinsic catalytic activity and contains one YVKM motif able to bind PI3K, PP2A, and SHP-2 and one proline-rich motif able to bind SH3-containing proteins. The amino acid sequence of human CTLA-4 is well known in the art, e.g., GenBank Accession Number NP_005205.2.

An antibody (interchangeably used in plural form) is an immunoglobulin molecule capable of specific binding to a target antigen (e.g., CTLA-4 in the present disclosure), through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest, Fifth Edition*, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs.

In some embodiments, the anti-CTLA-4 antibody as described herein can bind and inhibit the activity of the CTLA-4 receptor by at least 50% (e.g., 60%, 70%, 80%, 90%, 95% or greater). The apparent inhibition constant ($Ki^{app}$ or $K_{i,app}$), which provides a measure of inhibitor potency, is related to the concentration of inhibitor required to reduce enzyme activity and is not dependent on enzyme concentrations. The inhibitory activity of an anti-CTLA-4 antibody described herein can be determined by routine methods known in the art.

The antibodies described herein can be murine, rat, human, primate, porcine, or any other origin (including chimeric or humanized antibodies). Such antibodies are non-naturally occurring, i.e., would not be produced in an animal without human act (e.g., immunizing such an animal with a desired antigen or fragment thereof).

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-CTLA-4 antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (CTLA-4) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen (e.g., binding not detectable in a conventional assay).

In some embodiments, the antibodies described herein specifically bind to CTLA-4 as relative to other related immune receptors, for example, BTLA, ICOS, CD28, PDL1, PD1, or PDL2. In some embodiments, the antibodies described herein do not bind to one or more of the related immune receptors such as those described herein. In some embodiments, the antibodies described herein do not bind to one more of the related immune receptors expressed on cell surface (e.g., expressed on the surface of HEK293 cells).

In some embodiments, the antibodies described herein specifically binds to CTLA-4 of a specific species (e.g., human CTLA-4) as relative to CTLA-4 from other species. For example, the antibodies described herein may specifically binds to human CTLA-4 as relative to mouse CTLA-4. In other embodiments, the antibodies described herein may cross-react with human CTLA-4 and one or more CTLA-4 from a non-human species (e.g., a non-human primate such as macaque or pig). In some embodiments, the antibodies cross-react with human, macaque, and pig CTLA-4 with similar binding affinity but have significantly lower binding affinity to mouse CTLA-4.

In some embodiments, an anti-CTLA-4 antibody as described herein has a suitable binding affinity for the target antigen (e.g., human CTLA-4) or antigenic epitopes thereof. As used herein, "binding affinity" refers to the apparent association constant or $K_A$, which is the ratio of association and dissociation constants, K-on and K-off, respectively. The $K_A$ is the reciprocal of the dissociation constant ($K_D$). The anti-CTLA-4 antibody described herein may have a binding affinity ($K_D$) of at least $10^{-8}$, $10^{-9}$, $10^{-10}$ M, or lower for the target antigen or antigenic epitope. For example, the anti-CTLA-4 antibody may have a binding affinity of $10^{-9}$ M, $10^{-10}$ M or lower to human CTLA-4. An increased binding affinity corresponds to a decreased value of $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof or a second protein). In some embodiments, the anti-CTLA-4 antibodies described herein have a higher binding affinity (a higher $K_A$ or smaller $K_D$) to CTLA-4 as compared to the binding affinity to another immune modulator protein (e.g., BTLA, ICOS, PDL1, PD1, or PDL2). In some embodiments, the anti-CTLA-4 antibody may have a higher binding affinity to a CTLA-4 of a specific species (e.g., human CTLA-4) than that to a CTLA-4 from a different species (e.g., mouse). Differences in binding affinity (e.g., for specificity or other comparisons) can be at least 1.5, 2, 2.5, 3, 4, 5, 10, 15, 20, 37.5, 50, 70, 80, 91, 100, 500, 1,000, 5,000, 10,000 or $10^5$ fold. In some embodiments, any of the anti-CTLA-4 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance (SPR), florescent activated cell sorting (FACS) or spectroscopy (e.g., using a fluorescence assay). Exemplary conditions for evaluating binding affinity are in HBS-P buffer (10 mM HEPES pH 7.4, 150 mM NaCl, 0.005% (v/v) surfactant P20) and PBS buffer (10 mM $PO_4^{-3}$, 137 mM NaCl, and 2.7 mM KCl). These techniques can be used to measure the concentration of bound proteins as a function of target protein concentration. The concentration of bound protein ([Bound]) is generally related to the concentration of free target protein ([Free]) by the following equation:

$$[\text{Bound} = [\text{Free}]/(Kd + [\text{Free}])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the anti-CTLA-4 antibodies disclosed herein exhibit one or more bioactivities, including blocking the binding of CD80 and/or CD86 to CTLA-4, competing against lpilimumab or tremelimumab from binding to human CTLA-4 but not vice versa; activating immune cells such as T cells, inhibiting reducing, or eliminating tumor cell, or any combination thereof.

In some embodiments, the anti-CTLA-4 antibody comprises a heavy chain variable region that comprises a heavy chain CDR1 (HC CDR1), a heavy chain CDR2 (HC CDR2), and a heavy chain CDR3 (HC CDR3). For example, following the Kabat definition, the HC CDR1 may comprise the amino acid sequence of $X_1X_2YYWX_3$ (SEQ ID NO: 9), in which $X_1$ is G or S, $X_2$ is D or S, and $X_3$ is G or N; the HC CDR2 may comprise the amino acid sequence of SIYH$X_4X_5$YTYYNPS$X_6$KS (SEQ ID NO: 10), in which $X_4$ is D or S, $X_5$ is G or A, and $X_6$ is L or V; and/or the HC CDR3 may comprise the amino acid sequence of $X_7X_8$G $X_9$YVI $X_{10}X_{11}X_{12}X_{13}$ (SEQ ID NO: 11), in which $X_7$ is D or G, $X_8$ is S or V, $X_9$ is W, F, or A, $X_{10}$ is A or G, $X_{11}$ is F or Y, $X_{12}$ is D or A, and $X_{13}$ is Y or I.

In one embodiment, following the Kabat definition, the HC CDR1 may comprise the amino acid sequence of GDYYW$X_1$ (SEQ ID NO: 3), in which $X_1$ is G or N; the HC CDR2 may comprise the amino acid sequence of SIYH$X_2X_3$YTYYNPS$X_4$KS (SEQ ID NO: 4), in which $X_2$ is D or S, $X_3$ is G or A, and $X_4$ is L or V; and/or the HC CDR3 may comprise the amino acid sequence of DSGWYVIAF$X_5X_6$ (SEQ ID NO: 5), in which, $X_5$ is D or A, and $X_6$ is Y or I.

Alternatively or in addition, the anti-CTLA-4 antibody comprises a light chain variable region that comprises a light chain CDR1 (LC CDR1), a light chain CDR2 (LC CDR2), and a light chain CDR3 (LC CDR3). For example, following the Kabat definition, the LC CDR1 may comprise the amino acid sequence of RASQS$X_{14}X_{15}$S$X_{16}$LA (SEQ ID NO: 12), in which $X_{14}$ is V or I, $X_{15}$ is S, G, or Y, and $X_{16}$ is Y or N; the LC CDR2 comprises the amino acid sequence of $X_{17}$A$X_{18}X_{19}$RA$X_{20}$ (SEQ ID NO: 13), in which $X_{17}$ is A or G and each of $X_{18}$, $X_{19}$, and $X_{20}$ is independently S or T; and/or the LC CDR3 comprises the amino acid sequence of QQY$X_{21}X_{22}X_{23}$PP$X_{24}$T (SEQ ID NO: 14), in which $X_{21}$ is N, G, or A, $X_{22}$ is N, S, or V, $X_{23}$ is W or S, and $X_{24}$ is L, I, or F. In some embodiments, $X_{20}$ is T, $X_{21}$ is N, and/or $X_{22}$ is N.

Alternatively or in combination, following the Kabat definition, the LC CDR1 may comprise the amino acid sequence of RASQS$X_7$SSNLA (SEQ ID NO: 6), in which $X_7$ is V or I the LC CDR2 comprises the amino acid sequence of $X_8$A$X_9X_{10}$RAT (SEQ ID NO: 7), in which $X_8$ is A or G and each of $X_9$, and $X_{10}$ is independently S or T; and/or the LC CDR3 comprises the amino acid sequence of QQYNNWPPLT (SEQ ID NO: 8).

Provided below are two exemplary anti-CTLA-4 antibodies, Ab55h and Ab47, including their heavy chain and light chain CDR sequences (by Kabat definition) and heavy chain and light chain variable region sequences.

TABLE 1

Heavy chain CDR sequences of exemplary anti-CTLA-4 antibodies

| Exemplary Antibody | CDR1 | CDR2 | CDR3 |
|---|---|---|---|
| Ab55h | GDYYWG (SEQ ID NO: 15) | SIYHSGYTYYNPSLKL (SEQ ID NO: 16) | DSGWYVIAFDY (SEQ ID NO: 17) |
| Ab47 | NYGIH (SEQ ID NO: 18) | AIWYDGNNKYY-ADSVKD (SEQ ID NO: 19) | NGVLGAFDI (SEQ ID NO: 20) |

TABLE 2

Light chain CDR sequences of exemplary anti-CTLA-4 antibodies

| Exemplary antibody | CDR1 | CDR2 | CDR3 |
|---|---|---|---|
| Ab55H | RASQSVSSNLA (SEQ ID NO: 21) | GASTRAT (SEQ ID NO: 22) | QQYNNWPPLT (SEQ ID NO: 8) |
| Ab47 | RASQGISNYLA (SEQ ID NO: 23) | AASTLQS (SEQ ID NO: 24) | QKYNSSPWT (SEQ ID NO: 25) |

Heavy chain variable region sequence of Ab55h (CDRs in boldface):

(SEQ ID NO: 1)

QVQLQESGPGLVKPSETLSLTCAVSGYSISGDYYWGWIRQPPGKGLEWIG

SIYHSGYTYYNPSLKSRVTISVDTSKNQFSLKLSSVTAADTAVYYCARDS

GWYVIAFDYWGQGTLVTVSS

-continued

Light chain variable region of Ab55h:

(SEQ ID NO: 2)

EIVMTQSPATLSVSPGERATLSCRASQSVSSNLAWYQEKPGQAPRLLIYG

ASTRATGIPARFSGSGSGIEFTLTISSLQSEDFAVYYCQQYNNWPPLTFG

GGTKVEIK

Heavy chain variable region sequence of Ab47:

(SEQ ID NO: 26)

QVQLVESGGGVVQPGRSLRLSCAASGFTFSNYGIHWVRQAPGKGLEWVAA

IWYDGNNKYYADSVKDRFTISRDNSKNTLYLQMNSLRVEDTAVYYCARNG

VLGAFDIWGQGTMVTVSS

Light chain variable region sequence of Ab47:

(SEQ ID NO: 27)

DIQMTQSPSSLSASVGDRVTITCRASQGISNYLAWYQQKPGKVPKLLIYA

ASTLQSGVPSRFSGSGSGTDFTLTISSLQPEDVATYYCQKYNSSPWTFGQ

GTKVEIK

In some embodiments, the anti-CTLA-4 antibody described herein binds the same epitope in a CTLA-4 antigen as a reference antibody disclosed herein (e.g., Ab55h) or competes against the reference antibody from binding to the CTLA-4 antigen. An "epitope" refers to the site on a target compound that is bound by an antibody such as a Fab or full length antibody. An epitope can be linear, which is typically 6-15 amino acid in length. Alternatively, the epitope can be conformational. An antibody that binds the same epitope as a reference antibody described herein may bind to exactly the same epitope or a substantially overlapping epitope (e.g., containing less than 3 non-overlapping amino acid residue, less than 2 non-overlapping amino acid residues, or only 1 non-overlapping amino acid residue) as the reference antibody. Whether two antibodies compete against each other from binding to the cognate antigen can be determined by a competition assay, which is well known in the art. Such antibodies can be identified as known to those skilled in the art, e.g., those having substantially similar structural features (e.g., complementary determining regions), and/or those identified by assays known in the art. For example, competition assays can be performed using one of the reference antibodies to determine whether a candidate antibody binds to the same epitope as the reference antibody or competes against its binding to the CTLA-4 antigen.

In some embodiments, an anti-CTLA-4 antibody disclosed herein may comprise the same regions/residues responsible for antigen-binding as a reference antibody (e.g., Ab55h), such as the same specificity-determining residues in the CDRs or the whole CDRs. The regions/residues that are responsible for antigen-binding can be identified from amino acid sequences of the heavy chain/light chain sequences of the reference antibody (shown above) by methods known in the art. See, e.g., www.bioinforg.uk/abs; Almagro, J. Mol. Recognit. 17:132-143 (2004); Chothia et al., J. Mol. Biol. 227:799-817 (1987), as well as others known in the art or disclosed herein. Determination of CDR regions in an antibody is well within the skill of the art, for example, the methods disclosed herein, e.g., the Kabat method (Kabat et al. Sequences of Proteins of Immunological Interest, (5th ed., 1991, National Institutes of Health, Bethesda Md.)) or the Chothia method (Chothia et al., 1989, Nature 342:877; Al-lazikani et al (1997) J. Molec. Biol. 273:927-948)). As used herein, a CDR may refer to the CDR defined by any method known in the art. Two antibodies having the same CDR means that the two antibodies have the same amino acid sequence of that CDR as determined by the same method. In specific examples, the anti-CTLA-4 antibodies disclosed herein have the same $V_H$ and/or $V_L$ as a reference antibody, such as Ab55h.

Also within the scope of the present disclosure are functional variants of any of the exemplary anti-CTLA-4 antibodies as disclosed herein. A functional variant may contain one or more amino acid residue variations in the $V_H$ and/or $V_L$, or in one or more of the HC CDRs and/or one or more of the LC CDRs as relative to the reference antibody, while retaining substantially similar binding and biological activities (e.g., substantially similar binding affinity, binding specificity, inhibitory activity, anti-tumor activity, or a combination thereof) as the reference antibody.

In some examples, the anti-CTLA-4 antibody disclosed herein comprises a HC CDR1, a HC CDR2, and a HC CDR3, which collectively contains no more than 10 amino acid variations (e.g., no more than 9, 8, 7, 6, 5, 4, 3, 2, or 1 amino acid variation) as compared with the HC CDR1, HC CDR2, and HC CDR3 of a reference antibody such as Ab55h. "Collectively" means that the total number of amino acid variations in all of the three HC CDRs is within the defined range. Alternatively or in addition, the anti-CTLA-4 antibody may comprise a LC CDR1, a LC CDR2, and a LC CDR3, which collectively contains no more than 10 amino acid variations (e.g., no more than 9, 8, 7, 6, 5, 4, 3, 2 or 1 amino acid variation) as compared with the LC CDR1, LC CDR2, and LC CDR3 of the reference antibody.

In some examples, the anti-CTLA-4 antibody disclosed herein may comprise a HC CDR1, a HC CDR2, and a HC CDR3, at least one of which contains no more than 5 amino acid variations (e.g., no more than 4, 3, 2, or 1 amino acid variation) as the counterpart HC CDR of a reference antibody such as Ab55h. In specific examples, the antibody comprises a HC CDR3, which contains no more than 5 amino acid variations (e.g., no more than 4, 3, 2, or 1 amino acid variation) as the HC CDR3 of a reference antibody such as Ab55h. Alternatively or in addition, an anti-CTLA-4 antibody may comprise a LC CDR1, a LC CDR2, and a LC CDR3, at least one of which contains no more than 5 amino acid variations (e.g., no more than 4, 3, 2, or 1 amino acid variation) as the counterpart LC CDR of the reference antibody. In specific examples, the antibody comprises a LC CDR3, which contains no more than 5 amino acid variations (e.g., no more than 4, 3, 2, or 1 amino acid variation) as the LC CDR3 of the reference antibody.

In some instances, the amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. In some instances, conservative substitutions of amino acids may include substitutions made amongst amino acids within the following groups: (a) M, I, L, V; (b) F, Y, W; (c) K, R, H; (d) A, G; (e) S, T; (f) Q, N; and (g) E, D.

In further embodiments, the anti-CTLA-4 antibodies may include modifications to improve properties of the antibody, for example, stability, oxidation, isomerization and deamidation. For example, the Trp (W) residue in the HC CDR3 of Ab55h may be changed to Ala (A) or Ser (S) to minimize oxidation, the Asp-Ser (DS) dipeptide in the HC CDR3 of Ab55h may be changed to Glu-Ser (ES), Asp-Ala (DA), or Asp-Val (DV) to minimize Asp (D) isomerization, or the Gln-Ser (QS) dipeptide in the LC CDR1 of Ab55h may be changed to Ala-Ser (AS) or Ser-Ser (SS) to minimize deamidation. Further examples are known in the art, see e.g., ADME and Translational Pharmacokinetics/Pharmacodynamics of Therapeutic Proteins. Honghui Zhou, Frank-Peter Theil, ISBN: 978-1-118-89864-2, November 2015, page 18.

Exemplary variants of Ab55h are provided below:

TABLE 3

Heavy and light chain CDR sequences of Ab55h and Variants Thereof

| Name | CDR1 HC | CDR2 HC | CDR3 HC | CDR1 LC | CDR2 LC | CDR3 LC |
|---|---|---|---|---|---|---|
| Ab55h | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNNWPPLT (SEQ ID NO: 8) |
| Ab55h-PM1 | GDYYWN (SEQ ID NO: 28) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNNWPPLT (SEQ ID NO: 8) |
| Ab55h-PM2 | GDYYWG (SEQ ID NO: 15) | SIYHDGYTYYNPSLKS (SEQ ID NO: 31) | DSGWYVIAFDY (SEQ ID NO: 17) | RASQSVSSNLA (SEQ ID NO: 21) | GASTRAT (SEQ ID NO: 22) | QQYNNWPPLT (SEQ ID NO: 8) |
| Ab55h-PM3 | GDYYWG (SEQ ID NO: 15) | SIYHSAYTYYNPSLKS (SEQ ID NO: 32) | DSGWYVIAFDY (SEQ ID NO: 17) | RASQSVSSNLA (SEQ ID NO: 21) | GASTRAT (SEQ ID NO: 22) | QQYNNWPPLT (SEQ ID NO: 8) |
| Ab55h-PM4 | GDYYWG (SEQ ID NO: 15) | SIYHSGYTYYNPSVKS (SEQ ID NO: 33) | DSGWYVIAFDY (SEQ ID NO: 17) | RASQSVSSNLA (SEQ ID NO: 21) | GASTRAT (SEQ ID NO: 22) | QQYNNWPPLT (SEQ ID NO: 8) |
| Ab55h-PM5 | GDYYWG (SEQ ID NO: 15) | SIYHSGYTYYNPSLKS (SEQ ID NO: 16) | DSGWYVIAFAY (SEQ ID NO: 34) | RASQSVSSNLA (SEQ ID NO: 21) | GASTRAT (SEQ ID NO: 22) | QQYNNWPPLT (SEQ ID NO: 8) |

TABLE 3-continued

| Heavy and light chain CDR sequences of Ab55h and Variants Thereof | | | | | | |
|---|---|---|---|---|---|---|
| Name | CDR1 HC | CDR2 HC | CDR3 HC | CDR1 LC | CDR2 LC | CDR3 LC |
| Ab55h-PM6 | GDYYWG (SEQ ID NO: 15) | SIYHSGYTYYNPSLKS (SEQ ID NO: 16) | DSGWYVIAFDI (SEQ ID NO: 35) | RASQSVSSNLA (SEQ ID NO: 21) | GASTRAT (SEQ ID NO: 22) | QQYNNWPPLT (SEQ ID NO: 8) |
| Ab55h-PM7 | GDYYWG (SEQ ID NO: 15) | SIYHSGYTYYNPSLKS (SEQ ID NO: 16) | DSGWYVIAFDY (SEQ ID NO: 17) | RASQSISSNLA (SEQ ID NO: 49) | GASTRAT (SEQ ID NO: 22) | QQYNNWPPLT (SEQ ID NO: 8) |
| Ab55h-PM8 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | AASTRAT (SEQ ID NO: 53) | QQYNNWPPLT (SEQ ID NO: 8) |
| Ab55h-PM9 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GATTRAT (SEQ ID NO: 54) | QQYNNWPPLT (SEQ ID NO: 8) |
| Ab55h-PM10 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASSRAT (SEQ ID NO: 55) | QQYNNWPPLT (SEQ ID NO: 8) |
| Ab55h-PM11 | GDYYWG (SEQ ID NO: 15) | SIYHSGYTYYNPSLKS (SEQ ID NO: 16) | DSGWYVIGFDY (SEQ ID NO: 36) | RASQSVSSNLA (SEQ ID NO: 21) | GASTRAT (SEQ ID NO: 22) | QQYNNWPPLT (SEQ ID NO: 8) |
| Ab55h-PM12 | GDYYWG (SEQ ID NO: 15) | SIYHSGYTYYNPSLKS (SEQ ID NO: 16) | DSGWYVIAYDY (SEQ ID NO: 37) | RASQSVSSNLA (SEQ ID NO: 21) | GASTRAT (SEQ ID NO: 22) | QQYNNWPPLT (SEQ ID NO: 8) |
| Ab55h-PM13 | GDYYWG (SEQ ID NO: 15) | SIYHSGYTYYNPSLKS (SEQ ID NO: 16) | DVGWYVIAFDY (SEQ ID NO: 38) | RASQSVSSNLA (SEQ ID NO: 21) | GASTRAT (SEQ ID NO: 22) | QQYNNWPPLT (SEQ ID NO: 8) |
| Ab55h-PM14 | GDYYWG (SEQ ID NO: 15) | SIYHSGYTYYNPSLKS (SEQ ID NO: 16) | DSGFYVIAFDY (SEQ ID NO: 39) | RASQSVSSNLA (SEQ ID NO: 21) | GASTRAT (SEQ ID NO: 22) | QQYNNWPPLT (SEQ ID NO: 8) |
| Ab55h-PM15 | GDYYWG (SEQ ID NO: 15) | SIYHSGYTYYNPSLKS (SEQ ID NO: 16) | DSGAYVIAFDY (SEQ ID NO: 40) | RASQSVSSNLA (SEQ ID NO: 21) | GASTRAT (SEQ ID NO: 22) | QQYNNWPPLT (SEQ ID NO: 8) |
| Ab55h-PM16 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYANWPPLT (SEQ ID NO: 57) |
| Ab55h-PM17 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNVWPPLT (SEQ ID NO: 58) |
| Ab55h-PM18 | SDYYWG (SEQ ID NO: 29) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNNWPPLT (SEQ ID NO: 8) |
| Ab55h-PM19 | GDYYWG (SEQ ID NO: 15) | SIYHSGYTYYNPSLKS (SEQ ID NO: 16) | DSGWYVIAFDY (SEQ ID NO: 17) | RASQSVGSNLA (SEQ ID NO: 50) | GASTRAT (SEQ ID NO: 22) | QQYNNWPPLT (SEQ ID NO: 8) |
| Ab55h-PM20 | GDYYWG (SEQ ID NO: 15) | SIYHSGYTYYNPSLKS (SEQ ID NO: 16) | DSGWYVIAFDY (SEQ ID NO: 17) | RASQSVYSNLA (SEQ ID NO: 51) | GASTRAT (SEQ ID NO: 22) | QQYNNWPPLT (SEQ ID NO: 8) |
| Ab55h-PM21 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNNSPPLT (SEQ ID NO: 59) |
| Ab55h-PM22 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNNWPPIT (SEQ ID NO: 60) |
| Ab55h-PM23 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNNWPPFT (SEQ ID NO: 61) |
| Ab55h-PM24 | GDYYWG (SEQ ID NO: 15) | SIYHSGYTYYNPSLKS (SEQ ID NO: 16) | DVGWYVIAFDI (SEQ ID NO: 41) | RASQSVSSNLA (SEQ ID NO: 21) | GASTRAT (SEQ ID NO: 22) | QQYNNWPPLT (SEQ ID NO: 8) |

TABLE 3-continued

Heavy and light chain CDR sequences of Ab55h and Variants Thereof

| Name | CDR1 HC | CDR2 HC | CDR3 HC | CDR1 LC | CDR2 LC | CDR3 LC |
|---|---|---|---|---|---|---|
| Ab55h-PM25 | GDYYWG (SEQ ID NO: 15) | SIYHSGYTYYNPSLKS (SEQ ID NO: 16) | DVGFYVIAFDY (SEQ ID NO: 42) | RASQSVSSNLA (SEQ ID NO: 21) | GASTRAT (SEQ ID NO: 22) | QQYNNWPPLT (SEQ ID NO: 8) |
| Ab55h-PM26 | GDYYWG (SEQ ID NO: 15) | SIYHSGYTYYNPSLKS (SEQ ID NO: 16) | DVGFYVIAFDI (SEQ ID NO: 43) | RASQSVSSNLA (SEQ ID NO: 21) | GASTRAT (SEQ ID NO: 22) | QQYNNWPPLT (SEQ ID NO: 8) |
| Ab55h-PM27 | GDYYWG (SEQ ID NO: 15) | SIYHSGYTYYNPSLKS (SEQ ID NO: 16) | DSGFYVIAFDI (SEQ ID NO: 44) | RASQSVSSNLA (SEQ ID NO: 21) | GASTRAT (SEQ ID NO: 22) | QQYNNWPPLT (SEQ ID NO: 8) |
| Ab55h-PM28 | GDYYWG (SEQ ID NO: 15) | SIYHSGYTYYNPSLKS (SEQ ID NO: 16) | DSGWYVIGYDY (SEQ ID NO: 45) | RASQSVSSNLA (SEQ ID NO: 21) | GASTRAT (SEQ ID NO: 22) | QQYNNWPPLT (SEQ ID NO: 8) |
| Ab55h-PMR1 | GSYYWG (SEQ ID NO: 30) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNNWPPLT (SEQ ID NO: 8) |
| Ab55h-PM-R2 | GDYYWG (SEQ ID NO: 15) | SIYHSGYTYYNPSLKS (SEQ ID NO: 16) | GSGWYVIAFDY (SEQ ID NO: 46) | RASQSVSSNLA (SEQ ID NO: 21) | GASTRAT (SEQ ID NO: 22) | QQYNNWPPLT (SEQ ID NO: 8) |
| Ab55h-PM-R3 | GDYYWG (SEQ ID NO: 15) | SIYHSGYTYYNPSLKS (SEQ ID NO: 16) | DSGWYVIAFDY (SEQ ID NO: 17) | RASQSVSSYLA (SEQ ID NO: 52) | GASTRAT (SEQ ID NO: 22) | QQYNNWPPLT (SEQ ID NO: 8) |
| Ab55h-PM-R4 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAS (SEQ ID NO: 56) | QQYNNWPPLT (SEQ ID NO: 8) |
| Ab55h-PM-R5 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYGNWPPLT (SEQ ID NO: 62) |
| Ab55h-PM-R6 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQYNSWPPLT (SEQ ID NO: 63) |
| Ab55h-PM-R7 | GDYYWG (SEQ ID NO: 15) | SIYHSGYTYYNPSLKS (SEQ ID NO: 16) | ESGWYVIAFDY (SEQ ID NO: 47) | RASQSVSSNLA (SEQ ID NO: 21) | GASTRAT (SEQ ID NO: 22) | QQYNNWPPLT (SEQ ID NO: 8) |
| Ab55h-PM-R8 | GDYYWG (SEQ ID NO: 15) | SIYHSGYTYYNPSLKS (SEQ ID NO: 16) | DSGWYVIAFDY (SEQ ID NO: 17) | RASQSVSSNLA (SEQ ID NO: 21) | GASTRAT (SEQ ID NO: 22) | QQRNNWPPLT (SEQ ID NO: 64) |
| Ab55h-PM-R9 | GDYYWG (SEQ ID NO: 15) | SIYHSGYTYYNPSLKS (SEQ ID NO: 16) | DSGWSVIAFDY (SEQ ID NO: 48) | RASQSVSSNLA (SEQ ID NO: 21) | GASTRAT (SEQ ID NO: 22) | QQYNNWPPLT (SEQ ID NO: 8) |

In some embodiments, the anti-CTLA-4 antibody disclosed herein may comprise heavy chain CDRs that collectively are at least 80% (e.g., 85%, 90%, 95%, or 98%) identical to the heavy chain CDRs of a reference antibody such as Ab55h. Alternatively or in addition, the antibody may comprise light chain CDRs that collectively are at least 80% (e.g., 85%, 90%, 95%, or 98%) identical to the light chain CDRs of the reference antibody. In some embodiments, the anti-CTLA-4 antibody may comprise a heavy chain variable region that is at least 80% (e.g., 85%, 90%, 95%, or 98%) identical to the heavy chain variable region of a reference antibody such as Ab55h and/or a light chain variable region that is at least 80% (e.g., 85%, 90%, 95%, or 98%) identical to the light chain variable region of the reference antibody.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the heavy chain of any of the anti-CTLA-4 antibodies as described herein may further comprise a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4.

An exemplary human IgG1 constant region is given below:

(SEQ ID NO: 65)

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

The light chain of any of the anti-CTLA-4 antibodies described herein may further comprise a light chain constant region (CL), which can be any CL known in the art. In some examples, the CL is a kappa light chain. In other examples, the CL is a lambda light chain. Antibody heavy and light chain constant regions are well known in the art, e.g., those provided in the IMGT database (www.imgt.org) or at www.vbase2.org/vbstat.php., both of which are incorporated by reference herein.

When needed, the anti-CTLA-4 antibody as described herein may comprise a modified constant region. For example, it may comprise a modified constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

In some embodiments, the heavy chain constant region used in the anti-CTLA-4 antibodies described herein may comprise mutations (e.g., amino acid residue substitutions) to modulate (e.g., enhance or reduce) the ADCC activity. In some examples, the heavy chain constant region may comprise an amino acid residue mutation at one or more of positions E233, L234, L235, G236, A327, A330, and P331 (numbering according to the EU index) to reduce ADCC activity. The mutations may comprise E233P, L234V, L235A, deltaG236, A327G, A330S, P331S, or a combination thereof. In other examples, the heavy chain constant region may comprise an amino acid residue mutation at one or more of positions S298, E333, K334, M252, S254, and T256 (numbering according to the EU index) to enhance the ADCC activity. The amino acid residue mutations may comprise S298A, E333A, K334A, M252Y, S254T, T256E, or a combination thereof. In some instances, the heavy chain constant region of an anti-CTLA-4 antibody described herein may be from human IgG1 and comprises a mutation at position K214 (EU index numbering), for example, the K214R substitution.

In some embodiments, the heavy chain constant region used in the anti-CTLA-4 antibodies described herein may comprise mutations (e.g., amino acid residue substitutions) to enhance a desired characteristic of the antibody, for example, increasing the binding activity to the neonatal Fc receptor (FcRn) and thus the serum half-life of the antibodies. It was known that binding to FcRn is critical for maintaining antibody homeostasis and regulating the serum half-life of antibodies. One or more (e.g., 1, 2, 3, 4, 5, or more) mutations (e.g., amino acid residue substitutions) may be introduced into the constant region at suitable positions (e.g., in CH2 region) to enhance FcRn binding and enhance the half-life of the antibody.

Exemplary heavy chain and light chain amino acid sequences of the anti-CTLA-4 antibodies disclosed herein are provided below:

Heavy Chain Sequence Having VH of Ab55h and Human IgG1 Constant Region (K214R allotype)

(SEQ ID NO: 66)

QVQLQESGPGLVKPSETLSLTCAVSGYSISGDYYWGWIRQPPGKGLEWIG

SIYHSGYTYYNPSLKSRVTISVDTSKNQFSLKLSSVTAADTAVYYCARDS

GWYVIAFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

Heavy Chain Sequence Having VH of Ab47 and Human IgG1 Constant Region (SEQ ID NO: 67)

QVQLVESGGGVVQPGRSLRLSCAASGFTFSNYGIHWVRQAPGKGLEWVAA

IWYDGNNKYYADSVKDRFTISRDNSKNTLYLQMNSLRVEDTAVYYCARNG

VLGAFDIWGQGTMVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Light Chain Sequence Having VL of Ab55h and Human IgK Constant Region (SEQ ID NO: 68)

EIVMTQSPATLSVSPGERATLSCRASQSVSSNLAWYQEKPGQAPRLLIYG

ASTRATGIPARFSGSGSGTEFTLTISSLQSEDFAVYYCQQYNNWPPLTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Light Chain Sequence Having VL of Ab47 and Human IgK Constant Region (SEQ ID NO: 69)

DIQMTQSPSSLSASVGDRVTITCRASQGISNYLAWYQQKPGKVPKLLIYA

ASTLQSGVPSRFSGSGSGTDFTLTISSLQPEDVATYYCQKYNSSPWTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The present disclosure also provides germlined variants of any of the exemplary anti-CTLA-4 antibodies disclosed herein. A germlined variant contains one or more mutations in the framework regions as relative to its parent antibody towards the corresponding germline sequence. To make a germline variant, the heavy or light chain variable region sequence of the parent antibody or a portion thereof (e.g., a framework sequence) can be used as a query against an antibody germline sequence database (e.g., www.bioinfo.org.uk/abs/, www.vbase2.org, or www.imgt.org) to identify the corresponding germline sequence used by the parent antibody and amino acid residue variations in one or more of the framework regions between the germline sequence and the parent antibody. One or more amino acid substitutions can then be introduced into the parent antibody based on the germline sequence to produce a germlined variant. As described herein, the anti-CTLA-4 antibody can be in any antibody form, including, but not limited to, intact (i.e., full-length) antibodies, antigen-binding fragments thereof (such as Fab, Fab', F(ab')$_2$, Fv), single chain antibodies, bi-specific antibodies, or nanobodies.

Preparation of Anti-CTLA-4 Antibodies

Antibodies capable of binding CTLA-4 as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., CTLA-4) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-CTLA-4 monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the CTLA-4 activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or $R_1N{=}C{=}NR$, where R and $R_1$ are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of CTLA-4. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, CA) and HuMAb-Mouse® and TC Mouse™ from Medarex, Inc. (Princeton, NJ) or H2L2 mice from Harbour Antibodies BV (Holland). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, human HEK293 cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage or yeast scFv library and scFv clones specific to CTLA-4 can be identified from the library following routine procedures. Positive clones can be subjected to further screening to identify those that inhibit CTLA-4 activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In one example, epitope mapping can be accomplished use H/D-Ex (hydrogen deuterium exchange) coupled with proteolysis and mass spectrometry. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined.

The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the CTLA-4 polypeptide have been replaced (swapped) with sequences from a closely related, but antigenically distinct protein (such as CD-28 protein). By assessing binding of the antibody to the mutant CTLA-4, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art. In some examples, an anti-CTLA-4 antibody is prepared by recombinant technology as exemplified below.

Nucleic acids encoding the heavy and light chain of an anti-CTLA-4 antibody as described herein can be cloned into one expression vector, each nucleotide sequence being in operable linkage to a suitable promoter. In one example, each of the nucleotide sequences encoding the heavy chain and light chain is in operable linkage to a distinct promoter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the *Rous sarcoma* virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters (Brown, M. et al., Cell, 49:603-612 (1987)), those using the tetracycline repressor (tetR)(Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)). Other systems include FK506 dimer, VP16 or p65 using astradiol, RU486, diphenol murislerone, or rapamycin. Inducible systems are available from Invitrogen, Clontech and Ariad, among others.

Regulatable promoters that include a repressor with the operon can be used. In one embodiment, the lac repressor from *E. coli* can function as a transcriptional modulator to regulate transcription from lac operator-bearing mammalian cell promoters (M. Brown et al., Cell, 49:603-612 (1987)); Gossen and Bujard (1992); (M. Gossen et al., Natl. Acad. Sci. USA, 89:5547-5551 (1992)) combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-CTLA-4 antibody, as also described herein. The recombinant expression vector can be introduced into a suitable host cell (e.g., a dhfr-CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-CTLA-4 antibody and the other encoding the light chain of the anti-CTLA-4 antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-CTLA-4 antibody as described herein, vectors (e.g., expression vectors) containing such; and host cells comprising the vectors are within the scope of the present disclosure.

Pharmaceutical Compositions

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. “Acceptable” means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In other examples, the pharmaceutical composition described herein can be formulated in a sustained release format, which affects binding selectively to tissue or tumors by implementing certain protease biology technology, for example, by peptide masking of the antibody's antigen binding site to allow selective protease cleavability by one or multiple proteases in the tumor microenvironment, such as Probody™ or Conditionally Active Biologics™. An activation may be formulated to be reversible in a normal microenvironment.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation. For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Chimeric Antigen Receptor (CAR) and Immune Cells Expressing Such

The present disclosure also features chimeric antigen receptors targeting CTLA-4 and immune cells expressing such. Chimeric antigen receptors (CARs) as disclosed herein are artificial cell-surface receptors that redirect binding specificity of immune cells (e.g., T cells) expressing such to CTLA-4$^+$ cells, thereby eliminating the target cells via, e.g., the effector activity of the immune cells. A CAR construct often comprises an extracellular antigen binding domain fused to at least an intracellular signaling domain. Cartellieri et al., J Biomed Biotechnol 2010:956304, 2010. The extracellular antigen binding domain, which can be a single-chain antibody fragment (scFv), is specific to a CTLA-4 antigen and the intracellular signaling domain can mediate a cell signaling that lead to activation of immune cells. As such, immune cells expressing a CAR construct specific to CTLA-4 can bind to target cells expressing CTLA-4, leading to activation of the immune cells and elimination of the target cells.

Any of the anti-CTLA-4 antibodies described herein can be used to produce the CAR constructs also described herein. For example, the $V_H$ and $V_L$ domains of an anti-CTLA-4 antibody can be fused to the intracellular signaling domain(s) to produce a CAR construct using the conventional recombinant technology. In some examples, the $V_H$ and $V_L$ domains of an anti-CTLA-4 are connected via a peptide linker to form a scFv fragment.

The CAR construct disclosed herein may comprise one or more intracellular signaling domains. In some examples, CAR comprises an intracellular signaling domain that includes an immunoreceptor tyrosine-based activation motif (ITAM). Such an intracellular signaling domain may be from CD3ζ. In addition, the CAR construct may further comprise one or more co-stimulatory signaling domains, which may be from a co-stimulatory receptor, for example, from 4-1BB (CD137), CD28, CD40, OX40, or ICOS.

The CAR construct disclosed herein may further comprise a transmembrane-hinge domain, which can be obtained from a suitable cell-surface receptor, for example, CD28 or CD8.

Also provided are isolated nucleic acid molecules and vectors encoding any of the anti-CTLA-4 CARs as disclosed herein, and host cells, such as host immune cells (e.g., T cells and natural killer cells), comprising the nucleic acid molecules or vectors. Immune cells expressing anti-CTLA-4 CARs, which comprises a CTLA-4-specific antibody binding fragment, can be used for the treatment of diseases mediated by CTLA-4$^+$ cells.

Therapeutic Applications

Any of the antibodies, as well as the encoding nucleic acids or nucleic acid sets, vectors comprising such, or host cells comprising the vectors, described herein are useful for treating cancer, inflammation, infectious diseases, or other malignancies requiring stimulation of the immune response.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having cancer, an inflammatory disorder, an infectious disease (e.g., caused by bacteria or virus), or other malignancies requiring stimulation of the immune response. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

The methods and compositions described herein may be used to treat cancer. Examples of cancers that may be treated with the methods and compositions described herein include, but are not limited to: lung cancer, melanoma, renal cancer, liver cancer, myeloma, prostate cancer, breast cancer, colorectal cancer, gastric cancer, pancreatic cancer, thyroid cancer, hematological cancer, lymphoma, leukemia, skin cancer, ovarian cancer, bladder cancer, urothelial carcinoma, head and neck cancer, metastatic lesion(s) of the cancer, and all types of cancer which are diagnosed for high mutational burden. In a particular embodiment, the cancer has a high mutation burden. Subjects having or at risk for various cancers can be identified by routine medical procedures.

In some examples, the human patient has microsatellite instability-high (MSI-H) or mismatch repair deficient (dMMR), found in soft tissue cancer, glioblastoma, esophageal and EGJ carcinoma, breast carcinoma, non-small cell lung cancer, ovarian surface epithelial carcinomas, cancer of unknown primary, small cell lung cancer, non-epithelial ovarian cancer, pancreatic adenocarcinoma, other female genital tract malignancies, uveal melanoma, retroperitoneal or peritoneal sarcoma, thyroid carcinoma, uterine sarcoma, cholangiocarcinoma, prostate adenocarcinoma, hepatocellular carcinoma, neuroendocrine tumors, cervical cancer, colorectal adenocarcinoma, small intestinal malignancies, gastric adenocarcinoma and endometrial cancer.

As used herein, "an effective amount" refers to the amount of each active agent required to confer therapeutic effect on the subject, either alone or in combination with one or more other active agents. In some embodiments, the therapeutic effect is reduced CTLA-4 activity, increased numbers of activated effector T cells, and/or reduced numbers or activity of regulatory T cells. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily, weekly, every two weeks, or every three weeks dosage might range from about any of 0.1 μg/kg to 3 μg/kg to 30 μg/kg to 100 μg/kg to 300 μg/kg to 0.6 mg/kg, 1 mg/kg, 3 mg/kg, to 10 mg/kg, to 30 mg/kg to 100 mg/kg or more, depending on the factors mentioned above. For repeated administrations over several days, weeks, months, or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 3 mg/kg every 3 weeks, followed by a maintenance dose of about 1 mg/kg of the antibody once in 6 weeks, or followed by a maintenance dose of about 1 mg/kg every 3 weeks. However, other dosage regimens may be useful, depending on the pattern of pharmacokinetic decay that the practitioner wishes to achieve. For example, dosing of 1 mg/kg once in every 3 weeks in combination treatment with at least one additional immune therapy agent is contemplated. In some embodiments, dosing ranging from about 3 μg/mg to about 3 mg/kg (such as about 3 μg/mg, about 10 μg/mg, about 30 μg/mg, about 100 μg/mg, about 300 μg/mg, about 1 mg/kg, and about 3 mg/kg) may be used. In some embodiments, dosing frequency is once every week, every 2 weeks, every 3 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.1 to 5.0 mg/kg may be administered. In some examples, the dosage of the anti-CTLA-4 antibody described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an antibody, until a dosage is reached that achieves the desired result. In some embodiments, the desired result is a reduction of the size of the tumor, increased progression-free survival period and/or overall survival. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder. Alleviating a target disease/disorder includes delaying the development or progression of the disease, or reducing disease severity.

Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the antibodies described herein are administered to a subject in need of the treatment at an amount sufficient to inhibit the activity of the target antigen by at least 20% (e.g., 30%, 40%, 50%, 60%, 70%, 80%, 90% or greater) in vivo. In other embodiments, the antibody is administered in an amount effective in reducing the activity level of a target antigen by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered parenterally, topically, orally, by inhalation spray, rectally, nasally, buccally, vaginally or via an implanted reservoir. The term "parenteral" as used herein includes subcutaneous, intracutaneous, intravenous, intraperitoneal, intratumor, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution. In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods and Applications of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history.

In some embodiments, more than one antibody, or a combination of an antibody and another suitable therapeutic agent, may be administered to a subject in need of the treatment. The antibody can also be used in conjunction with other agents that serve to enhance and/or to complement the effectiveness of the agents.

Treatment efficacy for a target disease/disorder can be assessed by methods well-known in the art.

The anti-CTLA-4 antibody and treatment methods involving such as described in the present disclosure may be utilized in conjunction with other types of therapy for the target disease or disorder disclosed herein. Examples include chemotherapy, immune therapy (e.g. therapies involving therapeutic antibodies, antibodies, CAR T cells, or cancer vaccines), surgery, radiation, gene therapy, and so forth, or anti-infection therapy. Such therapies can be administered simultaneously or sequentially (in any order) with the treatment according to the present disclosure. In some instance, the target disease is cancer (e.g., those disclosed herein) and the conjunction therapy involves an immune checkpoint (e.g., inhibitory checkpoint) antagonist. Examples include PD-1/PD-L1 antagonists (e.g., nivolumab, pembrolizumab, avelumab, durvalumab and atezolizumab), LAG3 antagonists, TIM-3 antagonists, VISTA antagonists, TIGIT antagonists, CSF1R antagonists, CD112R (PVRIG) antagonists, PVR (CD155) antagonists, PD-L2 antagonists, A2AR antagonists, B7-H3 antagonists, B7-H4 antagonists or BTLA antagonists. Additional examples include activators that enhance the activity of stimulatory checkpoint such as CD122 (IL2) agonist, 4-1BB, ICOS ligand, GITR, and OX40.

Additional useful agents see also Physician's Desk Reference, 59.sup.th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

When co-administered with an additional therapeutic agent, suitable therapeutically effective dosages for each agent may be lowered due to the additive action or synergy.

The efficacy of the methods described herein may be assessed by any method known in the art and would be evident to a skilled medical professional. For example, the efficacy of the antibody-based immunotherapy may be assessed by survival of the subject or cancer burden in the subject or tissue or sample thereof. In some embodiments, the antibody based immunotherapy is assessed based on the safety or toxicity of the therapy in the subject, for example by the overall health of the subject and/or the presence of adverse events or severe adverse events.

Diagnostic Applications

Any of the anti-CTLA-4 antibodies disclosed herein can also be used for detecting presence of CTLA-4 (e.g., CTLA-4+ cells) in vitro or in vivo. Results obtained from such detection methods can be used for diagnostic purposes (e.g., diagnosing diseases associated with CTLA-$4^+$ cells) or for scientific research purposes (e.g., studying bioactivity and/or regulation of CTLA-$4^+$ cells).

For assay uses such as diagnostic uses, an anti-CTLA-4 antibody as described herein may be conjugated with a detectable label (e.g., an imaging agent such as a contrast agent) for detecting presence of CTLA-4 (e.g., CTLA-$4^+$ cells), either in vivo or in vitro. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

In one example, an anti-CTLA-4 antibody as described herein can be attached to a detectable label, which is a compound that is capable of releasing a detectable signal, either directly or indirectly, such that the aptamer can be detected, measured, and/or qualified, in vitro or in vivo. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the aptamer, directly or indirectly, by conventional methods.

In some embodiments, the detectable label is an agent suitable for imaging CTLA-$4^+$ cells in vivo, which can be a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99m}$Tc Mebrofenin, and $^{99m}$Tc Red Blood Cells, $^{123}$I Sodium iodide, $^{99m}$Tc Exametazime, $^{99m}$Tc Macroaggregate Albumin, $^{99m}$Tc Medronate, $^{99m}$Tc Mertiatide, $^{99}$Tc Oxidronate, $^{99m}$Tc Pentetate, $^{99m}$Tc Pertechnetate, $^{99m}$Tc Sestamibi, $^{99m}$Tc Sulfur Colloid, $^{99m}$Tc Tetrofosmin, Thallium-201, and Xenon-133. The reporting agent can also be a dye, e.g., a fluorophore, which is useful in detecting a disease mediated by CTLA-$4^+$ cells in tissue samples.

To perform a diagnostic assay in vitro, an anti-CTLA-4 antibody can be brought in contact with a sample suspected of containing CTLA-4, e.g., CTLA-4$^+$ cells. The antibody and the sample may be incubated under suitable conditions for a suitable period to allow for binding of the antibody to the CTLA-4 antigen. Such an interaction can then be detected via routine methods, e.g., ELISA histological staining or FACS.

To perform a diagnostic assay in vivo, a suitable amount of anti-CTLA-4 antibodies, conjugated with a label (e.g., an imaging agent or a contrast agent), can be administered to a subject in need of the examination. Presence of the labeled antibody can be detected based on the signal released from the label by routine methods.

Kits for Therapeutic and Diagnostic Applications

The present disclosure also provides kits for the therapeutic or diagnostic applications as disclosed herein. Such kits can include one or more containers comprising an anti-CTLA-4 antibody, e.g., any of those described herein.

In some embodiments, the kit can comprise instructions for use in accordance with any of the methods described herein. The included instructions can comprise a description of administration of the anti-CTLA-4 antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-CTLA-4 antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder treatable by stimulating immune responses, such as cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CTLA-4 antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

Also provided herein are kits for use in detecting CTLA-4$^+$ cells in a sample. Such a kit may comprise any of the anti-CTLA-4 antibodies described herein. In some instances, the anti-CTLA-4 antibody can be conjugated with a detectable label as those described herein. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

Alternatively or in addition, the kit may comprise a secondary antibody capable of binding to anti-CTLA-4 antibody. The kit may further comprise instructions for using the anti-CTLA-4 antibody for detecting CTLA-4$^+$ cells.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Identification and Characterization of Anti-CTLA-4 Antibodies

Antibodies capable of binding to human CTLA-4 were isolated via a hybridoma screen of mice. Various binding and biological features of the antibodies were tested and compared with control anti-CTLA-4 antibodies ipilimumab and tremelimumab and those having superior binding and biological activities relative to one or both of the control antibodies, e.g., Ab55h as disclosed herein, were identified.

Anti-CTLA-4 Antibody Binding Kinetics

The kinetic parameters of Ab55h, Ab47h, and control antibody ipilimumab were assessed using Surface Plasmon Resonance (SPR) technology with a Biacore T100 instrument. To test binding, a CM5 series S chip was loaded with a human antibody capture antibody and then Ab55h or ipilimumab were bound to the chip. Recombinant human CTLA-4-his (Sino Biologicals, 11159-H08H) was added in a serial 2-fold dilution, starting at a concentration of 500 nM. Since both antibodies displayed strong binding, the dissociation time was set for 20 minutes. The measurement was corrected using the baseline channel and the protein-antibody interaction was measured by the change in surface resonance and quantified with Biacore T100 control software (version 2.0.4). The resulting kinetic parameters are tabulated in Table 4 below. In particular, it was found that Ab55h has an 8.1-fold lower Kd value than the Ipilimumab, indicating that Ab55h possesses increased binding affinity compared to the reference antibody.

TABLE 4

Kinetic Parameters of Ab55h and ipilimumab

| Antibody | $K_{on}$ (M/sec) | $K_{off}$ (1/sec) | Kd (M) |
|---|---|---|---|
| Ab55h | 712,620 | 0.0006 | $8.6 \times 10^{-10}$ |
| Ab47h | 157,806 | 0.0015 | $1 \times 10^{-8}$ |
| Ipilimumab | 112,885 | 0.0008 | $7 \times 10^{-9}$ |
| Ratio Ipilimumab:Ab55h | 0.16X | 1.3X | 8.1X |

Antibody Binding to Human CTLA-4 on Cell Surface

To test the binding of antibodies to CTLA-4 under more physiological conditions, the binding of CTLA-4 antibodies to cell-surface CTLA-4 was tested. HEK293 cells were stably transfected with plasmids encoding human CTLA-4 and a stable cell line expressing high levels of hCTLA-4 was obtained. The surface expression of hCTLA-4 in the obtained cell line was tested using a commercial anti-CTLA-4 antibody and compared to the parent cell line (HEK293 without transfection). The hCLTLA4 cell line showed an approximate 40-fold increase in binding, as evidenced by flow cytometry. The hCTLA-4 binding of Ab55h was then compared to an isotype control antibody and two control anti-CTLA4 antibodies, ipilimumab and tremelimumab replicas. The anti-CTLA-4 antibodies were incubated in serial dilution concentrations with the HEK293-hCTLA-4 cells for 1 hour on ice. Following a wash step, an anti-human antibody conjugated to ALEXA FLUOR® 647® was added for an additional hour. The cells were washed, and propidium iodide (PI) was added to exclude dead cells. The fluorescent signal was measured using FACS and analyzed. Dead cells were removed based on the PI signal. The population was gated based on forward and side scatter (FSC and SSC) parameters, and doublets were removed. The Median Fluorescent Intensity (MFI) of the appropriate channel was calculated for the live single cells from each group. The MFI was plotted versus antibody concentration in Prism software (V6.01) and kinetic parameters were obtained using a curve fit dose response function with four parameters. The experiment was performed in triplicate and the results are shown in FIG. 1 and Table 5. A plot of the antibodies' binding is shown in FIG. 1 and the $EC_{50}$ values for the tested antibodies are given in Table 5. Ab55h was found to have 6.1-fold and 7.5-fold lower $EC_{50}$ values compared to the ipilimumab and tremelimumab replicas, respectively. The lower $EC_{50}$ values indicate increased binding affinity to cell surface hCTLA-4.

TABLE 5

Experimentally-determined $EC_{50}$ Values

| Antibody | $EC_{50}$ (95% CI) |
|---|---|
| Ab55h | 0.24 nM (0.15-0.39) |
| Ipilimumab | 1.47 nM (1.02-2.11) |
| Ratio Ab55h Ipilimumab:Ab55h | 6.1X |
| Tremelimumab | 1.79 nM (1.25-2.56) |
| Ratio Ab55h Tremelimumab:Ab55h | 7.5X |

The inhibitory activity of the Ab55h variants disclosed in Table 3 above was also determined by the same assay noted above. For example, certain Ab55h variants (e.g., PM1-PM28) all showed certain levels of blocking capabilities to CTLA-4 expressing cells as determined by FACS. The $EC_{50}$ values of certain variants are provided in Table 6 below.

TABLE 6

$EC_{50}$ Values of Ab55h Variants

| Name | EC50 binding (nM) | Range |
|---|---|---|
| Ab55h | 0.17 | 0.1038 to 0.2639 |
| Ab55h-PM1 | 0.27 | 0.1966 to 0.3689 |
| Ab55h-PM2 | 0.52 | 0.4237 to 0.6431 |
| Ab55h-PM3 | 0.42 | 0.3547 to 0.5015 |
| Ab55h-PM4 | 0.39 | 0.3078 to 0.4872 |
| Ab55h-PM5 | 0.24 | 0.1871 to 0.3122 |
| Ab55h-PM6 | 0.15 | 0.1007 to 0.2243 |
| Ab55h-PM7 | 0.18 | 0.1115 to 0.2863 |
| Ab55h-PM8 | 0.16 | 0.08789 to 0.2786 |
| Ab55h-PM9 | 0.26 | 0.1849 to 0.3571 |
| Ab55h-PM10 | 0.24 | 0.1500 to 0.3895 |
| Ab55h-PM11 | 0.21 | 0.1432 to 0.3051 |
| Ab55h-PM12 | 0.24 | 0.1798 to 0.3104 |
| Ab55h-PM13 | 0.22 | 0.1502 to 0.3334 |
| Ab55h-PM14 | 0.32 | 0.2044 to 0.4989 |
| Ab55h-PM15 | 0.32 | 0.1617 to 0.6144 |
| Ab55h-PM16 | 0.27 | 0.1899 to 0.3699 |
| Ab55h-PM17 | 0.31 | 0.2430 to 0.4055 |
| Ab55h-PM18 | 0.21 | 0.1853 to 0.2414 |
| Ab55h-PM19 | 0.12 | 0.06710 to 0.2146 |
| Ab55h-PM20 | 0.19 | 0.07822 to 0.4758 |
| Ab55h-PM21 | 0.22 | 0.07903 to 0.6365 |
| Ab55h-PM22 | 0.09 | 0.05100 to 0.1441 |
| Ab55h-PM23 | 0.22 | 0.06486 to 0.7225 |
| Ab55h-PM24 | 0.20 | 0.1001 to 0.3916 |
| Ab55h-PM25 | 0.34 | 0.2062 to 0.5619 |
| Ab55h-PM26 | 0.35 | 0.2195 to 0.5643 |
| Ab55h-PM27 | 0.20 | 0.1553 to 0.2690 |
| Ab55h-PM28 | 0.31 | 0.08194 to 1.171 |

Dimer/Monomer CTLA-4 Binding and Non-Linear Epitope hCTLA-4 can exist in monomer and dimer forms on the cell surface. In order to evaluate Ab55h's ability to recognize and bind to both CTLA-4 forms, an ELISA assay was performed. CTLA-4-his (Sino Biological) was run on a non-reducing gel and found to be in a dimer form. The recombinant protein was incubated for 10 minutes with 100 mM DTT to reduce the protein to its monomeric form. The reduced and non-reduced proteins were then coated onto a maxisorp plate (Nunc) and the binding of Ab55h was tested. The plates were coated overnight at 4° C., followed by a wash step and blocking with 20% milk for 1 hour at 37° C.

Figure 2A:
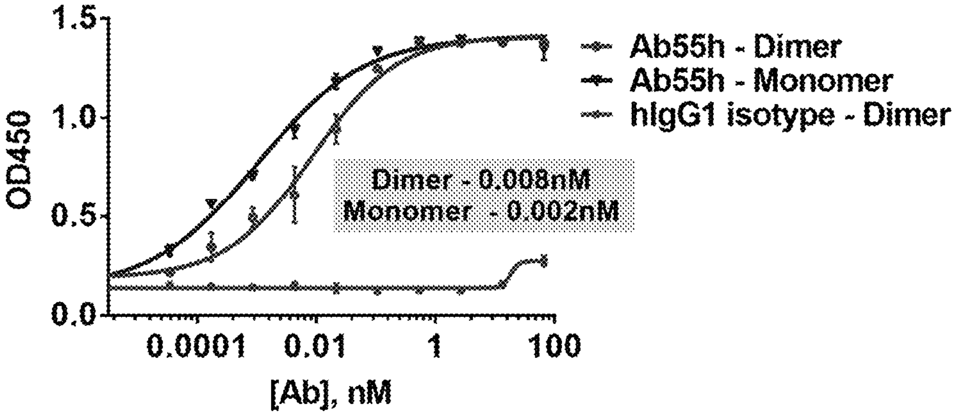
FIGS. 2A-2B include graphs showing binding activity to dimer and monomer CTLA-4.

Ab55h and the to hIgG1 control antibody were added to the plate in a serial dilution and incubated at room temperature for 1 hour. The plate was washed and a secondary anti-human-HRP antibody (Jackson) was added at a 1:5000 dilution. A TMB solution was added, followed by stop solution and the OD at 450 nm was measured. Data was analyzed with Prism software. Ab55h was found to bind both forms of CTLA-4, although an increased affinity was seen for the monomer form (FIG. 2A).

Figure 2B:
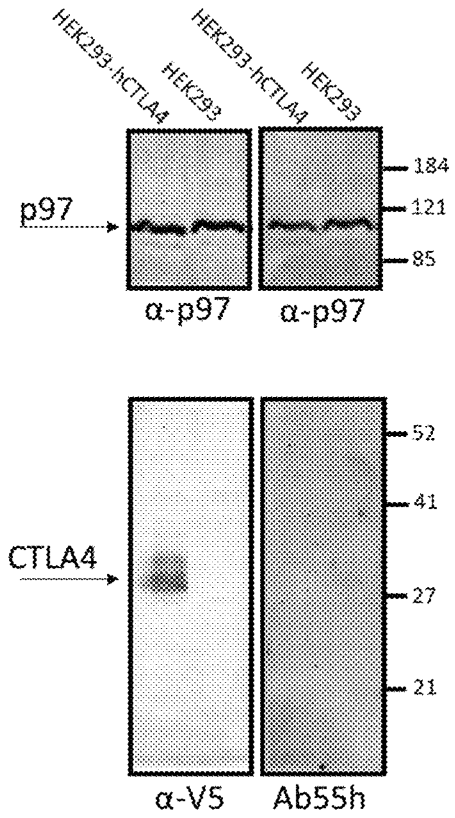

The ability of Ab55h to bind hCTLA-4 in a denatured form was tested using a Western blot. HEK293-hCTLA-4 cells that overexpress hCTLA-4 with an N-terminal V5 tag were lysed, boiled with sample buffer, and loaded on a 12% SDS-acrylamide gel. The membrane was blotted with anti-V5 antibody, to ensure CTLA-4 expression, and with Ab55h. p97 antibody was used as a loading control. It was observed that Ab55h did not bind the denatured hCTLA-4 in the assay (FIG. 2B), in contrast to the high affinity binding measured using the ELISA (FIG. 2A), SPR (Table 1) and cell surface binding (FIG. 1).

Binding Specificity

As many immune modulators have similar structure and some share ligand binding, it is important that antibodies bind specifically to their target and not to off-targets. Ab55h was tested to ensure it specifically only binds to CTLA-4. HEK293 cells were transfected with expression vectors of the following immune-related proteins: hBTLA, hICOS, hCD28, hPDL1, hPD1, hPDL2, and hCTLA-4. Over-expression of the proteins was verified using commercial antibodies against each target. The over-expressing cells were incubated with Ab55h or with control antibody ipilimumab replica, followed by incubation with an anti-human labeled secondary antibody. Antibody binding to cells was then detected using flow cytometry. Cells that were incubated only with the secondary antibody were used as a background control. Table 7 summarizes the MFI values for the different antibodies for each protein tested. Table 8 is a binary summary of the binding results. Note that "+" indicates binding above the background level and "-" indicate no binding as compared to the background level. Ab55h and ipilimumab were found to bind specifically to hCTLA-4 and not to any of the other tested immune modulator proteins.

TABLE 7

Mean Fluorescence Intensity (MFI) Values for Antibodies Binding to Indicated Proteins

| | hCTLA-4 | hBTLA | hICOS | hCD28 | hPDL1 | hPDL2 | hPD1 |
|---|---|---|---|---|---|---|---|
| Ab55h | 3,292 | 68 | 67 | 66 | 69 | 70 | 72 |
| Ipilimumab replica | 2,469 | 67 | 67 | 67 | 70 | 73 | 77 |
| Positive control (Commercial) | 2,827 | 1,664 | 19,196 | 22,053 | 39,074 | 58,058 | 12,363 |
| Secondary Antibody only | 78 | 82 | 67 | 69 | 68 | 71 | 74 |

TABLE 8

Binary Summary of Binding Results

| | CTLA-4 | BTLA | ICOS | CD28 | PDL1 | PDL2 | PD1 |
|---|---|---|---|---|---|---|---|
| Ab55h | + | – | – | – | – | – | – |
| Ipilimumab replica | + | – | – | – | – | – | – |
| Positive control (Commercial) | + | + | + | + | + | + | + |

Binding Curve of Antibodies to HEK293-CTLA-4 Cells

Figure 3A:
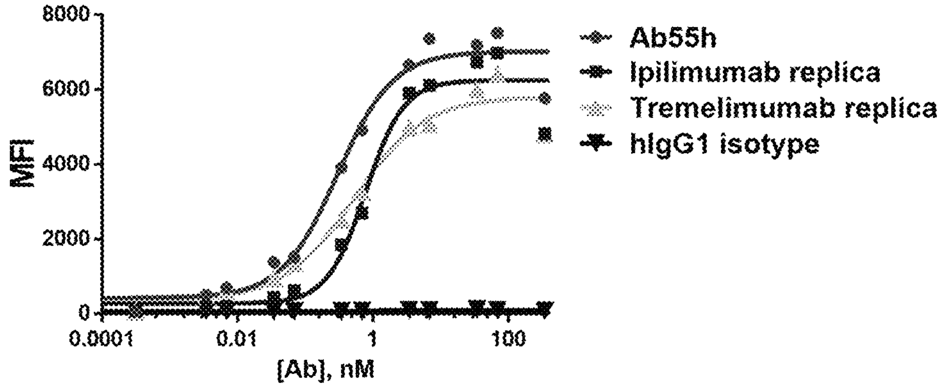
FIGS. 3A-3C are graphs showing the binding affinity of different species' CTLA-4.
Figure 3B:
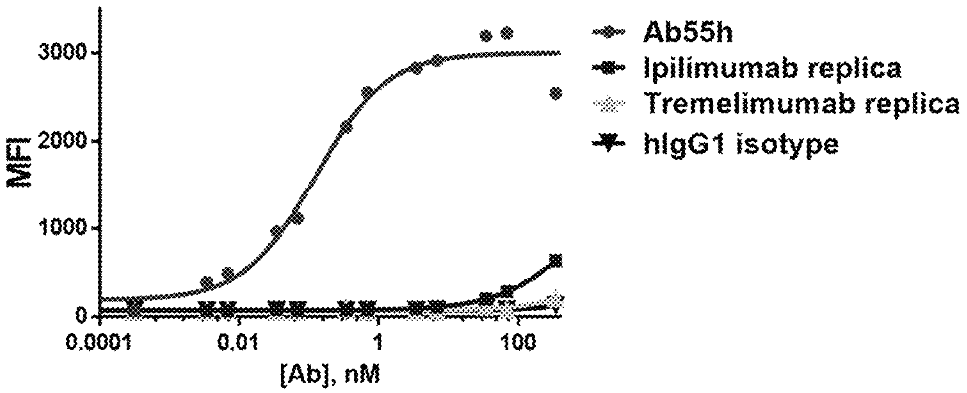
Figure 3C:
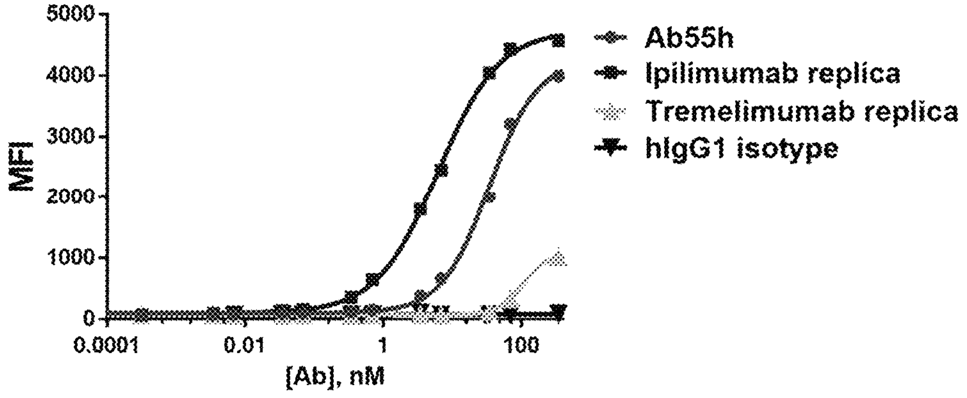

The ability of Ab55h and control antibodies ipilimumab and tremelimumab to bind CTLA-4 of different species was tested. Macaque (*Macaca fascicularis*), pig (*Sus scrofa*) and mouse (*Mus musculus*) CTLA-4 proteins were transiently expressed on the surface of HEK293 cells. Cells were incubated with Ab55h, ipilimumab and tremelimumab replicas, or an hIgG1 isotype control antibody in a serial dilution. Binding was measured using FACS and analyzed. Binding curves for CTLA-4 antibodies are shown for macaque (FIG. 3A), pig (FIG. 3B), and mouse (FIG. 3C) CTLA-4. Table 9 shows the $EC_{50}$ of the antibody to the different CTLA-4 proteins. The binding of antibodies to macaque CTLA-4 was found to be very similar to human CTLA-4, as expected due to a high similarity between the proteins. In contrast, pig CTLA-4 was bound by Ab55h with high affinity, while the ipilimumab and tremelimumab control antibodies showed very low levels of binding. This result indicates a difference in the binding epitope between Ab55h and the other CTLA-4 antibodies. Binding of Ab55h and ipilimumab to mouse CTLA-4 was found to be significantly weaker than binding to human CTLA-4. Tremelimumab was found to have the lowest affinity to mouse CTLA-4.

Further, the ability of Ab55h variants noted in Table 3 above to bind HEK293 cells overexpressing human CTLA-4 was tested. HEK293 cells were prepared as described above. Cells were incubated with Ab55h, an Ab55h variant, or an hIgG1 isotype control antibody in a serial dilution. Binding was measured using FACS. Binding curves for the different Ab55h variants shown in Table 3 are shown in FIGS. 13A-13D. Certain Ab55h variant antibodies (e.g., PM1-PM28) were found to have similar binding affinities to those of Ab55h. See, e.g., FIG. 13A-13C.

TABLE 9

| EC$_{50}$ Values of the Antibodies for Binding to CTLA-4 of Different Species | | | |
|---|---|---|---|
| Antibody | Macaque EC$_{50}$ | Pig EC$_{50}$ | Mouse EC$_{50}$ |
| Ab55h | 0.3 nM (0.15-0.57) | 0.12 nM (0.06-0.26) | 34 nM (28-42) |
| Ipilimumab | 0.78 nM (0.41-1.5) | 671 nM (335-1,342) | 6.1 nM (5.4-7) |
| Ratio:Ab55h-Ipilimumab:Ab55h | 2.6x | 5,591x | 0.18x |
| Tremelimumab | 0.52 nM (0.23-1.2) | ND | 105 nM (99-111) |
| Ratio Ab55h-Tremelimumab:Ab55h | 1.7x | ND | 3x |

Competitive Binding

The binding of Ab55r to HEK293-hCTLA-4-expressing cells was measured in the presence of ipilimumab or tremelimumab replicas in competition assays. Ab55r is an antibody composed of the variable domain of Ab55h and a rat IgG2b constant region. The rat form was used in this experiment to allow the simultaneous measurement of two antibodies' binding to cells. The comparison was measured in two assays: by increasing the dose of Ab55r in the presence of a fixed saturated dose of ipilimumab or tremelimumab, or by increasing the dose of ipilimumab or tremelimumab in the presence of a fixed saturated dose of Ab55r. In addition, assays exploring the competition of ipilimumab vs. tremelimumab up to 100-fold excess dose, as well as Ab55r vs. Ab55h, were performed as controls.

The resulting cell-based analysis revealed a symmetric displacement in the control experiments compared to an asymmetric displacement when Ab55r was competing with the other antibodies, ipilimumab or tremelimumab. This demonstrated that Ab55r can remove ipilimumab or tremelimumab from hCTLA-4, while ipilimumab and tremelimumab are unable to completely remove Ab55r, even at a 100-fold molar excess dose.

An additional type of analysis focused on the antibodies bound to each cell. In an equal concentration of each antibody (1.0 ug/ml), the percentage of cells bound by Ab55r was significantly larger than the percentage of cells bound by ipilimumab. When the Ab55r concentration was one-tenth that of ipilimumab (either 0.1 ug/ml versus 1 ug/ml and 1 ug/ml versus 10 ug/ml), most cells were bound by both antibodies. Even when the Ab55r concentration was one-hundredth that of ipilimumab (0.1 ug/ml versus 1 ug/ml), approximately 50% of the cells were still bound by both antibodies. However, the reverse is not true. When ipilimumab concentration was one-tenth of that of Ab55, nearly all of the cells were bound solely by Ab55r. Similar results were obtained when Ab55r was tested against tremelimumab, although the differences were smaller.

Similarly, when the fluorescence signal for each antibody was examined during the assays, it was clear that an increasing concentration of Ab55r decreased the binding of tremelimumab and ipilimumab significantly, but not vice versa.

Example 2: In Vitro Bioactivities of Anti-CTLA-4 Antibodies

This example investigates various in vitro bioactivities of the anti-CTLA-4 antibodies described herein.

Blocking of CTLA-4-CD80/86 Interaction on Cell Surface

Figure 4A:
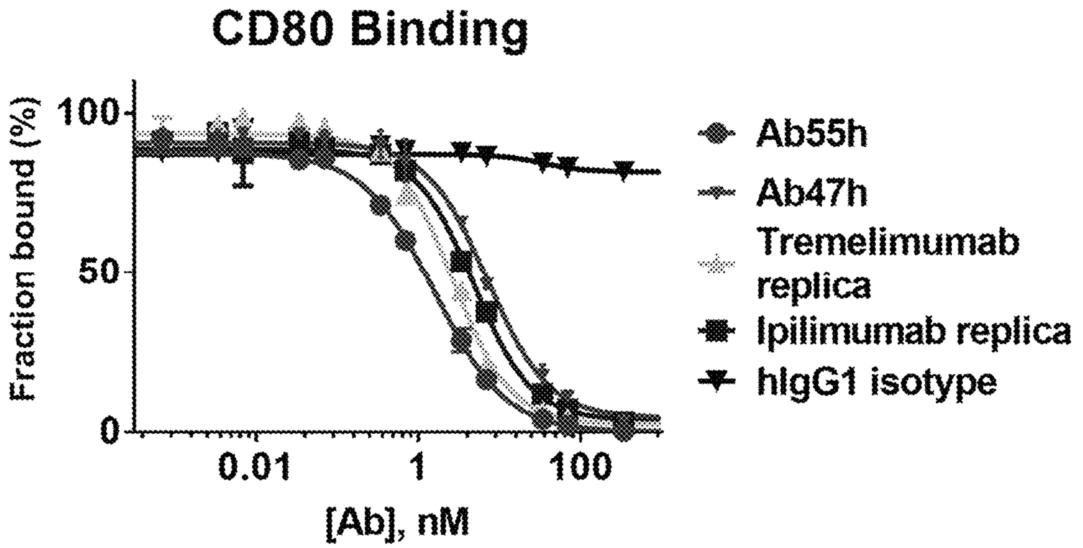
FIGS. 4A-4B are graphs demonstrating that the candidate antibody blocks binding of human CTLA-4 to CD80 and CD86.
Figure 4B:
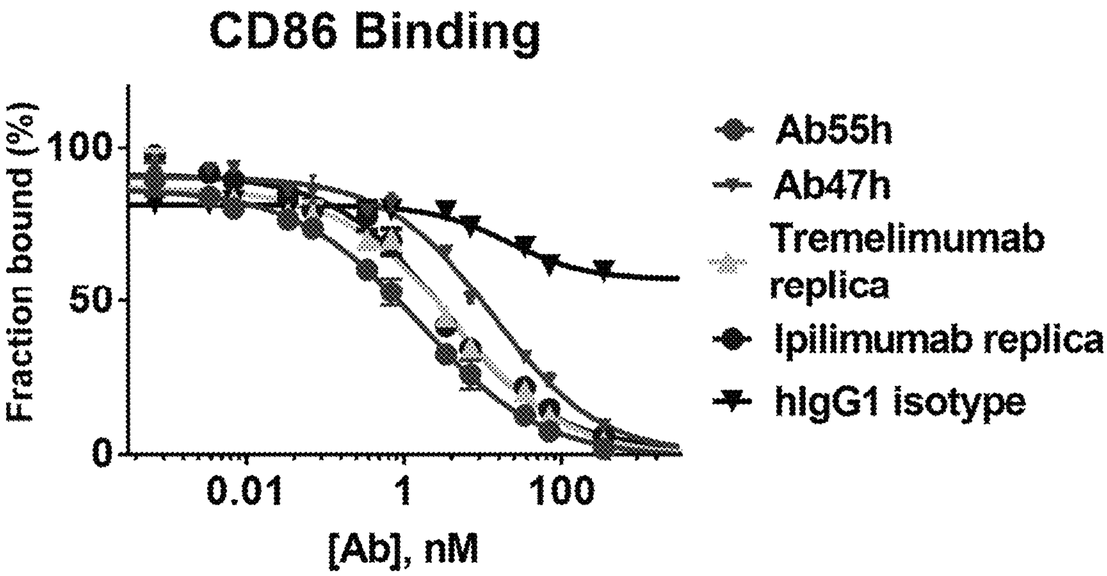

CTLA-4 is an inhibitory immune modulator which competes with the immunostimulatory CD28 modulator over the same ligands: CD80 (B7.1) and CD86 (B7.2). As part of their activity, CTLA-4 therapeutic antibodies block the interaction between CTLA-4 and its ligands, leaving the ligands free for CD28 binding. To compare the blocking potential of Ab55h and Ab47h with currently available CTLA-4 therapeutic antibodies ipilimumab and tremelimumab, the decrease in CD80/86 protein binding to cells expressing hCTLA-4 was measured. First, HEK293-hCTLA-4 cells were incubated with the tested antibodies in a serial dilution for 30 minutes. Next, recombinant human CD80-mFC or CD86-mFC (fusion proteins of the extracellular part of CD80 or CD86 fused with a mouse IgG2b Fc segment) was added for an additional hour. The binding of the ligands (CD80 or CD86) was tested using a secondary antibody targeting mouse Fc and labeled with ALEXA FLUOR® 647. The fluorescence was measured and analyzed. The experiment was performed in triplicate and is representative of three biological repeats. Plots of the binding of CD80 and CD86 to HEK293-hCTLA-4 cells are shown in FIGS. 4A and 4B, respectively. The half maximal inhibitory concentration (IC$_{50}$) for the tested antibodies is shown in Table 10. Ab55h displayed an improved blocking potential, compared with the ipilimumab and tremelimumab replicas control antibodies, for both CD80 and CD86 ligands. Taken together, the Ab55h blocking potential to CD80 and CD86 are superior to ipilimumab and tremelimumab.

TABLE 10

| IC$_{50}$ Values for Inhibition of CD80 and CD86 Binding | | |
|---|---|---|
| Antibody | CD80 blocking IC$_{50}$ (95% CI) | CD86 blocking IC$_{50}$ (95% CI) |
| Ab55h | 1.6 nM (1.3-1.9) | 1.5 nM (1.0-2.2) |
| Ab47h | 7.1 nM (5.6-9.1) | 13.2 nM (9.3-18.8) |
| Ipilimumab replica | 4.8 nM (3.9-59) | 3.3 nM (2.2-4.8) |
| Ratio Ab55h-Ipilimumab:Ab55h | 3.0X | 2.2X |
| Tremelimumab replica | 2.6 nM (2.1-3.3) | 4.2 nM (2.9-6.2) |
| Ratio Ab55h-Tremelimumab:Ab55h | 1.6X | 2.8X |

CD80/86 Competition with CTLA-4 Antibodies

Figure 5A:
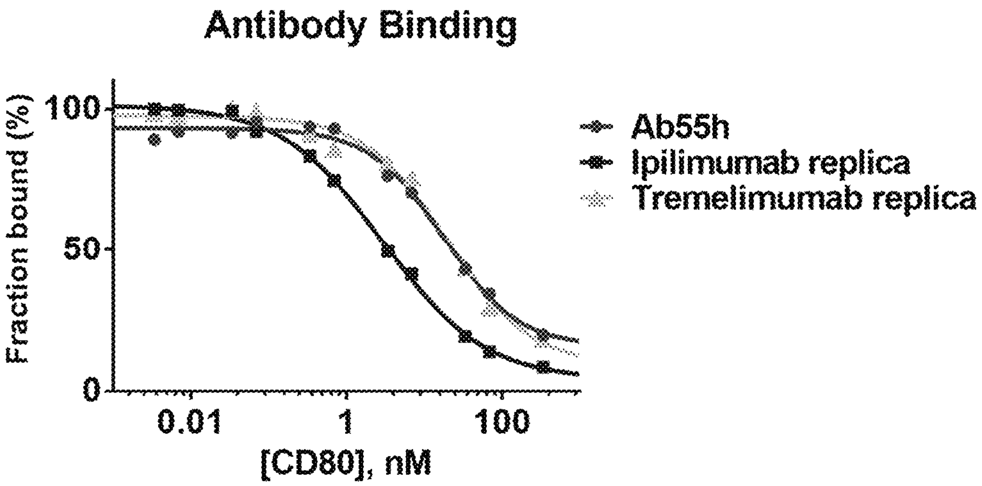
FIGS. 5A-5B are graphs showing CD80 and CD86 competition with candidate CTLA-4 antibodies.
Figure 5B:
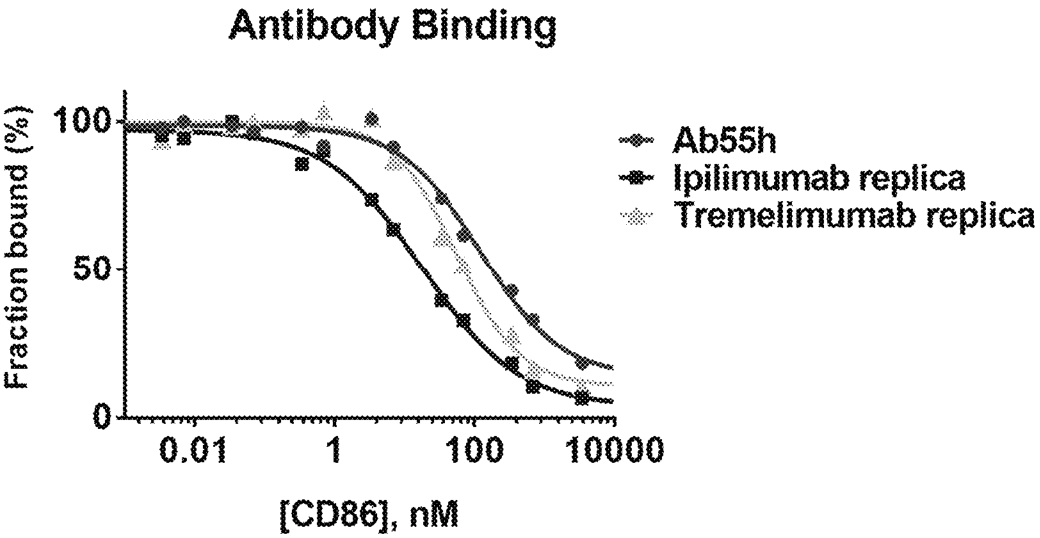

While the blocking assay described above demonstrated the ability of the tested antibodies to block ligand (CD80 and CD86) binding to CTLA-4, an additional reciprocal assay was used to quantify the level of ligands necessary to remove the antibodies. HEK293-hCTLA-4 cells were incubated with the indicated antibodies (1 ug/ml). CD80 or CD86 recombinant proteins were added in a serial dilution. The binding of the antibodies to CTLA-4 expressing cells was measured using a fluorescence-labeled anti-human antibody. FIGS. 5A and 5B show the percentage of bound antibody (MFI was normalized to the maximal and minimal signals) over the concentration of CD80 (FIG. 5A) or CD86 (FIG. 5B). The concentration of CD80 or CD86 required for Ab55h removal was higher than the concentration required for ipilimumab. The CD86 IC$_{50}$ level for Ab55h removal was higher than for ipilimumab and tremelimumab. The CD80 IC$_{50}$ was higher for Ab55h versus ipilimumab but was similar for Ab55h versus tremelimumab (Table 11). The blocking comparison to CD80 and to CD86 demonstrates that Ab55h is superior to both ipilimumab and tremelimumab. The difference in IC$_{50}$ level between the two ligands is indicative of the relative binding difference between CD80 and CD86 to CTLA-4 in cell-based assays.

TABLE 11

IC$_{50}$ Values for Inhibition of Antibodies' Binding to Cells by CD80 or CD86

| Antibody | CD80 blocking IC$_{50}$ (95% CI) | CD86 blocking IC$_{50}$ (95% CI) |
|---|---|---|
| Ab55h | 17.7 nM (10.8-29) | 120 nM (62-232) |
| Ipilimumab | 3 nM (2.3-3.8) | 18 nM (11.9-27.1) |
| Ratio Ab55h-Ipilimumab:Ab55h | 5.9X | 6.6X |
| Tremelimumab | 20 nM (9.9-40) | 55 nM (35.4-86.6) |
| Ratio Ab55h-Tremelimumab:Ab55h | 0.9X | 2.2X |

Antibody Binding to Activated Human T Cells

Figure 6A:
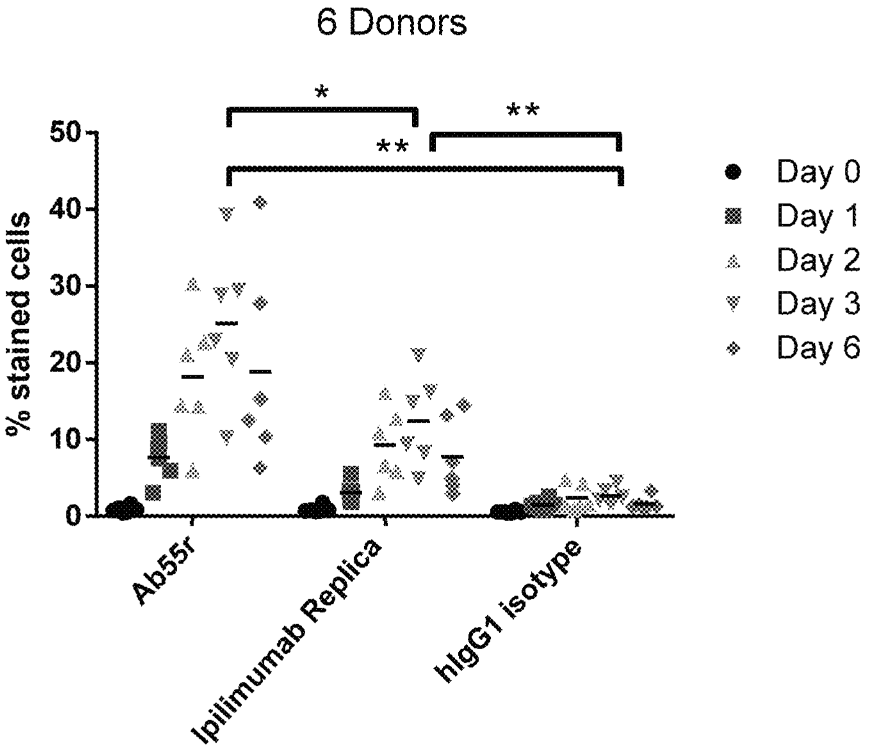
FIGS. 6A-6B are graphs showing antibody binding to activated human T cells.

CTLA-4 is expressed on peripheral T cells after activation. Therefore, antibodies binding to activated human T cells provide a general indication of in vivo cell binding. Peripheral blood mononuclear cells (PBMCs) were isolated from blood samples of six healthy donors. The CD4$^+$ T cells were isolated using negative selection with magnetic beads. Cells were grown on 96-well plates to a density of 300,000 cell/well and activated using TransAct reagent (Miltenyi, 130-111-160) at a 1:100 dilution. On days 0, 1, 2, 3, 6, cell samples were fixed and permeabilized (Cytofix/CytoPerm Kit, BD, 554714) and incubated with 6.7 nM of Ab55r, an Ipilimumab replica, or an hIgG1 control antibody, directly linked to Allophycocyanin (APC). Flow cytometry was used to measure antibody binding, as described above, without elimination of dead cells. FIG. 6A shows the percentage of stained cells (e.g., cells bound to hCTLA-4) in each antibody on each day for the six healthy donors. As expected, no binding was detected before activation on day 0. An increase in the percentage of bound cells was detected from day 1 onward, with a maximal pick of 27% on day 3. The percentage of stained cells varied between different donors, indicating variability in stimulation level or in hCTLA-4 expression in response to stimulation. Remarkably, Ab55r bound more cells from day 1 and onward, indicating an improved binding of primary human T-cells. In FIG. 6A, the asterisk represents statistical significance using 2-way ANOVA test, p-value: **<0.005, *<0.05.

Figure 6B:
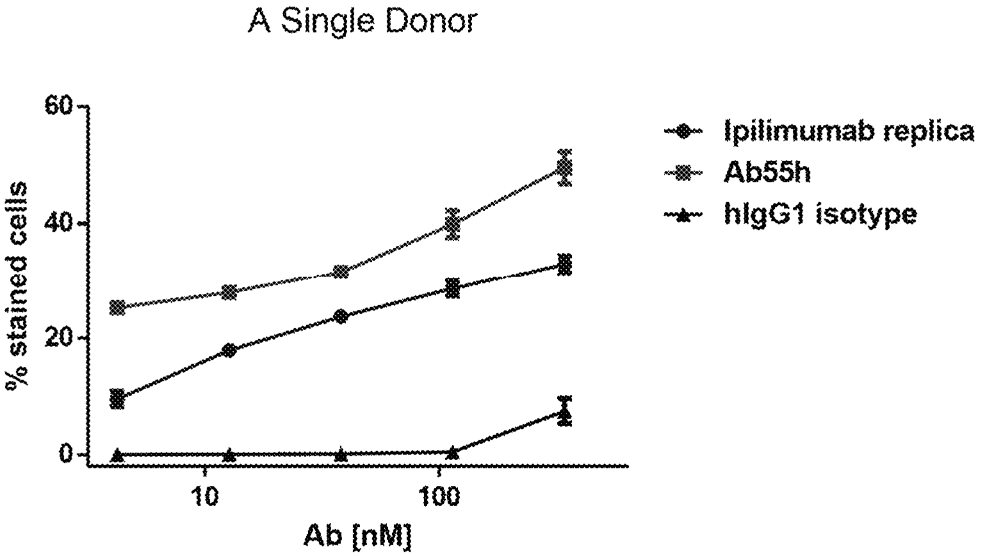

A similar experiment was conducted to test Ab55h binding at different concentrations. This time, the binding of fluorescently-labeled Ab55h, an Ipilimumab replica, or a hIgG1 isotype control to activated T cells from a single donor at day 3 was tested using serial dilutions (FIG. 6B). Ab55h was found to bind a higher percentage of T cells at all concentrations tested, as compared to the Ipilimumab replica.

hPBMC Activation with CTLA-4 Antibodies

The activation status of T cells was evaluated through the secretion of Th1 cytokines, which are associated with the activity of T helper cells. T helper cells are essential for efficient immune response to stimuli. In order to assess the contribution of CTLA-4 antibodies to the Th1 response, a bead-based analysis of IL-2, an exemplary Th1 cytokine, was performed to analyze activated PBMCs in the presence of Ab55h or Ipilimumab.

Figure 7A:
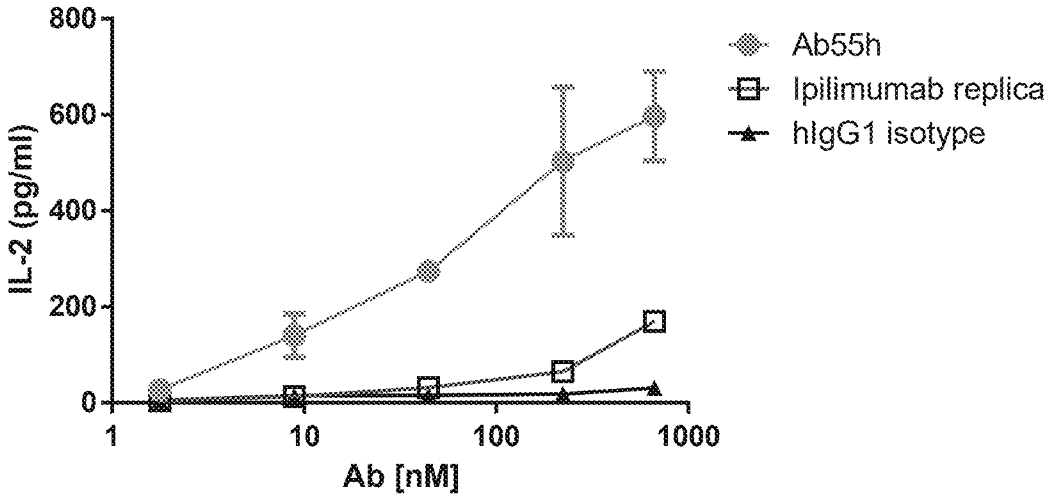
FIGS. 7A-7B are graphs showing the concentration of IL-2 in activated PBMCs following incubation with the indicated antibodies at different concentrations and 100 ng/mL *Staphylococcus* enterotoxin A ("SEA") for five days. PBMCs from two different healthy donors were used.
Figure 7B:
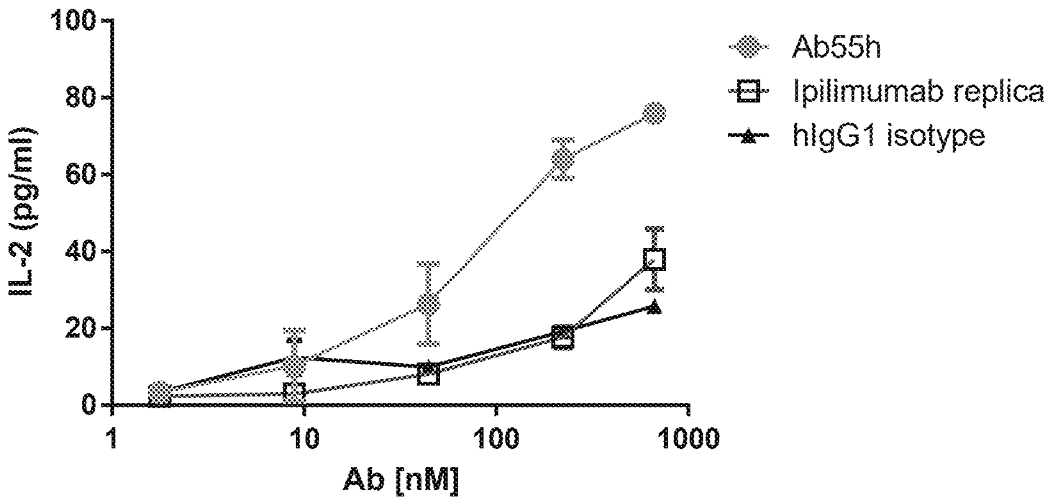

PBMCs were isolated from two healthy donors with Ficoll-Paque™ and frozen. PBMCs were thawed, and plated at a concentration of 100,000 cells/well in a 96-well plate and activated with 100 ng/ml *Staphylococcus enterotoxin* A ("SEA"). Ab55h, an Ipilimumab replica, and a hIgG1 control antibody were added to the activated cells at a serial dilution concentration. The cells were incubated for 5 days at 37° C. and the levels of secreted IL-2 were measured using a LEGENDplex™ Human Th1 assay (BioLegend). The experiment was performed in duplicate. As shown in FIGS. 7A-7B, Ab55h induced IL-2 secretion to a much higher level than ipilimumab.

PBMC Activation with a Combination of CTLA-4 and PD1 Antibodies

Figure 8A:
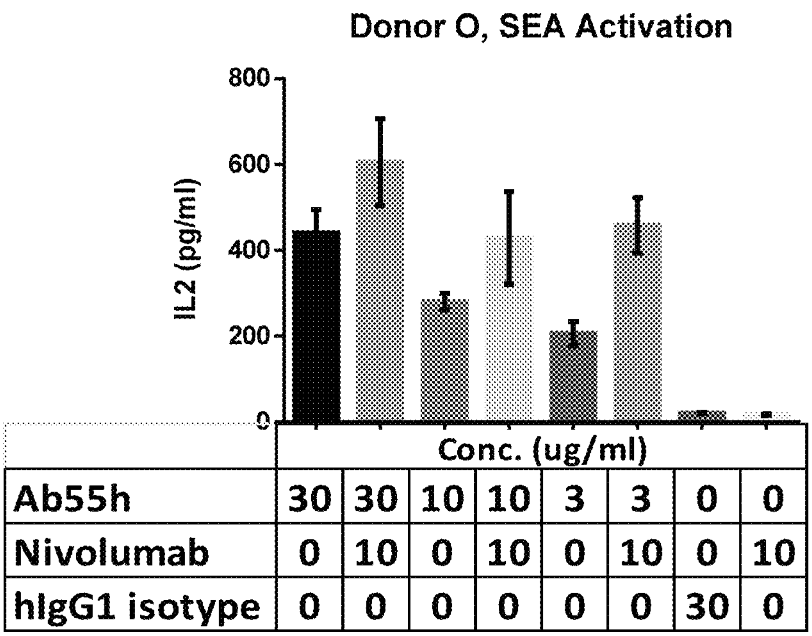
FIGS. 8A-8B are graphs showing the concentration of IL-2 in activated PBMCs following incubation with the indicated antibodies (alone or in combination with nivolumab, a PD1 antibody) at the concentrations shown. PMBCs from two different donors were used.
Figure 8A:
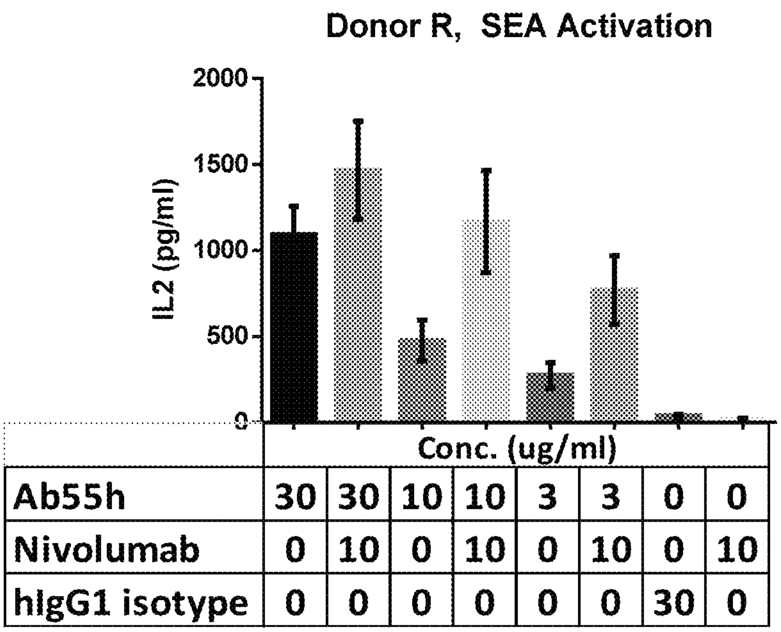
Figure 8B:
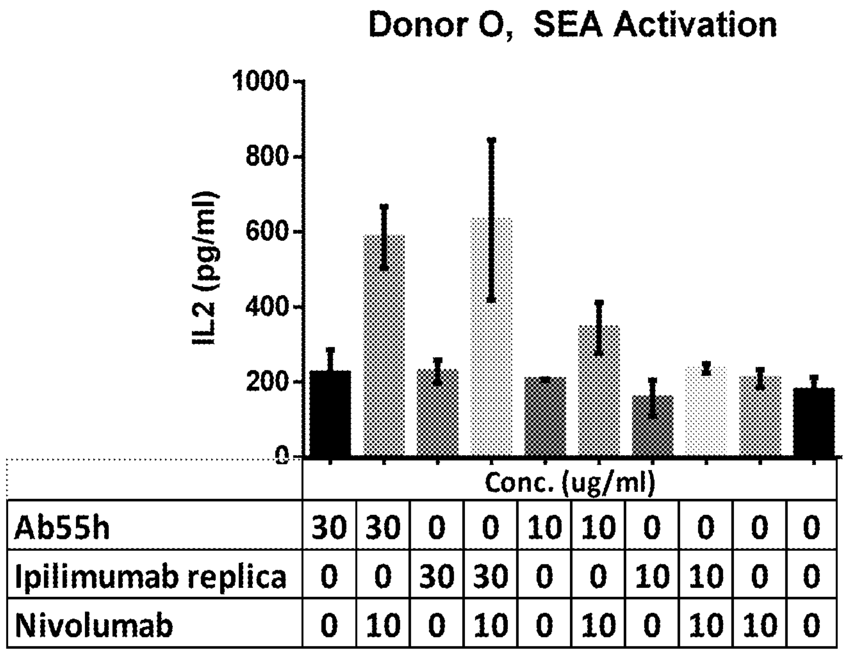
Figure 8B:
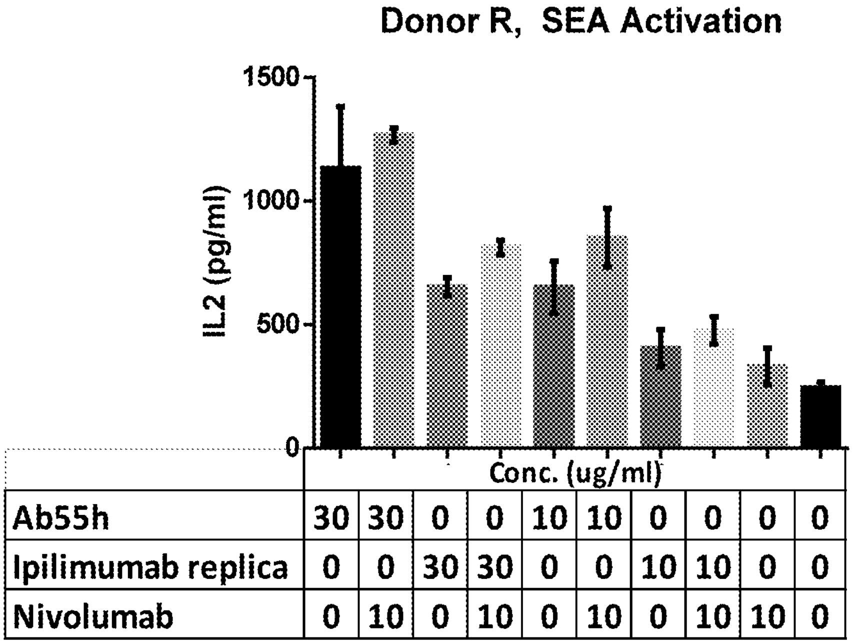

CTLA-4 antibodies were shown to have additive effect with other immune checkpoint antibodies, such as PD1 antibodies. In a therapeutic setting and for certain indications, a CTLA-4 antibody (Ipilimumab) is administered in a combination with a PD1 antibody (Nivolumab). To test the additive effect of the Ab55h antibody with a PD1 antibody, PBMCs from two healthy donors were plated at a concentration of 100,000 cells/well in a 96-well plate and activated with 100 ng/ml SEA. Ab55h was added at a concentration of 3, 10, or 30 ug/ml alone or in combination with 10 ug/ml nivolumab. Nivolumab alone, as well as a hIgG1 isotype antibody, was also tested, the latter used as a control. IL-2 secretion was measured on day 6. While nivolumab alone did not elicit an IL-2 response in this assay, the combination of nivolumab and Ab55h resulted with an increased secretion of IL-2 compared to Ab55h alone in both donors and at all concentrations (FIGS. 8A-8B). Next, the combination of Ab55h and nivolumab was compared with the combination of ipilimumab replica and nivolumab combination. At concentrations of 10 ug/ml CTLA-4 antibody, the Ab55h, alone was better than ipilimumab and the Ab55h+nivolumab combination was better than the ipilimumab+nivolumab combination in both donors, while at concentrations of 30 ug/ml, the results were either better with donor R or similar with donor O. The fold-change results are presented in Tables 12 and 13.

TABLE 12

Il-2 Fold-change between Ab55h as a Single Agent and in Combination with Nivolumab

| Ab55h concentration (ug/ml): | 30 | 10 | 3 |
|---|---|---|---|
| Donor R SEA | 1.3X | 2.5X | 2.8X |
| Donor O SEA | 1.4X | 1.5X | 2.2X |

TABLE 13

IL-2 Fold-change of Ab55h, Ab55h + Nivolumab, Ipilimumab, Ipilimumab + Nivolumab, Nivolumab and hIgG1 control

| | | CTLA4 Ab concentration (ug/ml) | | |
|---|---|---|---|---|
| | | 30 | 10 | 0 |
| Donor R | Ab55h | 4.6 | 2.7 | |
| | Ipilimumab | 2.7 | 1.7 | |
| | Ab55h + Nivolumab (*) | 5.2 | 3.5 | |
| | Ipilimumab + Nivolumab (*) | 3.3 | 2.0 | |
| | Nivolumab (*) | | | 1.4 |
| Donor O | Ab55h | 1.3 | 1.2 | |
| | Ipilimumab | 1.3 | 0.9 | |
| | Ab55h + Nivolumab (*) | 3.3 | 1.9 | |
| | Ipilimumab + Nivolumab (*) | 3.6 | 1.3 | |
| | Nivolumab (*) | | | 1.2 |

(*) Nivolumab at a concentration of 10 ug/ml

Activity of Blocking Downstream Signaling (NFAT Reporter Activity)

Figure 9A:
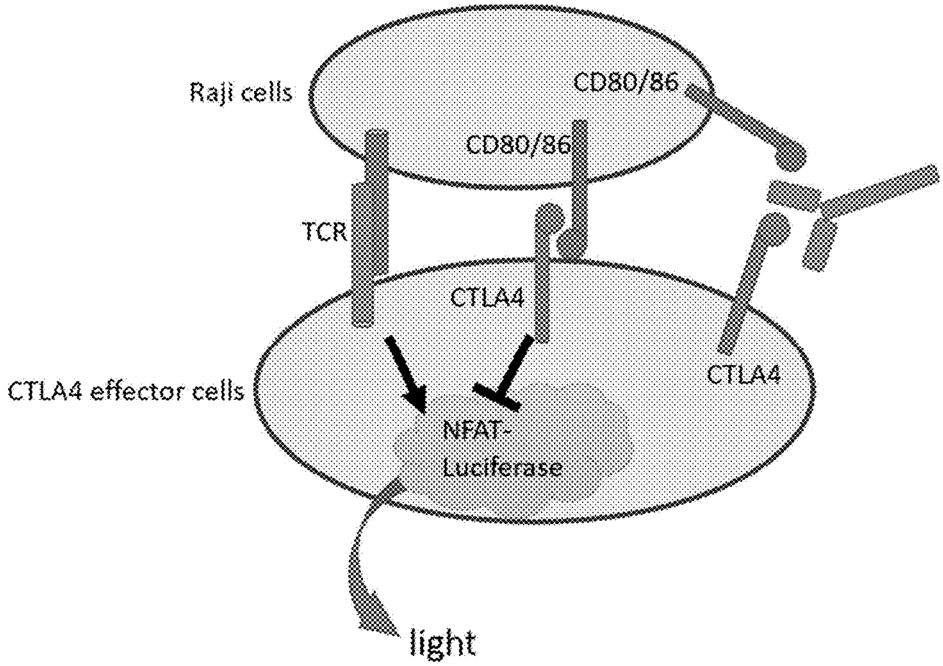
FIGS. 9A-9B are graphs showing the inhibitory activity of anti-CTLA-4 antibodies on downstream signaling using an NFAT report assay.
Figure 9B:
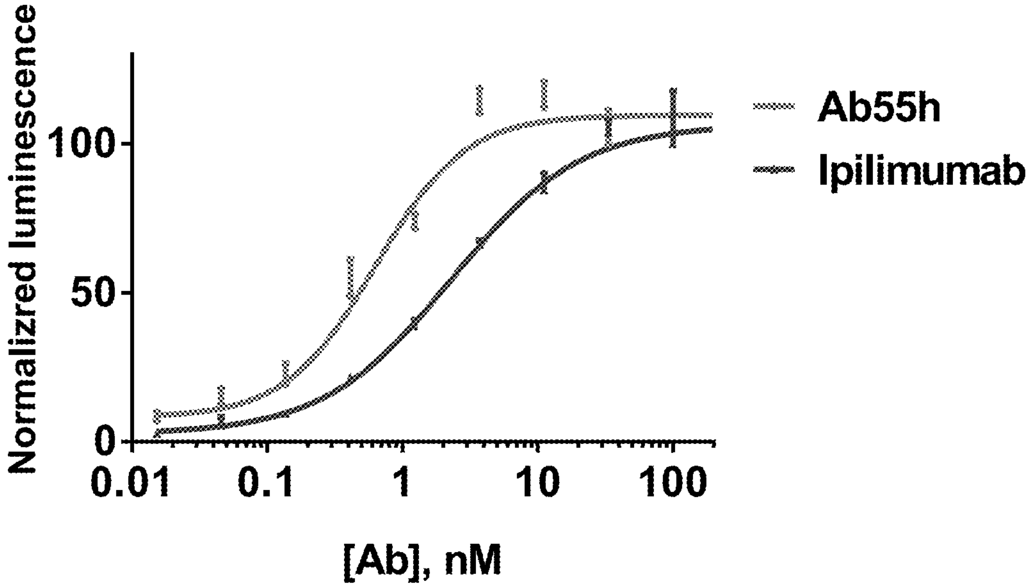

To detect Ab55h's ability to elicit T cell activation, the activity of the NFAT transcription factor in T cells (downstream signaling to T cell CD28 activation signaling) was tested using a reporter cell line. A commercially available kit (Promega CS186920) was used to measure NFAT activity following cell activation with TCR binding and de-activation from the constitutive expression of CTLA-4 on the cell membrane. The kit includes two modified cell types: Raji cells that express T cell activator constitutively, and CTLA-4 effector cells that express TCR and a non-recycling version of CTLA-4. The latter cells also possess a luciferase gene under an NFAT promoter. When the two cell types are co-cultured, no luciferase signal is present due to CTLA-4 inhibition. The addition of CTLA-4 blocking antibodies is expected to relieve the inhibitory signal and to lead to luciferase expression. Ab55h, the ipilimumab control antibody, and a hIgG1 isotype control were added in a serial dilution and the luciferase signal was measured after 16 hours. FIG. 9 shows the normalized luciferase signal for each antibody at different concentrations and Table 14 shows the $EC_{50}$ value for luciferase activation using each antibody. The results show that Ab55h's improved binding and blocking of hCTLA-4 over ipilimumab translates to improved T cell activation signaling.

TABLE 14

$EC_{50}$ Values for NFAT Reporter Activity Assay

| Antibody | NFAT reporter $EC_{50}$ (95% CI) |
|---|---|
| Ab55h | 0.63 nM (0.43-0.91) |
| Ipilimumab | 2.3 nM (1.65-3.2) |
| Ratio Ab55h Ipilimumab:Ab55h | 3.65X |

Downstream Blocking Activity of CTLA-4 Antibodies (SHP1:β-GAL Reporter)

Figure 10A:
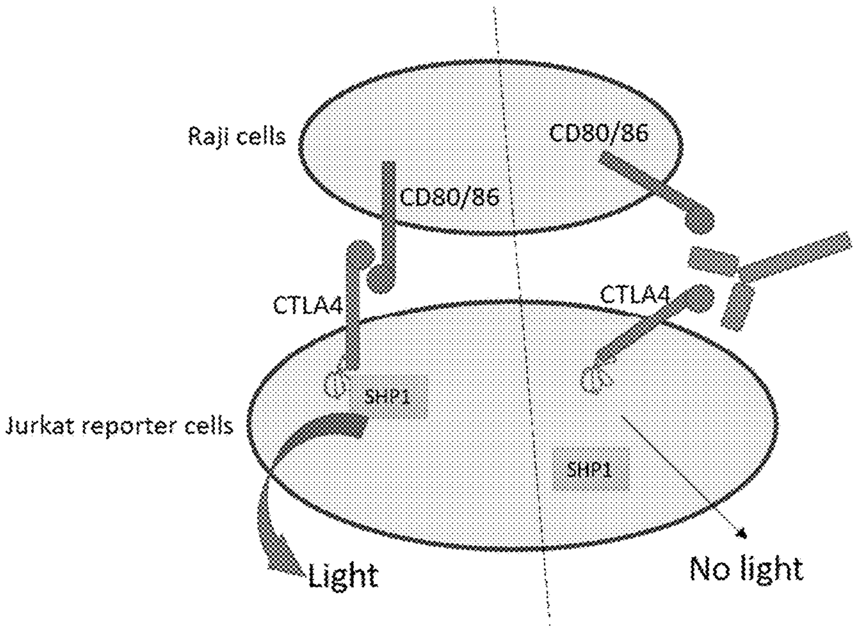
FIGS. 10A-10B are graphs showing the inhibitor activity of anti-CTLA-4 antibodies on downstream signaling using an SHP1 reporter activity assay.
Figure 10B:
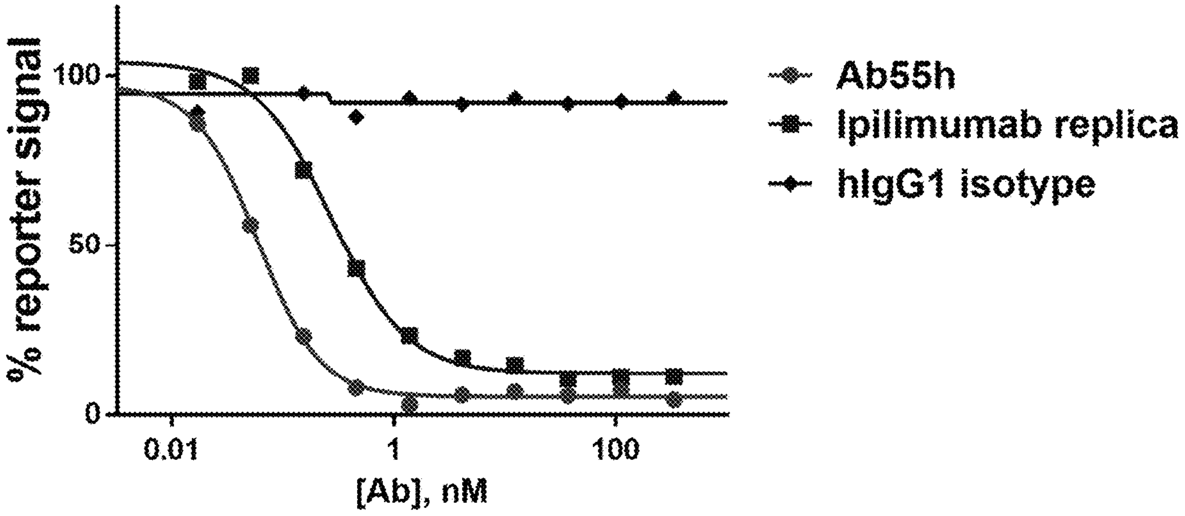

The reduction in CTLA-4 intracellular activity following the addition of hCTLA-4 blocking antibodies is indicative of T cell activation status. To measure directly the intracellular signaling of hCTLA-4 in response to activation and to the addition of CTLA-4 blocking antibodies, the SHP1:β-GAL Jurkat reporter system was used. The system measures of CTLA-4 intracellular activity through a SHP1 reporter. A commercial reporter Jurkat cell line (DiscoverX 493-1094C19) expressing hCTLA-4 and SHP1: β-GAL split reporter were co-cultured with Raji cells that express CD80 and CD86. In the assay, CTLA-4 on the reporter cells binds CD80/CD86, leading to the activation of the β-GAL reporter. Addition of the CTLA-4 blocking antibodies prevents the binding of CD80/CD86 to the Jurkat reporter cells, resulting in a reduced β-GAL signal. β-GAL activity was measured using DiscoverX PATHHUNTER® bioassay detection kit (93-0933E). FIG. 10 shows the normalized SHP1 reporter activity when Ab55h, ipilimumab replica, or the hIgG1 isotype control were added to co-cultured cells in a serial dilution and incubated for two hours. Table 15 shows the $IC_{50}$ values for the different antibodies.

While the isotype control antibody did not decrease the light signal, indicating no change in ligands binding to CTLA-4, CTLA-4 antibodies reduced the signal in a dose-dependent manner. Ab55h was 4.5 fold better in blocking CTLA-4-CD80/86 binding in this assay compared to ipilimumab.

TABLE 15

$IC_{50}$ Values for SHP1 Reporter Activity Assay

| Antibody | SHP1 reporter $IC_{50}$ (95% CI) |
|---|---|
| Ab55h | 0.059 nM (0.047-0.075) |
| Ipilimumab | 0.27 nM (0.2-0.36) |
| Ratio Ab55h:Ipilimumab | 4.5X |

Antibody Internalization

Figure 14:
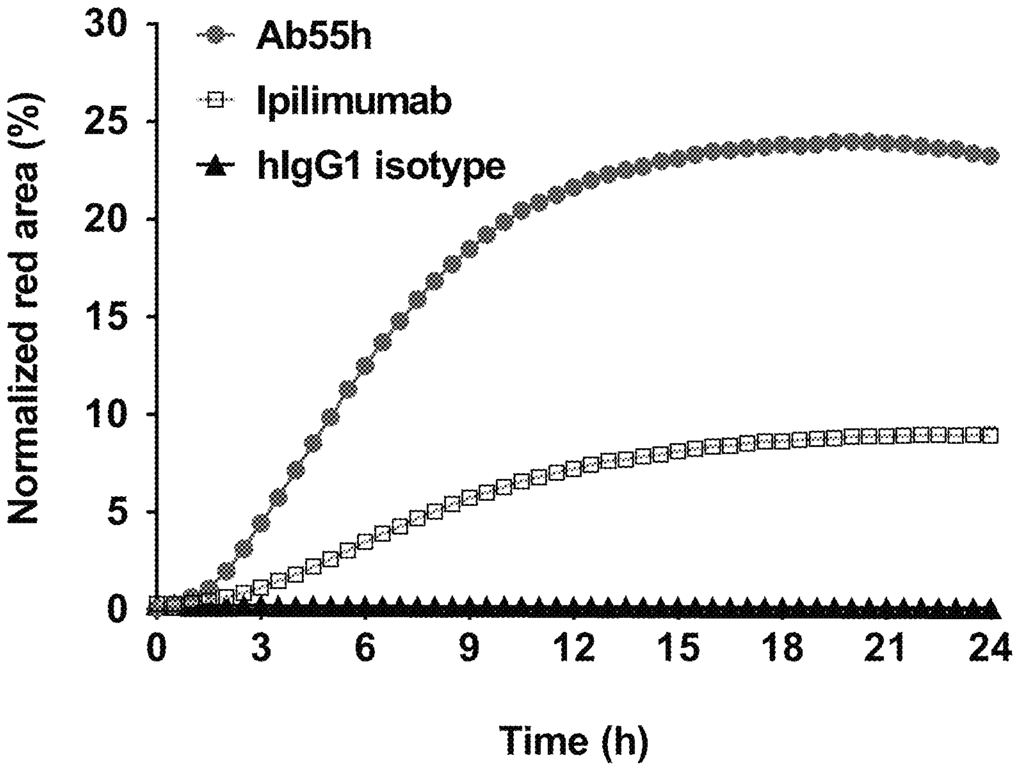
FIG. 14 is a graph showing antibody internationalization using the IncuCyte® S3 system. Antibodies were labeled with an acidic pH-sensitive probe and added to 293-CTLA-4 cells. The data, from lowest to highest internalization, correspond to hIgG1 (isotype control), ipilimumab and Ab55h. The increase in fluorescence signal over time is attributed to the entry of the antibodies into acid lysosomes and endosomes.

The internalization activity of Ab55h was compared with ipilimumab using the IncuCyte® S3 system. The antibodies were labeled with an acidic pH-sensitive probe and were added to 293-CTLA-4 cells. The increase in fluorescence signal over time is attributed to the entry of the antibodies into acidic lysosomes and endosomes. The results show that Ab55h has enhanced internalization activity relative to ipilimumab within 24 hours and at a concentration of 0.8 μg/mL (FIG. 14), a concentration which is below the saturation concentration for both antibodies. It is expected that higher cell internalization allows an increased level of CD80 and CD86 costimulation with CD28, leading a stronger activation of the immune system (Qureshi et al., Science, 332:600-03, 2011).

Example 3: In Vivo Anti-Tumor Activity of Anti-CTLA-4 Antibodies

This example investigates the anti-tumor activity of the anti-CTLA-4 antibodies described herein in an animal model.

Tumor Reduction in an Animal Model

Figure 11A:
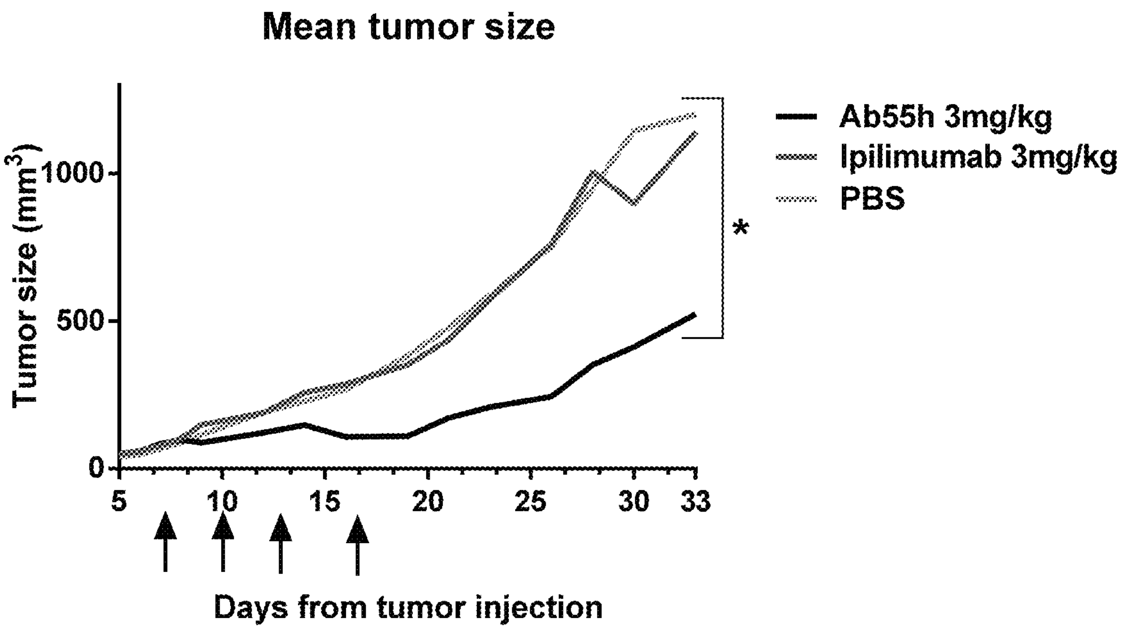
FIGS. 11A-11D are graphs showing the anti-tumor effects of exemplary anti-CTLA-4 antibodies in hCTLA-4 knock-in mice.
Figure 11B:
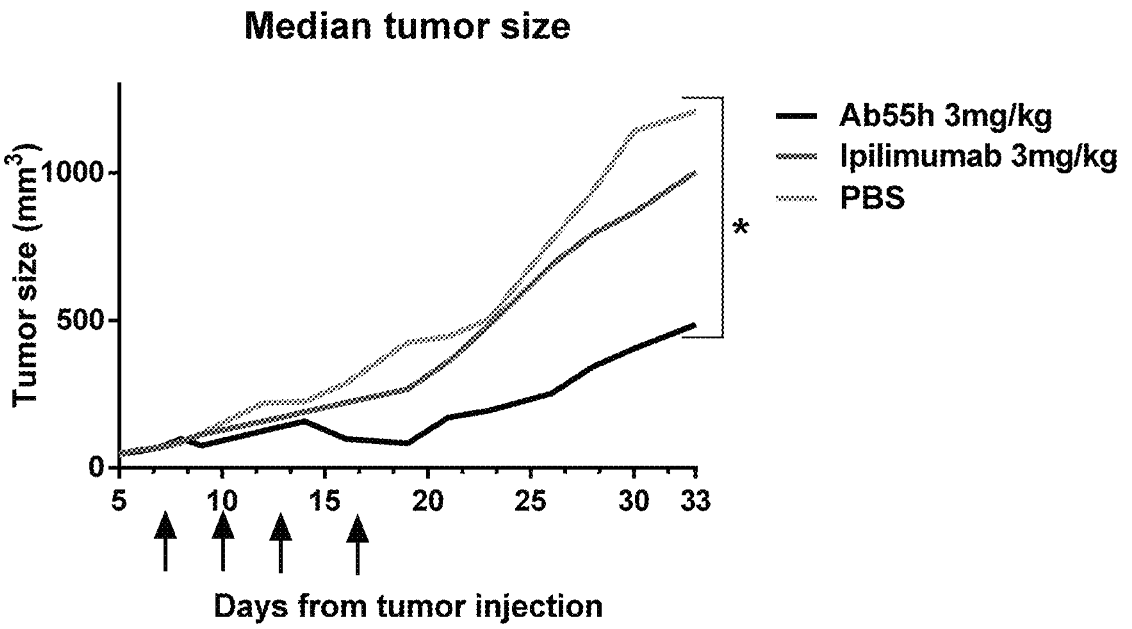
Figure 11C:
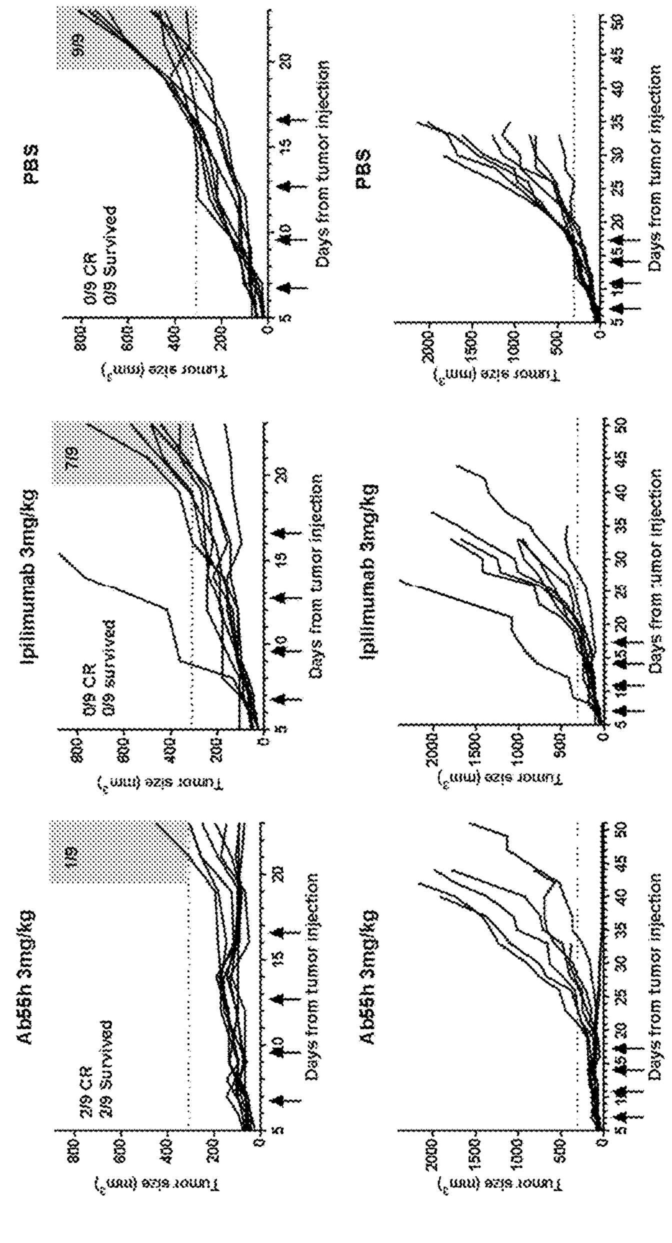
Figure 11D:
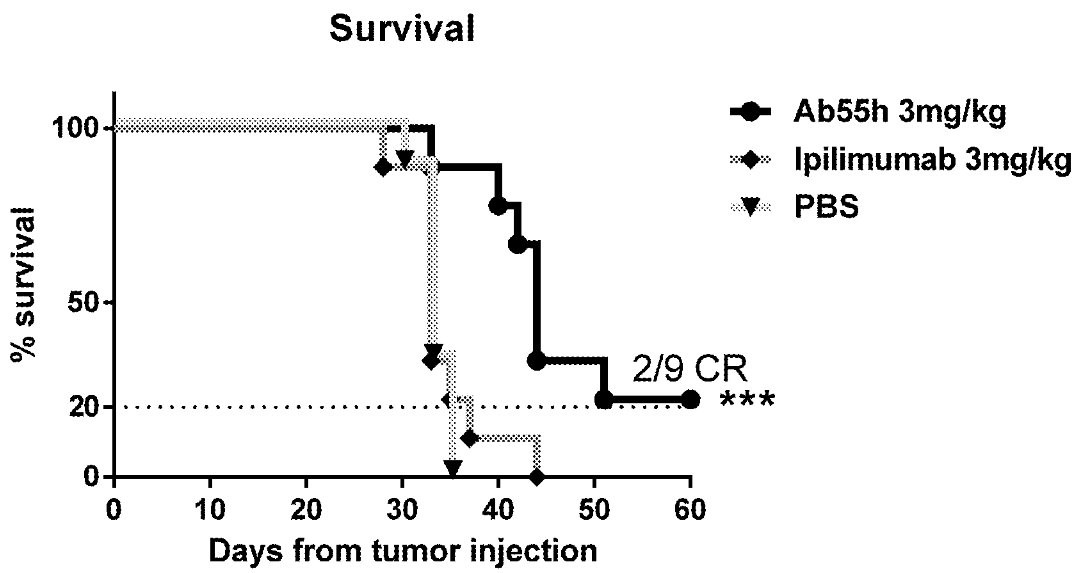

The ability of Ab55h and the ipilimumab control antibody to influence tumor burden was tested in hCTLA-4 knock-in mice. Twenty-seven female C57BL/6 mice with knock-in human CTLA-4 (Nanjing Galaxy Biopharmaceutical Co) were injected with $1\times10^6$ MC38 tumor cells per mouse, intraperitoneally (IP). Once the tumors reached a size range of 70-100 $mm^3$, the mice were randomized into three groups: Ab55h, ipilimumab, and PBS. The mice were injected biweekly over two weeks (a total of 4 injections) with 3 mg/kg Ab55h (produced by Genscript), 3 mg/kg ipilimumab (BMS 1297097A0) or PBS, respectively. Tumor size, mouse weight, and general health parameters were investigated three times a week. Termination conditions were any of the following: tumor size >1500 $mm^3$, formation of a large ulcerated tumor (open wound on tumor site), or body weight loss of >20%. The experiment ended 51 days after inoculation with tumor cells. The results are provided in FIGS. 11A-11D. Treatment with Ab55h significantly delayed tumor growth, while treatment with the ipilimumab did not show a similar effect on the tumor: the tumor growth inhibition (TGI) on day 28 compared to the negative control group was 63% for Ab55h and 15% for ipilimumab (FIG. 11C). Ab55h treatment also increased the average survival time by 10 days, and 2/9 mice (22%) of the Ab55h group showing a complete response. In the two mice, the tumors were eliminated and no tumors were observed by day 51, the end of the trial (FIG. 11D). None of the mice in the ipilimumab group or the PBS group survived or showed a similar complete response of tumor elimination. Further results are given in Table 16.

TABLE 16

| Anti-Tumor Results of Anti-CTLA-4 Antibodies in a Tumor Mouse Model | | | | | |
|---|---|---|---|---|---|
| Group | n | Median Tumor Volume | % TGI | Mean Tumor Volume | Means Comparison p-Value |
| Ab55h | 9 | 343 | 63 | 351 | 0.023* |
| Ipilimumab | 9 | 794 | 15 | 1,006 | 0.956 |
| PBS | 9 | 938 | — | 951 | |

*= p-value < 0.05

Immunological Memory in Recovered Mice

Figure 12:
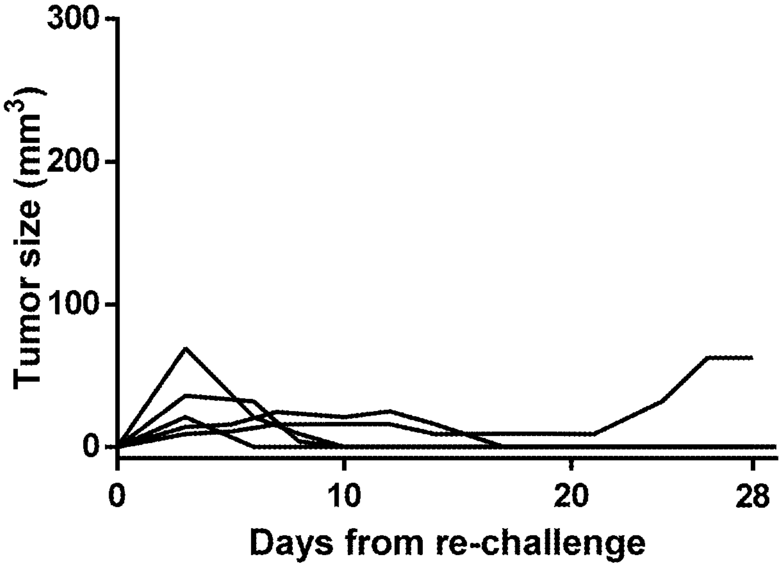
FIG. 12 is a graph showing the results of the re-challenged mice experiment. The graph shows the tumor size of the five re-challenged mice during the 28 days following the re-challenge. The graph represents cumulative data from two trials (n=5).
Figure 13A:
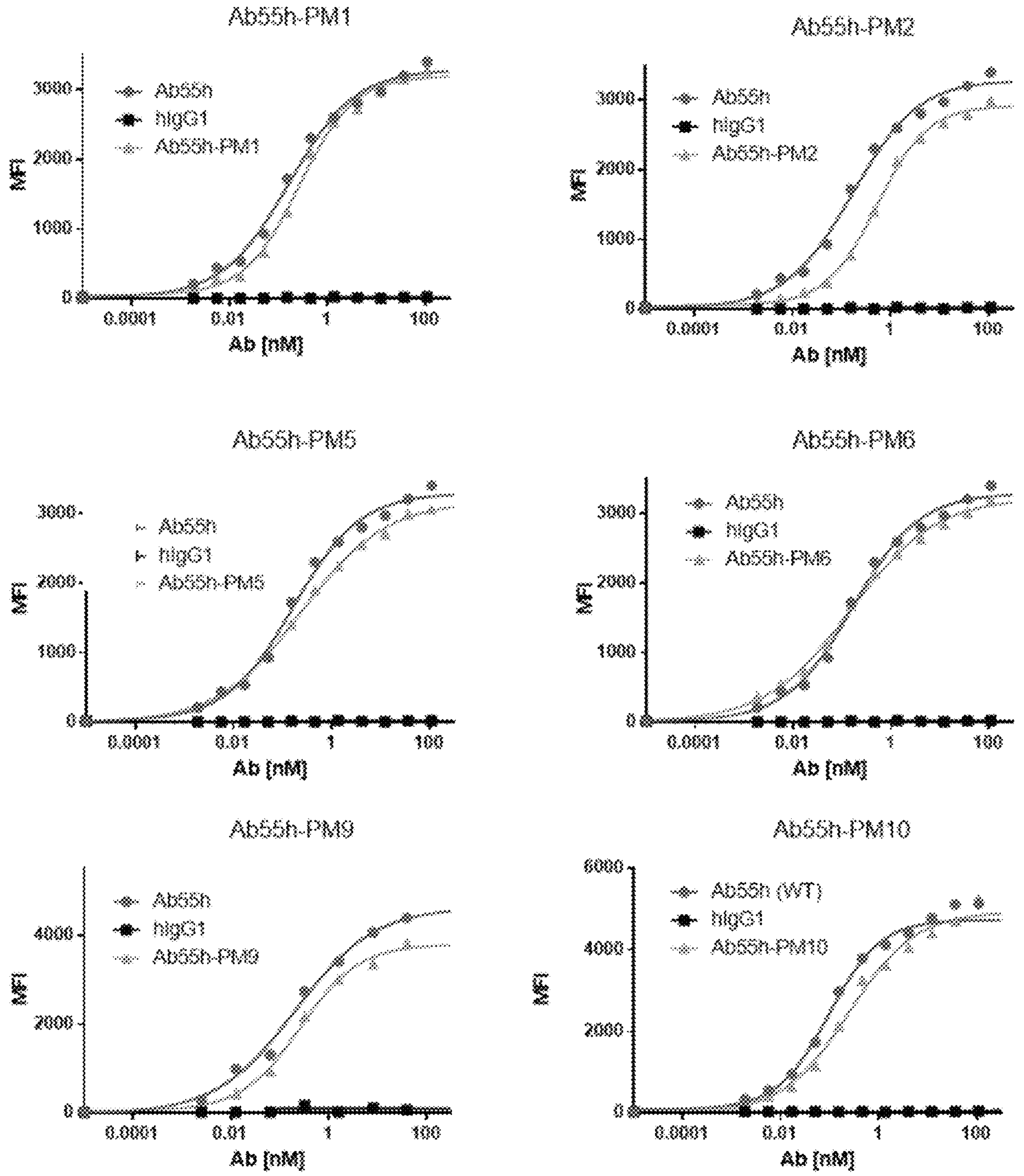
FIGS. 13A-13D are graphs showing binding curves of various Ab55h variants having point mutations in one or more CDRs.
Figure 13B:
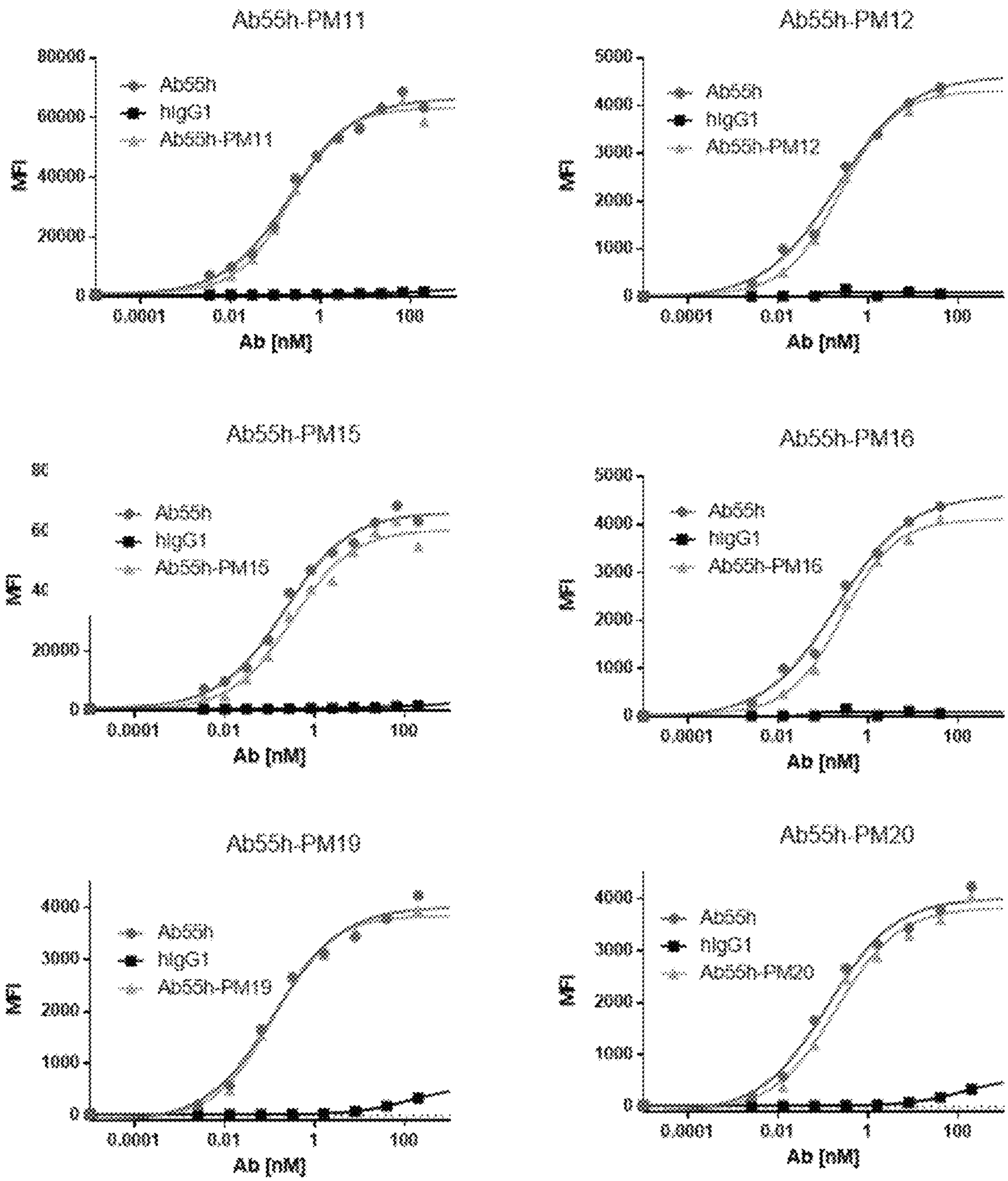
Figure 13C:
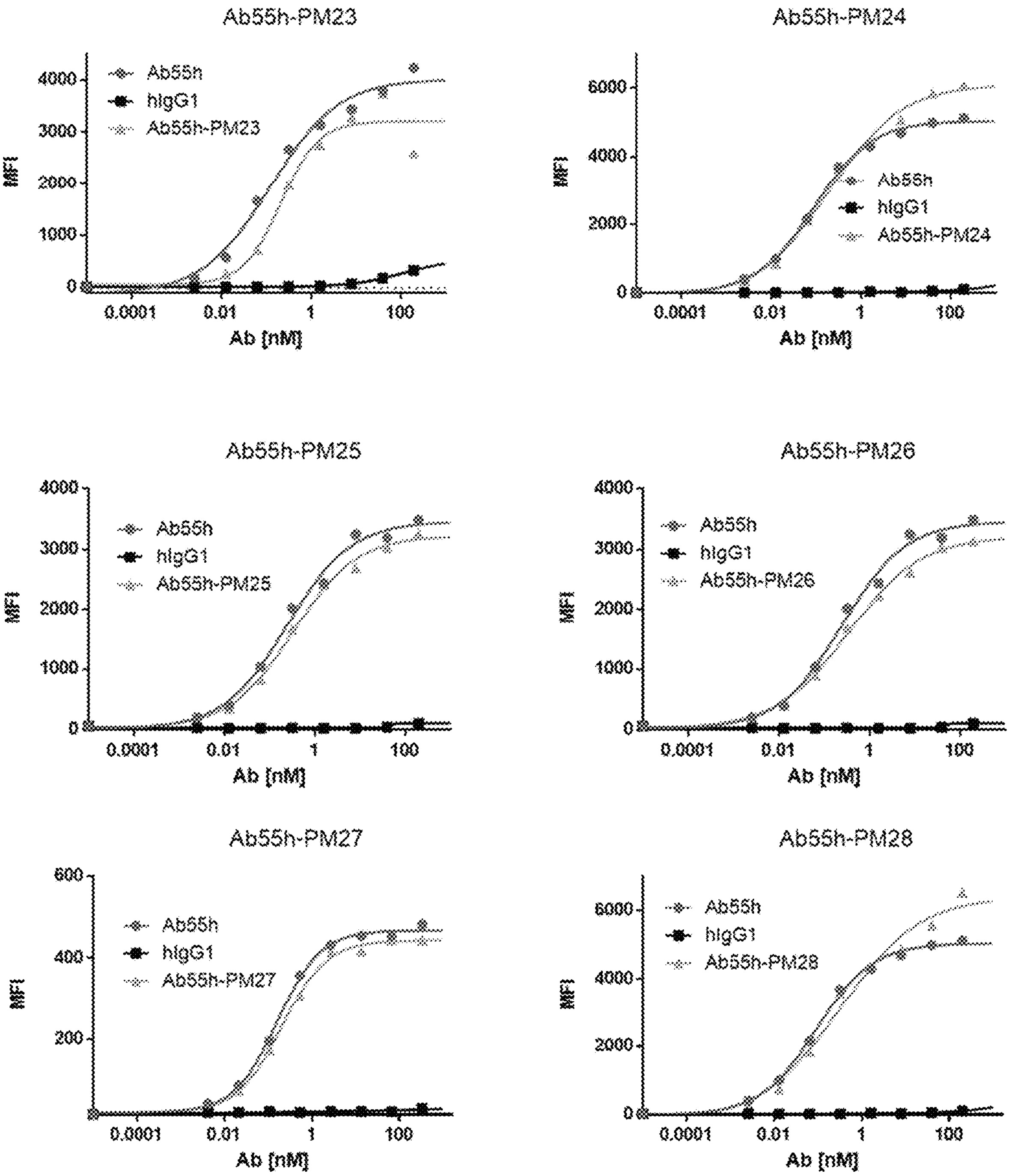
Figure 13D:
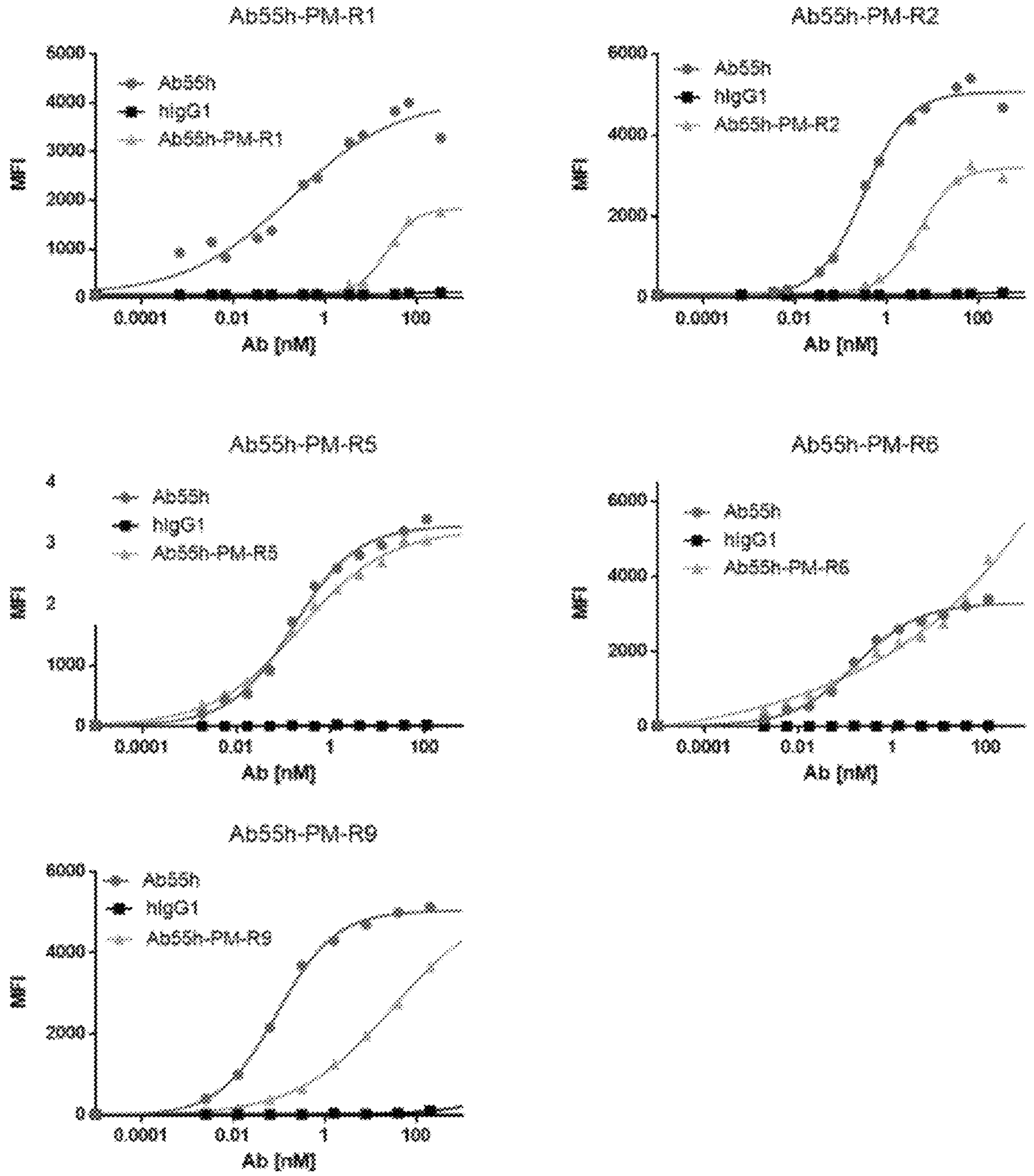

At the end of tumor reduction trials, five mice treated with Ab55h 3 mg/kg and Ab55h 10 mg/kg had a complete response. These mice showed no sign of a tumor. Since immunotherapy treatment is known to induce immunological memory, whether the recovered mice became resistant to MC38 tumor cell inoculation was examined. For this purpose, the mice were re-challenged with $2\times10^6$ MC38 cells, a 2-fold increase over the initial inoculation. Tumor development was measured and compared with tumor development of the previous PBS injected group of mice from the tumor reduction trial. The experiment ended 28 days after the re-challenge. Of the five re-challenged mice, four mice completely recovered, and one mouse showed a delayed tumor growth compared to the PBS or hIgG1 injected groups of mice from the initial trials (FIG. 12). This demonstrates that Ab55h treatment has an immunological memory effect.

Tumor Burden Reduction

The mechanism of action of Ab55h and ipilimumab in tumor burden reduction was evaluated through the analysis of tumor infiltrating immune cells. Female C57BL/6 mice with knock-in of human CTLA-4 were inoculated with MC38 tumor cells, $1\times10^6$ cells per mouse, subcutaneously. On days 7, 10, and 13, the mice were injected intraperitoneally with 10 mg/kg antibody (n=6 per group). On days 15-16, the tumors and spleens were removed, processed, and analyzed for the presence of immune cells using flow cytometry. The results are shown in Table 17 below. $CD45^+$, a general marker for lymphocyte cells, was examined. An increase of these cells in tumors is indicative of an increased immune infiltration into the tumor, while an increase in spleen is indicative of an increased proliferation of lymphocytes and an immune reaction. CD4 is a T helper cell marker. T helper cells are necessary for the activity of other immune cells. CD8 is a cytotoxic T cell marker. Cytotoxic T cells are responsible for killing tumor to cells. Regulatory T cells ($CD4^+Foxp3^+CD25^+$) are a subpopulation of $CD4^+$ cells that, in contrast to effector $CD4^+$ T helper cells, suppress the immune response. Part of the functional activity of the CTLA-4 antibody effect is attributed to a reduction of Treg cells in tumors. As shown in Table 17 below, Ab55h and ipilimumab treatment drastically reduced Treg cells in the tumor with a more pronounced reduction following Ab55h treatment, while the Treg cell population in the spleen was not affected. In addition, Ab55h treatment led to an increase in tumor infiltration, as indicated by the increased $CD4^+$ cells in the tumor, while ipilimumab treatment did not affect the $CD4^+$ cell population in the tumor. Both antibodies increased the $CD4^+$ population in the spleen to a similar level. In addition, Ab55h treatment led to an increase in tumor total lymphocyte infiltration $CD45^+$ cells, which was not seen in the spleen.

TABLE 17

| Analysis of Tumor and Spleen Lymphocytes | | | | | | |
|---|---|---|---|---|---|---|
| | | | % of CD45+ population from cells | % of CD4+ cells population from T cells (CD45 + CD3+) | % of CD8+ cells population from T cells (CD45 + CD3+) | % of Treg (Foxp3 + CD25+) cells population from CD4+ cells population |
| Spleen | Ab55h | Average | 86.00% | 64.30% | 25.40% | 18.20% |
| | | SEM | 1.90% | 0.90% | 0.60% | 0.80% |
| | Ipilimumab | Average | 91.10% | 63.20% | 23.10% | 17.50% |
| | | SEM | 0.70% | 1.20% | 0.90% | 0.70% |
| | hIgG1 | Average | 90.70% | 54.60% | 30.40% | 15.00% |
| | | SEM | 1.30% | 1.10% | 1.30% | 1.90% |
| Tumor | Ab55h | Average | 36.20% | 18.60% | 19.40% | 3.70% |
| | | SEM | 7.30% | 4.70% | 3.10% | 0.90% |
| | Ipilimumab | Average | 28.50% | 6.90% | 22.70% | 7.00% |
| | | SEM | 4.60% | 1.40% | 3.10% | 1.40% |
| | hIgG1 | Average | 20.50% | 5.50% | 11.20% | 45.80% |
| | | SEM | 1.50% | 0.80% | 1.50% | 3.60% |

Note:
the number of samples in each group was n = 6, except for Ipilimumab-treated tumors (n = 4)

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A monoclonal antibody binding to cytotoxic T-lymphocyte-associated protein 4 (CTLA-4), (a) wherein the antibody comprises a heavy chain variable domain ($V_H$), which comprises (i) a heavy chain complementary determining region 1 (HC CDR1) set forth as GDYYWG (SEQ ID NO: 15); (ii) a heavy chain complementary determining region 2 (HC CDR2) set forth as SIYHSGYTYYNPSLKS (SEQ ID NO: 16); and (iii) a heavy chain complementary determining region 3 (HC CDR3) set forth as DSGWYVIAFDY (SEQ ID NO: 17); and wherein the antibody comprises a light chain variable domain ($V_L$), which comprises (i) a light chain complementary determining region 1 (LC CDR1) set forth as RASQSVSSNLA (SEQ ID NO: 21); (ii) a light chain complementary determining region 2 (LC CDR2) set forth as GASTRAT (SEQ ID NO: 22); and (iii) a light chain complementary determining region 3 (LC CDR3) set forth as QQYNNWPPLT (SEQ ID NO: 8);

(b) wherein the antibody comprises a $V_H$, which comprises (i) an HC CDR1 set forth as GDYYWN (SEQ ID NO: 28); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the antibody comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(c) wherein the antibody comprises a $V_H$, which comprises (i) an HC CDR1 set forth as GDYYWG (SEQ ID NO: 15); (ii) an HC CDR2 set forth as SIYHDGYTYYNPSLKS (SEQ ID NO: 31); and (iii) an HC CDR3 set forth as DSGWYVIAFDY (SEQ ID NO: 17); and wherein the antibody comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(d) wherein the antibody comprises a $V_H$, which comprises (i) an HC CDR1 set forth as GDYYWG (SEQ ID NO: 15); (ii) an HC CDR2 set forth as SIYHSAYTYYNPSLKS (SEQ ID NO: 32); and (iii) an HC CDR3 set forth as DSGWYVIAFDY (SEQ ID NO: 17); and wherein the antibody comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(e) wherein the antibody comprises a $V_H$, which comprises (i) an HC CDR1 set forth as GDYYWG (SEQ ID NO: 15); (ii) an HC CDR2 set forth as SIYHSGYTYYNPSVKS (SEQ ID NO: 33); and (iii) an HC CDR3 set forth as DSGWYVIAFDY (SEQ ID NO: 17); and wherein the antibody comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(f) wherein the antibody comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFAY (SEQ ID NO: 34); and wherein the antibody comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(g) wherein the antibody comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDI (SEQ ID NO: 35); and wherein the antibody comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(h) wherein the antibody comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the antibody comprises a $V_L$, which comprises (i) an LC CDR1 set forth as RASQSISSNLA (SEQ ID NO: 49); (ii) an LC CDR2 set forth as GASTRAT (SEQ ID NO: 22); and (iii) an LC CDR3 set forth as QQYNNWPPLT (SEQ ID NO: 8);

(i) wherein the antibody comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the antibody comprises a $V_L$, which comprises (i) an LC CDR1 set forth as RASQSVSSNLA (SEQ ID NO: 21); (ii) an LC CDR2 set forth as AASTRAT (SEQ ID NO: 53); and (iii) an LC CDR3 set forth as QQYNNWPPLT (SEQ ID NO: 8);

(j) wherein the antibody comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the antibody comprises a $V_L$, which comprises (i) an LC CDR1 set forth as RASQSVSSNLA (SEQ ID NO: 21); (ii) an LC CDR2 set forth as GATTRAT (SEQ ID NO: 54); and (iii) an LC CDR3 set forth as QQYNNWPPLT (SEQ ID NO: 8); or (k) wherein the antibody comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the antibody comprises a $V_L$, which comprises (i) an LC CDR1 set forth as RASQSVSSNLA (SEQ ID NO: 21); (ii) an LC CDR2 set forth as GASSRAT (SEQ ID NO: 55); and (iii) an LC CDR3 set forth as QQYNNWPPLT (SEQ ID NO: 8).

2. The monoclonal antibody of claim 1, wherein the antibody specifically binds human CTLA-4.

3. The monoclonal antibody of claim 1, wherein the antibody cross-reacts with human CTLA-4 and a non-human CTLA-4, and wherein the non-human CTLA-4 is a non-human primate CTLA-4, a pig CTLA-4, or a mouse CTLA-4.

4. The monoclonal antibody of claim 1, wherein the antibody binds CTLA-4 expressed on the cell surface.

5. The monoclonal antibody of claim 1, wherein the antibody comprises the heavy chain variable domain set forth as SEQ ID NO: 1 and/or the light chain variable domain set forth as SEQ ID NO: 2.

6. The monoclonal antibody of claim 1, wherein the antibody comprises a heavy chain variable domain that is at least 85% identical to the heavy chain variable domain set forth as SEQ ID NO: 1, and/or a light chain variable domain that is at least 85% identical to the light chain variable domain set forth as SEQ ID NO: 2.

7. The monoclonal antibody of claim 1, wherein the antibody is a humanized antibody.

8. The monoclonal antibody of claim 1, wherein the antibody is a full-length antibody.

9. The monoclonal antibody of claim 8, wherein the full-length antibody is an IgG molecule.

10. The monoclonal antibody of claim 8, wherein the antibody contains an altered Fc fragment relative to a naturally-occurring counterpart, or wherein the antibody contains an afucosylated Fc fragment.

11. The monoclonal antibody of claim 10, wherein the antibody contains an altered IgG1 Fc fragment, wherein the altered IgG1 Fc fragment comprises a K214R substitution, based on EU index numbering, relative to an IgG1 heavy chain constant region.

12. The monoclonal antibody of claim 11, wherein the antibody comprises a heavy chain set forth as SEQ ID NO: 66 and a light chain set forth as SEQ ID NO: 68.

13. The monoclonal antibody of claim 1, wherein the antibody is an antigen-binding fragment.

14. The monoclonal antibody of claim 13, wherein the antigen-binding fragment is Fab, Fab', $F(ab')_2$, or Fv.

15. The monoclonal antibody of claim 1, wherein the antibody is a single-chain antibody or a bispecific antibody.

16. The monoclonal antibody of claim 1, wherein the antibody is conjugated to a detectable label.

17. A nucleic acid or a nucleic acid set, which collectively encode the monoclonal antibody of claim 1.

18. A genetically engineered immune cell, which expresses a chimeric antigen receptor comprising an extracellular domain and at least one cytoplasmic signaling domain, wherein the extracellular domain is a single chain variable fragment (scFv) of a CTLA-4-binding antibody, (a) wherein the scFv comprises a heavy chain variable domain ($V_H$), which comprises (i) a heavy chain complementary determining region 1 (HC CDR1) set forth as GDYYWG (SEQ ID NO: 15); (ii) a heavy chain complementary determining region 2 (HC CDR2) set forth as SIYHSGYTYYNPSLKS (SEQ ID NO: 16); and (iii) a heavy chain complementary determining region 3 (HC CDR3) set forth as DSGWYVIAFDY (SEQ ID NO: 17) and wherein the scFv comprises a light chain variable domain ($V_L$), which comprises (i) a light chain complementary determining region 1 (LC CDR1) set forth as RASQSVSSNLA (SEQ ID NO: 21); (ii) a light chain complementary determining region 2 (LC CDR2) set forth as GASTRAT (SEQ ID NO: 22); and (iii) a light chain complementary determining region 3 (LC CDR3) set forth as QQYNNWPPLT (SEQ ID NO: 8);

(b) wherein the scFv comprises a $V_H$, which comprises (i) an HC CDR1 set forth as GDYYWN (SEQ ID NO: 28); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the scFv comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(c) wherein the scFv comprises a $V_H$, which comprises (i) an HC CDR1 set forth as GDYYWG (SEQ ID NO: 15); (ii) an HC CDR2 set forth as SIYHDGYTYYNPSLKS (SEQ ID NO: 31); and (iii) an HC CDR3 set forth as DSGWYVIAFDY (SEQ ID NO: 17); and wherein the scFv comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(d) wherein the scFv comprises a $V_H$, which comprises (i) an HC CDR1 set forth as GDYYWG (SEQ ID NO: 15); (ii) an HC CDR2 set forth as SIYHSAYTYYNPSLKS (SEQ ID NO: 32); and (iii) an HC CDR3 set forth as DSGWYVIAFDY (SEQ ID NO: 17); and wherein the scFv comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(e) wherein the scFv comprises a $V_H$, which comprises (i) an HC CDR1 set forth as GDYYWG (SEQ ID NO: 15); (ii) an HC CDR2 set forth as SIYHSGYTYYNPSVKS (SEQ ID NO: 33); and (iii) an HC CDR3 set forth as DSGWYVIAFDY (SEQ ID NO: 17); and wherein the scFv comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(f) wherein the scFv comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFAY (SEQ ID NO: 34); and wherein the scFv comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(g) wherein the scFv comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDI (SEQ ID NO: 35); and wherein the scFv comprises a $V_L$, which comprises (i) an LC CDR1 set forth as RASQSVSSNLA (SEQ ID NO: 21); (ii) an LC CDR2 set forth as GASTRAT (SEQ ID NO: 22); and (iii) an LC CDR3 set forth as QQYNNWPPLT (SEQ ID NO: 8);

(h) wherein the scFv comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the scFv comprises a $V_L$, which comprises (i) an LC CDR1 set forth as RASQSISSNLA (SEQ ID NO: 49); (ii) an LC CDR2 set forth as GASTRAT (SEQ ID NO: 22); and (iii) an LC CDR3 set forth as QQYNNWPPLT (SEQ ID NO: 8);

(i) wherein the scFv comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the scFv comprises a $V_L$, which comprises (i) an LC CDR1 set forth as RASQSVSSNLA (SEQ ID NO: 21); (ii) an LC CDR2 set forth as AASTRAT (SEQ ID NO: 53); and (iii) an LC CDR3 set forth as QQYNNWPPLT (SEQ ID NO: 8);

(j) wherein the scFv comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the scFv comprises a $V_L$, which comprises (i) an LC CDR1 set forth as RASQSVSSNLA (SEQ ID NO: 21); (ii) an LC CDR2 set forth as GATTRAT (SEQ ID NO: 54); and (iii) an LC CDR3 set forth as QQYNNWPPLT (SEQ ID NO: 8); or (k) wherein the scFv comprises a $V_H$, which comprises (i) an HC CDR1 set forth as GDYYWG (SEQ ID NO: 15); (ii) an HC CDR2 set forth as SIYHSGYTYYNPSLKS (SEQ ID NO: 16); and (iii) an HC CDR3 set forth as DSGWYVIAFDY (SEQ ID NO: 17); and wherein the scFv comprises a $V_L$, which comprises (i) an LC CDR1 set forth as RASQSVSSNLA (SEQ ID NO: 21); (ii) an LC CDR2 set forth as GASSRAT (SEQ ID NO: 55); and (iii) an LC CDR3 set forth as QQYNNWPPLT (SEQ ID NO: 8).

19. A host cell, comprising the nucleic acid or nucleic acid set of claim 17.

20. A method for modulating an immune response in a subject, the method comprising administering to a subject in need thereof an effective amount of the monoclonal antibody of claim 1.

21. A pharmaceutical composition comprising the antibody of claim 1 and a pharmaceutically acceptable carrier.

22. A pharmaceutical composition comprising the antibody of claim 1 and a liposome, a microcapsule, an albumin microsphere, a microemulsion, a nanoparticle, or a nanocapsule.

* * * * *

SEQUENCE LISTING

```
<160> NUMBER OF SEQ ID NOS: 69

<210> SEQ ID NO 1
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Gly Asp
            20                  25                  30
```

```
Tyr Tyr Trp Gly Trp Ile Arg Gln Pro Pro Gly Lys Gly Leu Glu Trp
        35                  40                  45

Ile Gly Ser Ile Tyr His Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ser Gly Trp Tyr Val Ile Ala Phe Asp Tyr Trp Gly Gln
            100                 105                 110

Gly Thr Leu Val Thr Val Ser Ser
        115                 120


<210> SEQ ID NO 2
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 2

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Glu Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Leu Thr Phe Gly Gly Gly Thr Lys Val Glu Ile Lys
            100                 105


<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa can be Gly or Asn

<400> SEQUENCE: 3

Gly Asp Tyr Tyr Trp Xaa
1               5


<210> SEQ ID NO 4
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa can be Asp or Ser
<220> FEATURE:
```

<221> NAME/KEY: misc_feature
<222> LOCATION: (6)..(6)
<223> OTHER INFORMATION: Xaa can be Gly or Ala
<220> FEATURE:
<221> NAME/KEY: misc_feature
<222> LOCATION: (14)..(14)
<223> OTHER INFORMATION: Xaa can be Leu or Val

<400> SEQUENCE: 4

```
Ser Ile Tyr His Xaa Xaa Tyr Thr Tyr Tyr Asn Pro Ser Xaa Lys Ser
1               5                   10                  15
```

<210> SEQ ID NO 5
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (10)..(10)
<223> OTHER INFORMATION: Xaa can be Asp or Ala
<220> FEATURE:
<221> NAME/KEY: misc_feature
<222> LOCATION: (11)..(11)
<223> OTHER INFORMATION: Xaa can be Tyr or Ile

<400> SEQUENCE: 5

```
Asp Ser Gly Trp Tyr Val Ile Ala Phe Xaa Xaa
1               5                   10
```

<210> SEQ ID NO 6
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa can be Val or Ile

<400> SEQUENCE: 6

```
Arg Ala Ser Gln Ser Xaa Ser Ser Asn Leu Ala
1               5                   10
```

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Ala or Gly
<220> FEATURE:
<221> NAME/KEY: misc_feature
<222> LOCATION: (3)..(4)
<223> OTHER INFORMATION: Xaa can be Ser or Thr

<400> SEQUENCE: 7

```
Xaa Ala Xaa Xaa Arg Ala Thr
1               5
```

<210> SEQ ID NO 8
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 8

Gln Gln Tyr Asn Asn Trp Pro Pro Leu Thr
1 5 10

<210> SEQ ID NO 9
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Gly or Ser
<220> FEATURE:
<221> NAME/KEY: misc_feature
<222> LOCATION: (2)..(2)
<223> OTHER INFORMATION: Xaa can be Asp or Ser
<220> FEATURE:
<221> NAME/KEY: misc_feature
<222> LOCATION: (6)..(6)
<223> OTHER INFORMATION: Xaa can be Gly or Asn

<400> SEQUENCE: 9

Xaa Xaa Tyr Tyr Trp Xaa
1 5

<210> SEQ ID NO 10
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa can be Asp or Ser
<220> FEATURE:
<221> NAME/KEY: misc_feature
<222> LOCATION: (6)..(6)
<223> OTHER INFORMATION: Xaa can be Gly or Ala
<220> FEATURE:
<221> NAME/KEY: misc_feature
<222> LOCATION: (14)..(14)
<223> OTHER INFORMATION: Xaa can be Leu or Val

<400> SEQUENCE: 10

Ser Ile Tyr His Xaa Xaa Tyr Thr Tyr Tyr Asn Pro Ser Xaa Lys Ser
1 5 10 15

<210> SEQ ID NO 11
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Asp or Gly
<220> FEATURE:
<221> NAME/KEY: misc_feature
<222> LOCATION: (2)..(2)
<223> OTHER INFORMATION: Xaa can be Ser or Val
<220> FEATURE:
<221> NAME/KEY: misc_feature
<222> LOCATION: (4)..(4)
<223> OTHER INFORMATION: Xaa can be Trp, Phe, or Ala
<220> FEATURE:
<221> NAME/KEY: misc_feature
<222> LOCATION: (8)..(8)
<223> OTHER INFORMATION: Xaa can be Ala or Gly
<220> FEATURE:
<221> NAME/KEY: misc_feature
<222> LOCATION: (9)..(9)
<223> OTHER INFORMATION: Xaa can be Phe or Tyr
<220> FEATURE:
<221> NAME/KEY: misc_feature
<222> LOCATION: (10)..(10)
<223> OTHER INFORMATION: Xaa can be Asp or Ala
<220> FEATURE:
<221> NAME/KEY: misc_feature
<222> LOCATION: (11)..(11)
<223> OTHER INFORMATION: Xaa can be Tyr or Ile

<400> SEQUENCE: 11

```
Xaa Xaa Gly Xaa Tyr Val Ile Xaa Xaa Xaa Xaa
1               5                   10
```

<210> SEQ ID NO 12
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa can be Val or Ile
<220> FEATURE:
<221> NAME/KEY: misc_feature
<222> LOCATION: (7)..(7)
<223> OTHER INFORMATION: Xaa can be Ser, Gly, or Tyr
<220> FEATURE:
<221> NAME/KEY: misc_feature
<222> LOCATION: (9)..(9)
<223> OTHER INFORMATION: Xaa can be Tyr or Asn

<400> SEQUENCE: 12

```
Arg Ala Ser Gln Ser Xaa Xaa Ser Xaa Leu Ala
1               5                   10
```

<210> SEQ ID NO 13
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Ala or Gly
<220> FEATURE:
<221> NAME/KEY: misc_feature
<222> LOCATION: (3)..(4)
<223> OTHER INFORMATION: Xaa can be Ser or Thr
<220> FEATURE:
<221> NAME/KEY: misc_feature
<222> LOCATION: (7)..(7)
<223> OTHER INFORMATION: Xaa can be Ser or Thr

<400> SEQUENCE: 13

```
Xaa Ala Xaa Xaa Arg Ala Xaa
1               5
```

<210> SEQ ID NO 14
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be Asn, Gly, or Ala
<220> FEATURE:
<221> NAME/KEY: misc_feature
<222> LOCATION: (5)..(5)
<223> OTHER INFORMATION: Xaa can be Asn, Ser, or Val
<220> FEATURE:
<221> NAME/KEY: misc_feature
<222> LOCATION: (6)..(6)
<223> OTHER INFORMATION: Xaa can be Trp or Ser
<220> FEATURE:
<221> NAME/KEY: misc_feature
<222> LOCATION: (9)..(9)
<223> OTHER INFORMATION: Xaa can be Leu, Ile, or Phe

<400> SEQUENCE: 14

Gln Gln Tyr Xaa Xaa Xaa Pro Pro Xaa Thr
1 5 10

<210> SEQ ID NO 15
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 15

Gly Asp Tyr Tyr Trp Gly
1 5

<210> SEQ ID NO 16
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 16

Ser Ile Tyr His Ser Gly Tyr Thr Tyr Tyr Asn Pro Ser Leu Lys Ser
1 5 10 15

<210> SEQ ID NO 17
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 17

Asp Ser Gly Trp Tyr Val Ile Ala Phe Asp Tyr
1 5 10

<210> SEQ ID NO 18
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 18

Asn Tyr Gly Ile His
1 5

<210> SEQ ID NO 19
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 19

Ala Ile Trp Tyr Asp Gly Asn Asn Lys Tyr Tyr Ala Asp Ser Val Lys
1 5 10 15

Asp

<210> SEQ ID NO 20
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 20

Asn Gly Val Leu Gly Ala Phe Asp Ile
1 5

<210> SEQ ID NO 21
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 21

Arg Ala Ser Gln Ser Val Ser Ser Asn Leu Ala
1 5 10

<210> SEQ ID NO 22
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 22

Gly Ala Ser Thr Arg Ala Thr
1 5

<210> SEQ ID NO 23
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 23

Arg Ala Ser Gln Gly Ile Ser Asn Tyr Leu Ala
1 5 10

<210> SEQ ID NO 24
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 24

Ala Ala Ser Thr Leu Gln Ser
1 5

<210> SEQ ID NO 25
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 25

Gln Lys Tyr Asn Ser Ser Pro Trp Thr
1 5

<210> SEQ ID NO 26
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 26

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Gly Ile His Trp Val Arg Gln Ala Pro Gly Lys Gly Leu Glu Trp Val
35 40 45

Ala Ala Ile Trp Tyr Asp Gly Asn Asn Lys Tyr Tyr Ala Asp Ser Val
50 55 60

Lys Asp Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Ala Arg Asn Gly Val Leu Gly Ala Phe Asp Ile Trp Gly Gln Gly Thr
100 105 110

Met Val Thr Val Ser Ser
115

<210> SEQ ID NO 27
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 27

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Asn Tyr
20 25 30

Leu Ala Trp Tyr Gln Gln Lys Pro Gly Lys Val Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Lys Tyr Asn Ser Ser Pro Trp
85 90 95

Thr Phe Gly Gln Gly Thr Lys Val Glu Ile Lys
100 105

<210> SEQ ID NO 28
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 28

Gly Asp Tyr Tyr Trp Asn
1 5

<210> SEQ ID NO 29
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 29

Ser Asp Tyr Tyr Trp Gly
1 5

<210> SEQ ID NO 30
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 30

Gly Ser Tyr Tyr Trp Gly
1 5

<210> SEQ ID NO 31
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 31

Ser Ile Tyr His Asp Gly Tyr Thr Tyr Tyr Asn Pro Ser Leu Lys Ser
1 5 10 15

<210> SEQ ID NO 32
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 32

Ser Ile Tyr His Ser Ala Tyr Thr Tyr Tyr Asn Pro Ser Leu Lys Ser
1 5 10 15

<210> SEQ ID NO 33
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 33

Ser Ile Tyr His Ser Gly Tyr Thr Tyr Tyr Asn Pro Ser Val Lys Ser
1 5 10 15

<210> SEQ ID NO 34
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 34

Asp Ser Gly Trp Tyr Val Ile Ala Phe Ala Tyr
1 5 10

<210> SEQ ID NO 35
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 35

Asp Ser Gly Trp Tyr Val Ile Ala Phe Asp Ile
1 5 10

<210> SEQ ID NO 36
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 36

Asp Ser Gly Trp Tyr Val Ile Gly Phe Asp Tyr
1 5 10

<210> SEQ ID NO 37
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 37

Asp Ser Gly Trp Tyr Val Ile Ala Tyr Asp Tyr
1 5 10

<210> SEQ ID NO 38
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 38

Asp Val Gly Trp Tyr Val Ile Ala Phe Asp Tyr
1 5 10

<210> SEQ ID NO 39
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 39

Asp Ser Gly Phe Tyr Val Ile Ala Phe Asp Tyr
1 5 10

<210> SEQ ID NO 40
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 40

Asp Ser Gly Ala Tyr Val Ile Ala Phe Asp Tyr 1 5 10

<210> SEQ ID NO 41
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 41

Asp Val Gly Trp Tyr Val Ile Ala Phe Asp Ile
1 5 10

<210> SEQ ID NO 42
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 42

Asp Val Gly Phe Tyr Val Ile Ala Phe Asp Tyr
1 5 10

<210> SEQ ID NO 43
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 43

Asp Val Gly Phe Tyr Val Ile Ala Phe Asp Ile
1 5 10

<210> SEQ ID NO 44
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 44

Asp Ser Gly Phe Tyr Val Ile Ala Phe Asp Ile
1 5 10

<210> SEQ ID NO 45
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 45

Asp Ser Gly Trp Tyr Val Ile Gly Tyr Asp Tyr
1 5 10

<210> SEQ ID NO 46
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 46

Gly Ser Gly Trp Tyr Val Ile Ala Phe Asp Tyr
1 5 10

<210> SEQ ID NO 47
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 47

Glu Ser Gly Trp Tyr Val Ile Ala Phe Asp Tyr
1 5 10

<210> SEQ ID NO 48
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 48

Asp Ser Gly Trp Ser Val Ile Ala Phe Asp Tyr
1 5 10

<210> SEQ ID NO 49
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 49

Arg Ala Ser Gln Ser Ile Ser Ser Asn Leu Ala
1 5 10

<210> SEQ ID NO 50
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 50

Arg Ala Ser Gln Ser Val Gly Ser Asn Leu Ala
1 5 10

<210> SEQ ID NO 51
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 51

Arg Ala Ser Gln Ser Val Tyr Ser Asn Leu Ala
1 5 10

<210> SEQ ID NO 52
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 52

Arg Ala Ser Gln Ser Val Ser Ser Tyr Leu Ala
1 5 10

<210> SEQ ID NO 53
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 53

Ala Ala Ser Thr Arg Ala Thr
1 5

<210> SEQ ID NO 54
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 54

Gly Ala Thr Thr Arg Ala Thr
1 5

<210> SEQ ID NO 55
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 55

Gly Ala Ser Ser Arg Ala Thr
1 5

<210> SEQ ID NO 56
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 56

Gly Ala Ser Thr Arg Ala Ser
1 5

<210> SEQ ID NO 57
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 57

Gln Gln Tyr Ala Asn Trp Pro Pro Leu Thr
1 5 10

<210> SEQ ID NO 58
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 58

Gln Gln Tyr Asn Val Trp Pro Pro Leu Thr
1 5 10

<210> SEQ ID NO 59
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 59

Gln Gln Tyr Asn Asn Ser Pro Pro Leu Thr
1 5 10

<210> SEQ ID NO 60
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 60

Gln Gln Tyr Asn Asn Trp Pro Pro Ile Thr
1 5 10

<210> SEQ ID NO 61
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 61

Gln Gln Tyr Asn Asn Trp Pro Pro Phe Thr
1 5 10

<210> SEQ ID NO 62
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 62

Gln Gln Tyr Gly Asn Trp Pro Pro Leu Thr
1 5 10

<210> SEQ ID NO 63
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 63

Gln Gln Tyr Asn Ser Trp Pro Pro Leu Thr
1 5 10

<210> SEQ ID NO 64
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 64

Gln Gln Arg Asn Asn Trp Pro Pro Leu Thr
1 5 10

<210> SEQ ID NO 65

<211> LENGTH: 330
<212> TYPE: PRT
<213> ORGANISM: Artificial Sequence
<220> FEATURE:
<223> OTHER INFORMATION: Synthetic polypeptide

<400> SEQUENCE: 65

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 66
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Gly Asp
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ser Gly Trp Tyr Val Ile Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 67
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 67

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Gly Ile His Trp Val Arg Gln Ala Pro Gly Lys Gly Leu Glu Trp Val
35 40 45

Ala Ala Ile Trp Tyr Asp Gly Asn Asn Lys Tyr Tyr Ala Asp Ser Val
50 55 60

Lys Asp Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Tyr Cys
85 90 95

Ala Arg Asn Gly Val Leu Gly Ala Phe Asp Ile Trp Gly Gln Gly Thr
100 105 110

Met Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 68
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 68

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Glu Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Pro
85 90 95

Leu Thr Phe Gly Gly Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 69

-continued

```
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```